(12) United States Patent
Gillespie et al.

(10) Patent No.: US 8,536,214 B2
(45) Date of Patent: Sep. 17, 2013

(54) INDANE DERIVATIVES AS AMPA RECEPTOR MODULATORS

(76) Inventors: Jonathan Gillespie, Lanarkshire (GB); Craig Jamieson, Lanarkshire (GB); John Kinaird Fergusen MaClean, Lanarkshire (GB); Elizabeth Margaret Moir, Lanarkshire (GB); Zoran Rankovic, Lanarkshire (GB)

( * ) Notice: Subject to any disclaimer, the term of this patent is extended or adjusted under 35 U.S.C. 154(b) by 93 days.

(21) Appl. No.: 12/996,183

(22) PCT Filed: Jun. 3, 2009

(86) PCT No.: PCT/EP2009/056791
§ 371 (c)(1),
(2), (4) Date: Dec. 3, 2010

(87) PCT Pub. No.: WO2009/147167
PCT Pub. Date: Dec. 10, 2009

(65) Prior Publication Data
US 2011/0092539 A1    Apr. 21, 2011

(30) Foreign Application Priority Data
Jun. 6, 2008 (EP) .................................. 08157705

(51) Int. Cl.
*A61K 31/415* (2006.01)
*C07D 231/10* (2006.01)

(52) U.S. Cl.
USPC ................. 514/406; 548/365.4; 548/375.1

(58) Field of Classification Search
None
See application file for complete search history.

(56) References Cited

U.S. PATENT DOCUMENTS

| | | | |
|---|---|---|---|
| 7,253,189 B2 * | 8/2007 | Tong et al. | 514/339 |
| 2012/0202781 A1 | 8/2012 | Gillen et al. | |

FOREIGN PATENT DOCUMENTS

| WO | 02/060874 A1 | 8/2002 |
|---|---|---|
| WO | 2004/048322 A1 | 6/2004 |
| WO | 2005/040110 A1 | 5/2005 |
| WO | 2005/070916 A1 | 8/2005 |
| WO | 2005/105759 A1 | 11/2005 |
| WO | 2006/015828 A1 | 2/2006 |
| WO | 2006/015829 A1 | 2/2006 |
| WO | 2010115952 A1 | 10/2010 |

OTHER PUBLICATIONS

Arai, et al., "Benzamide-Type AMPA Receptor Modulators Form Two Subfamilies with Distinct Modes of Action," The Journal of Pharmacology and Experimental Therapeutics, 2002, vol. 303, No. 3, pp. 1075-1085.
Lynch, "Glutamate-based therapeutic approaches:ampakines," Current Opinion in Pharmacology, 2006, vol. 6, pp. 82-88.
Ornstein, et al., "Biarulpropylsulfonamides as Novel, Potent Potentiators of 2-Amino-3-(5-methyl-3-hydroxyisoxazol-4-yl)-propanoic Acid (AMPA) Receptors," J. Med. Chem., 2000, vol. 43, pp. 4354-4358.
Pirotte, et al., "4H-1,2,4-Pyridothiadiazine 1,1-Dioxides and 2,3-Dihydro,4H-1,2,4-pyridothiadiazine 1,1-Dioxides Chemically Related to Diazoxide . . . " J. Med. Chem., 1998, vol. 41, pp. 2946-2959.
Yamada, "Therapeutic potential of positive AMPA receptor modulators in the treatment of neurological disease," Expert Opinion on Investigational Drugs, 2000, vol. 9, pp. 765-777.

* cited by examiner

*Primary Examiner* — Kamal Saeed

(57) ABSTRACT

The present invention relates to a heterocyclic derivative according to formula (I); wherein the variables are defined as in the specification, or to a pharmaceutically acceptable salt or solvate thereof. The present invention also relates to a pharmaceutical composition comprising said heterocyclic derivatives and to their use in therapy, for instance in the treatment or prevention of psychiatric diseases where an enhancement of synaptic responses mediated by AMPA receptors is required, including schizophrenia, depression and Alzheimer's disease.

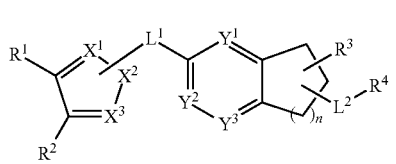

(I)

13 Claims, No Drawings

INDANE DERIVATIVES AS AMPA RECEPTOR MODULATORS

RELATED APPLICATIONS

This application is a 371 of PCT/EP09/056,791 filed Jun. 3, 2009.

The present invention relates to heterocyclic derivatives, to pharmaceutical compositions comprising these compounds and to their use in therapy, in particular to their use for the treatment or prevention of psychiatric diseases where an enhancement of synaptic responses mediated by AMPA receptors is required.

L-glutamate is the most abundant excitatory neurotransmitter located in the mammalian central nervous system (CNS). L-glutamate plays a significant role in the control of cognition, mood and motor function and these processes are imbalanced in psychiatric and neurological disorders. The physiological effects of glutamate are mediated through two receptor families, the metabotropic (G-protein coupled) receptors and the ionotropic (ligand-gated ion channels) receptors. The ionotropic receptors are responsible for mediating the fast synaptic response to extracellular L-glutamate. The ionotropic glutamate receptors are separated into three subclasses on the basis of molecular and pharmacological differences and are named after the small molecule agonists which were originally identified to selectively activate them: AMPA (α-amino-3-hydroxy-5-methyl-4-isoxazole-propionic acid), NMDA (N-methyl-D-aspartate) and kainate (2-carboxy-3-carboxymethyl-4-isopropenylpyrrolidine).

The importance of AMPA receptors in brain physiology is widely recognised and it has been shown that AMPA receptors control the majority of fast excitatory amino acid transmission in the CNS and also contribute to synaptic plasticity playing a role in a variety of physiological processes such as learning and memory. To this end there has been a growing appreciation of the utility of positive allosteric modulators of the AMPA receptor for a variety of clinical indications including schizophrenia, depression and Alzheimer's disease.

AMPA receptor subunits are encoded by four distinct genes (termed GluR1 to 4), each representing proteins of around 900 amino acids. The individual sub-units consist of a large extracellular N-terminal domain, an extracellular ligand binding site for L-glutamate formed by domains designated S1 and S2. The transmembrane domain consists of three transmembrane regions, M1, M3 and M4 together with the re-entrant loop M2. This is then followed by a long intracellular C-terminal domain. All four AMPA receptor subunits contain so-called 'flip' and 'flop' splice variants which differ in alternate slicing of 38 amino acid encoding exons (differing by less than 10 amino acids) in the S2 extracellular domain. Further heterogeneity of the AMPA receptors results from RNA editing, the most significant being the Q/R site located in the pore region (M2) of the GluR2 subunit. The R variant, which a large proportion of native GluR2 subunits are believed to comprise, is characterised by significantly reduced calcium permeability. A further R/G editing site is located in the S2 domain of GluR2, GluR3 and GluR4 with the G form exhibiting an acceleration in the kinetics of recovery from desensitisation.

The kinetics of desensitisation and deactivation are important functional properties of the AMPA receptor that control the magnitude and duration of the synaptic response to glutamate. The processes of desensitisation and deactivation can be modulated by AMPA receptor positive allosteric modulators that bind remotely from the agonist binding site, yet influence agonist binding, or indeed agonist mediated conformational changes in the receptor associated with gating and/or desensitisation. Consequently there are continued efforts to develop drugs that specifically target these properties and which will have therapeutic potential in the treatment of a wide variety of CNS disorders associated with diminished glutamatergic signalling. Examples of these conditions include age-related memory impairment, Alzheimer's Disease, Parkinson's Disease, depression, psychosis, cognitive defects associated with psychosis, attention deficit disorder and attention deficit hyperactivity disorder.

A variety of structural classes of compounds are known which act as AMPA receptor modulators (see G. Lynch, *Current Opinion in Pharmacology*, 2006, 6, 82-88 for a recent review). For example, there are the so-called benzamide compounds related to aniracetam (see A. Arai et al., *J Pharmacol Exp. Ther.*, 2002, 30, 1075-1085), the benzothiadiazine derivatives such as S-18689 (see B. Pirotte, *J. Med. Chem.*, 1998, 41, 2946-2959) and the biarylpropylsulfonamide derivatives (see P. L. Ornstein et al., *J. Med. Chem.* 2000, 43, 4354-4358). Another class of AMPA receptor modulators was disclosed in International Patent Applications WO 2005/040110 and WO 2005/070916 which detail various heterocyclic compounds as being of utility as glutamate modulators. Further classes of compounds indicated to potentiate the glutamate receptor and their uses in medicine are disclosed in WO 2006/015828 and WO 2006/015829. Compounds in each of these classes exhibit varying degrees of potentiation of the AMPA receptor.

Sustained AMPA receptor activation, however, is also associated with seizures and other proconvulsant side effects (Yamada K. A., *Exp. Opin. Invest. Drugs* 2000, 9, 765-777). Consequently there remains a need for further AMPA receptor modulators which have an optimal separation between beneficial therapeutic effects and unwanted neurotoxic effects.

WO 2002/060874 relates to a series of potassium channel inhibitors indicated to be especially useful for the treatment of cardiac arrhythmias and cell proliferative disorders. WO 2005/105759 relates to substituted tetrahydropyridopyrimidine and tetrahydroquinazoline compounds and to their use as medicines.

In a first aspect the present invention relates to a heterocyclic derivative according to formula I

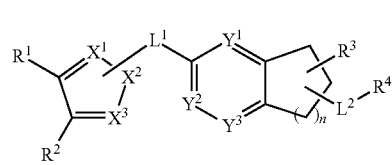

formula I wherein
$L^1$ is O, $NR^5$, $(CR^6R^7)_m$, CO or $SO_2$;
$L^2$ is $NR^8SO_2$ or $SO_2NR^9$;
$R^1$ is H, $C_{1-6}$alkyl, $C_{3-8}$cycloalkyl, $C_{1-6}$alkyloxy, halogen, CN, $COR^{10}$, $SR^{11}$, $SOR^{12}$, $SO_2R^{13}$, $NHCOR^{14}$, $NHSO_2R^{15}$, $NHCOR^{16}$ or $CONHR^{17}$, said $C_{1-6}$alkyl, $C_{3-8}$cycloalkyl and $C_{1-6}$alkyloxy being optionally substituted with one or more halogens;
$R^2$ is $C_{1-6}$alkyl, $C_{3-8}$cycloalkyl, $C_{1-6}$alkyloxy, or CN, said $C_{1-6}$alkyl, $C_{3-8}$cycloalkyl and $C_{1-6}$alkyloxy being substituted with one or more moiety independently selected from halogen, OH, $C_{1-6}$alkyloxy, CN, $NR^{18}R^{19}$, $COR^{29}$, $SR^{21}$, $SOR^{22}$, $SO_2R^{23}$, $NHCOR^{24}$, $NHSO_2R^{25}$, $NHCOR^{26}$ and $CONHR^{27}$ or R² together with X³, wherein X³ is CR³¹, forms a 5 to 7 membered unsaturated carbocyclic ring optionally comprising a N;

R³ is H, $C_{1-6}$alkyl, $C_{3-8}$cycloalkyl, $C_{1-6}$alkyloxy, halogen or CN, said $C_{1-6}$alkyl, $C_{3-8}$cycloalkyl and $C_{1-6}$alkyloxy being optionally substituted with one or more halogens;

R⁴ is H, $C_{1-6}$alkyl, $C_{2-6}$alkenyl, $C_{2-6}$alkynyl, $C_{3-8}$cycloalkyl, $C_{1-2}$alkyl$C_{3-8}$cycloalkyl, NR²⁸R²⁹, $C_{6-10}$aryl or a 5-9 membered heteroaryl ring system comprising 1-2 heteroatoms independently selected from O, S and N, wherein said $C_{1-6}$alkyl, $C_{3-8}$cycloalkyl, $C_{6-10}$aryl and 5-9 membered heteroaryl ring system are optionally substituted with one or more moieties independently selected from halogen, $C_{1-6}$alkyl, hydroxy and $C_{1-6}$alkyloxy, said $C_{1-6}$alkyl, and $C_{1-6}$alkyloxy being optionally substituted with 1-3 halogens;

R⁵-R¹⁰ are independently H or $C_{1-6}$alkyl;

R¹¹-R¹⁶ are independently $C_{1-6}$alkyl;

R¹⁷ is H or $C_{1-6}$alkyl;

R¹⁸ and R¹⁹ are independently H or $C_{1-4}$alkyl optionally substituted with a 5-9 membered heteroaryl ring system comprising 1-2 heteroatoms independently selected from O, S and N, or R¹⁸ and R¹⁹ together with the N to which they are bonded form a 4-6 membered saturated or unsaturated heterocyclic ring optionally comprising another heteroatom selected from O, S and N(R³⁰)$_p$;

R²⁰ is independently H or $C_{1-4}$alkyl;

R²¹-R²⁶ are independently $C_{1-4}$alkyl;

R²⁷ is H or $C_{1-4}$alkyl

R²⁸ and R²⁹ are independently H or $C_{1-4}$alkyl or R²⁸ and R²⁹ together with the N to which they are bonded form a 4-6 membered saturated or unsaturated heterocyclic ring optionally comprising another heteroatom selected from O, S and N;

R³⁰ is H or $C_{1-4}$alkyl;

m is 1-2;

n is 1-3;

p is 0 or 1;

X¹ and X³ are independently O, S, N or CR³¹ and X² is N or CR³¹ with the proviso that at least one of X¹-X³ must be N and that no more than one of X¹ and X³ can be O or S or X³ together with R², wherein X³ is CR³¹, forms a 5 to 7 membered unsaturated carbocyclic ring optionally comprising a N;

Y¹-Y³ are independently CR³² or N, with the proviso that only 1 of Y¹—Y³ can be N;

R³¹ is H or $C_{1-6}$alkyl and

R³² is H, $C_{1-6}$alkyl, $C_{3-8}$cycloalkyl, $C_{1-6}$alkyloxy, halogen or CN, said $C_{1-6}$alkyl, $C_{3-8}$cycloalkyl and $C_{1-6}$alkyloxy being optionally substituted with one or more halogens;

or a pharmaceutically acceptable salt or solvate thereof.

The term $C_{1-6}$alkyl, as used herein, represents a branched or unbranched alkyl group having 1-6 carbon atoms. Examples of such groups are methyl, ethyl, isopropyl, tertiary butyl and n-pentyl. Similarly the term $C_{1-4}$alkyl, as used herein, represents a branched or unbranched alkyl group having 1-4 carbon atoms. Examples of such groups are methyl, ethyl, isopropyl and tertiary butyl.

The term $C_{2-6}$alkenyl, as used herein, represents a branched or unbranched alkenyl group having 2-6 carbon atoms and at least one double bond. Examples of such groups are ethenyl and isopropenyl.

The term $C_{2-6}$alkynyl, as used herein, represents a branched or unbranched alkynyl group having 2-6 carbon atoms and at least one triple bond. Examples of such groups are ethynyl and propynyl.

The term $C_{3-8}$cycloalkyl, as used herein, represents a branched or unbranched cyclic alkyl group having 3-8 carbon atoms. Examples of such groups are cyclopropyl, cyclopentyl and 2-methylcyclohexyl.

The term $C_{3-8}$cycloalkyl$C_{1-2}$alkyl, as used herein, represents a $C_{1-2}$alkyl group which is substituted with a $C_{3-8}$cycloalkyl group. Examples of such groups are cyclopropylmethyl, and 2-cyclobutylethyl.

The term $C_{1-6}$alkyloxy, as used herein, represents a branched or unbranched alkyloxy group having 1-6 carbon atoms. Examples of such groups are methoxy, ethoxy, isopropyloxy and tertiary butyloxy.

The term $C_{6-10}$aryl, as used herein, represents an aromatic group having 6-10 carbon atoms and comprising one ring or two rings fused together, at least one of which must be aromatic. Examples of such groups include phenyl and naphthyl.

The term halogen, as used herein, represents a fluorine, chlorine, bromine or iodine.

The term solvate, as used herein, refers to a complex of variable stoichiometry formed by a solvent and a solute (in this invention, a compound of formula I). Such solvents may not interfere with the biological activity of the solute. Examples of suitable solvents include, water, ethanol and acetic acid.

Examples of 5 to 9 membered heteroaryl ring systems comprising 1-2 heteroatoms selected from O, S and N include furan, pyrrole, thiophene, imidazole, pyrrazole, thiazole, pyridine, pyrimidine, indole, indazole and benzothiophene.

Examples of 4 to 6 membered saturated or unsaturated heterocyclic ring optionally comprising another heteroatom selected from O, S and N include pyrrole, imidazole, pyrazole, thiazole, pyridine piperidine morpholine and piperazine.

The skilled person will appreciate that L¹ can be attached to the five membered heteroaryl ring containing X¹-X³ at either X¹ or X². The skilled person will likewise appreciate that R³ and L² can be attached to the fused bicyclic ring at any of the methylenes of said fused bicyclic ring and that R³ and L² can be attached to the same or different methylene.

In one embodiment of the present invention L¹ is O or NR⁵, wherein R⁵ has the previously defined meanings. In a further embodiment, L¹ is CO or SO₂.

In another embodiment of the present invention L¹ is (CR⁶R⁷)$_m$, wherein R⁶, R⁷ and m are selected independently and have the previously defined meanings. In a further embodiment, L¹ is CH₂ or CH₂CH₂. In a further embodiment, L¹ is CH(CH₃). In a further embodiment, L¹ is CH₂.

In another embodiment of the present invention L² is NHSO₂ or SO₂NH. In a further embodiment, L² is N(CH₃)SO₂ or SO₂N(CH₃). In a further embodiment, L² is NHSO₂

In another embodiment of the present invention R¹ is $C_{1-4}$alkyl or CN, said $C_{1-4}$alkyl being optionally substituted with 1-3 halogens. In a further embodiment, R¹ is trifluoromethyl. In a further embodiment, R¹ is isopropyl, tertiary-butyl or CN. In a still further embodiment, R¹ is SO₂CH₃ or NHSO₂CH₃.

In another embodiment of the present invention R² is $C_{1-4}$alkyl, or $C_{1-4}$alkyloxy, said $C_{1-4}$alkyl and $C_{1-4}$alkyloxy being substituted with halogen, OH, $C_{1-4}$alkyloxy or NR¹⁸R¹⁹, wherein R¹⁸ and R¹⁹ are selected independently and have the previously defined meanings. In another embodiment, R² is methyl substituted with halogen, OH, $C_{1-4}$alkyloxy or NR¹⁸R¹⁹, wherein R¹⁸ and R¹⁹ are selected independently and have the previously defined meanings. In a further embodiment, R² is —CH₂OH, —CH₂CH₂OH or —CH(CH₃)₂OH. In a further embodiment, R² is $C_{1-4}$alkyl substituted with amino, methylamino or dimethylamino. In a further embodiment, $R^2$ is aminomethyl, $CH_2N(CH_3)_2$, $(CH_2)_2N(CH_3)_2$ or $(CH_2)_2NH(CH_2)_2OH$. In a further embodiment, $R^2$ is $C_{1-4}$alkyl substituted with halogen. In a further embodiment, $R^2$ is $CF_3$ or $CH_2F$.

In another embodiment of the present invention $R^3$ is H, $C_{1-6}$alkyl or $C_{1-6}$alkyloxy. In a further embodiment, $R^3$ is H, $C_{1-4}$alkyl or $C_{1-4}$alkyloxy. In a further embodiment, $R^3$ is H or methyl. In a further embodiment, $R^3$ is H.

In another embodiment of the present invention $R^4$ is H, $C_{1-6}$alkyl, $C_{3-8}$cycloalkyl, $C_{1-2}$alkyl$C_{3-8}$cycloalkyl or $NR^{28}R^{29}$, wherein said $C_{1-6}$alkyl and $C_{3-8}$cycloalkyl are optionally substituted with one or more halogens. In a further embodiment, $R^4$ is H, $C_{1-4}$alkyl, $C_{3-8}$cycloalkyl or $C_{1-2}$alkyl$C_{3-8}$cycloalkyl wherein said $C_{1-4}$alkyl and $C_{3-8}$cycloalkyl are optionally substituted with one or more halogens. In a further embodiment, $R^4$ is methyl, ethyl, isopropyl or tertiary-butyl, wherein said methyl, ethyl, isopropyl and tertiary-butyl are optionally substituted with one or more halogens. In a further embodiment, $R^4$ is cyclopropyl, cyclobutyl, cyclopentyl, cyclohexyl, cyclopropylmethyl, cyclobutylmethyl, cyclopentylmethyl or cyclohexylmethyl. In a further embodiment $R^4$ is amino, $NHCH_3$, $N(CH_3)_2$, $NHCH_2CH_3$ or $NH(CH_2CH_3)_2$. In a further embodiment, $R^4$ is piperidine, pyrrolidine, morpholine or 4-methylpiperazine.

In another embodiment of the present invention $R^4$ is $C_{6-10}$aryl or a 5-9 membered heteroaryl ring system comprising 1-2 heteroatoms independently selected from O, S and N, wherein said $C_{6-10}$aryl and 5-9 membered heteroaryl ring system are optionally substituted with one or more moieties independently selected from halogen, $C_{1-6}$alkyl, hydroxy or $C_{1-6}$alkyloxy, said $C_{1-6}$alkyl and $C_{1-6}$alkyloxy being optionally substituted with 1-3 halogens. In a further embodiment, $R^4$ is an aryl or heteroaryl group selected from phenyl, thienyl, pyrrolyl, thiazolyl, furanyl, oxazolyl, imidazolyl, pyrazolyl, pyridyl and pyrimidyl, said aryl or heteroaryl group being optionally substituted with methyl, trifluoromethyl, methoxy or halogen. In a further embodiment, $R^4$ is phenyl or thienyl, said phenyl or thienyl being optionally substituted with halogen, $C_{1-4}$alkyl or $C_{1-4}$alkyloxy. In a further embodiment, $R^4$ is phenyl or thienyl, said phenyl or thienyl being optionally substituted with halogen, methyl or methoxyl.

In a further embodiment of the present invention, $X^1$ is N, $X^2$ is N and $X^3$ is $CR^{31}$, wherein $R^{31}$ is H or $C_{1-4}$alkyl, optionally substituted with one or more halogens. In a further embodiment of the present invention, $X^1$ is N, $X^2$ is N and $X^3$ is $CR^{31}$, wherein $R^{31}$ is H, methyl, ethyl or trifluoromethyl.

In a further embodiment of the present invention, $X^1$ is $CR^{31}$, $X^2$ is N and $X^3$ is N, wherein $R^{31}$ is H or $C_{1-4}$alkyl, optionally substituted with one or more halogens. In a further embodiment of the present invention, $X^1$ is $CR^{31}$, $X^2$ is N and $X^3$ is N, wherein $R^{31}$ is H, methyl, ethyl or trifluoromethyl.

In another embodiment of the present invention, the fragment

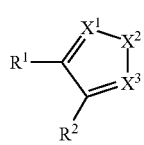

is selected from:

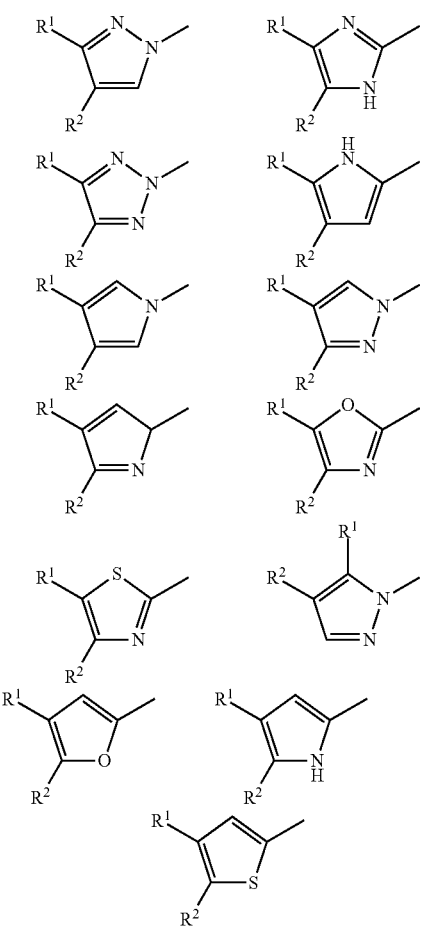

wherein $R^1$ and $R^2$ are selected independently and have the previously defined meanings.

In another embodiment of the present invention, the fragment

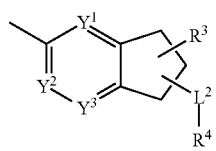

is selected from:

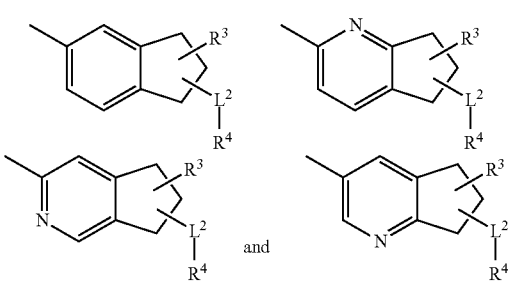

wherein $R^3$, $L^2$ and $R^4$ are selected independently and have the previously defined meanings.

In another embodiment of the present invention, the fragment

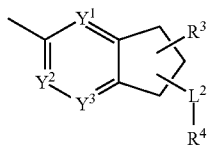

is selected from:

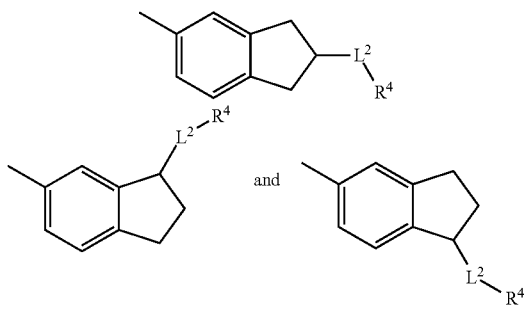

wherein $L^2$ and $R^4$ are selected independently and have the previously defined meanings.

In another embodiment of the present invention is a heterocyclic derivative having the formula II

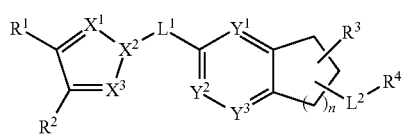

formula II wherein $R^1$-$R^4$, $L^1$, $L^2$ $X^1$-$X^3$, $Y^1$-$Y^3$ and n are selected independently and have the previously defined meanings.

In another embodiment of the present invention is a heterocyclic derivative having the formula III

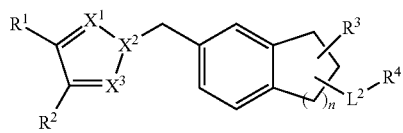

formula III wherein $X^1$-$X^3$, $R^1$-$R^4$, $L^2$ and n are selected independently and have the previously defined meanings.

In a further embodiment of the present invention is a heterocyclic derivative having the general formula IV

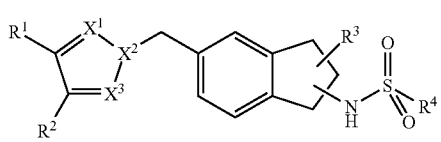

formula IV wherein $X^1$-$X^3$ and $R^1$-$R^4$ are selected independently and have the previously defined meanings.

In another embodiment of the present invention is a heterocyclic derivative having the formula V

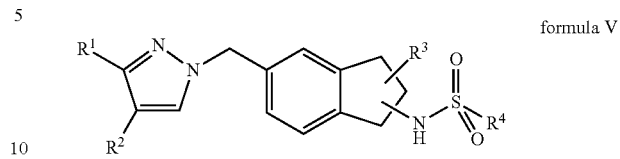

formula V wherein $R^1$-$R^4$ are selected independently and have the previously defined meanings.

In another embodiment of the present invention is a heterocyclic derivative having the formula VI

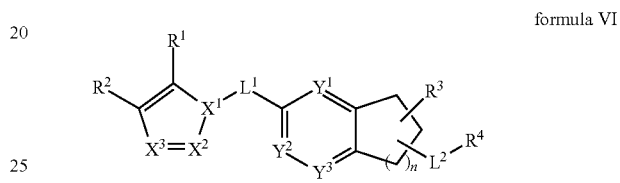

formula VI wherein $R^1$-$R^4$, $L^1$, $L^2$ $X^1$-$X^3$, $Y^1$-$Y^3$ and n are selected independently and have the previously defined meanings.

In a further embodiment of the present invention is a heterocyclic derivative having the general formula VII

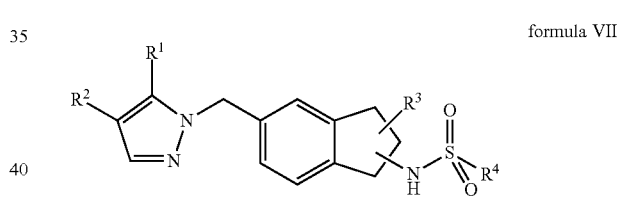

formula VII wherein $R^1$-$R^4$ are selected independently and have the previously defined meanings.

In another embodiment of the present invention is a heterocyclic derivative selected from:

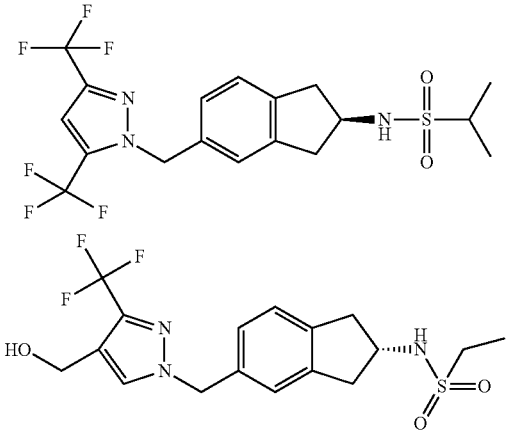

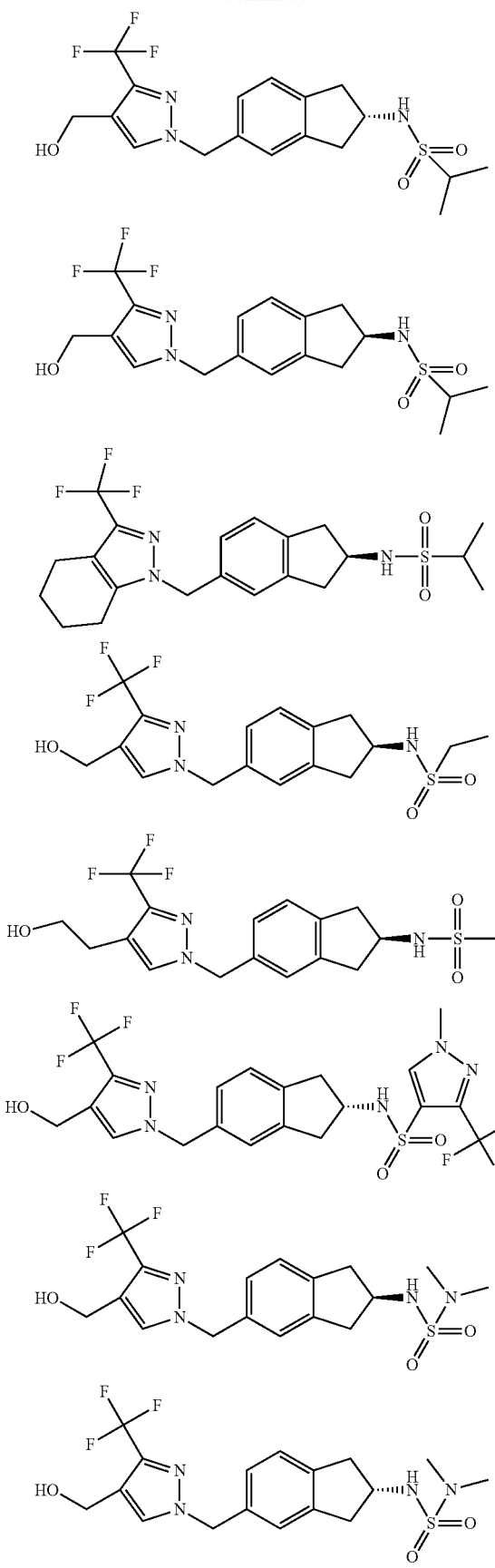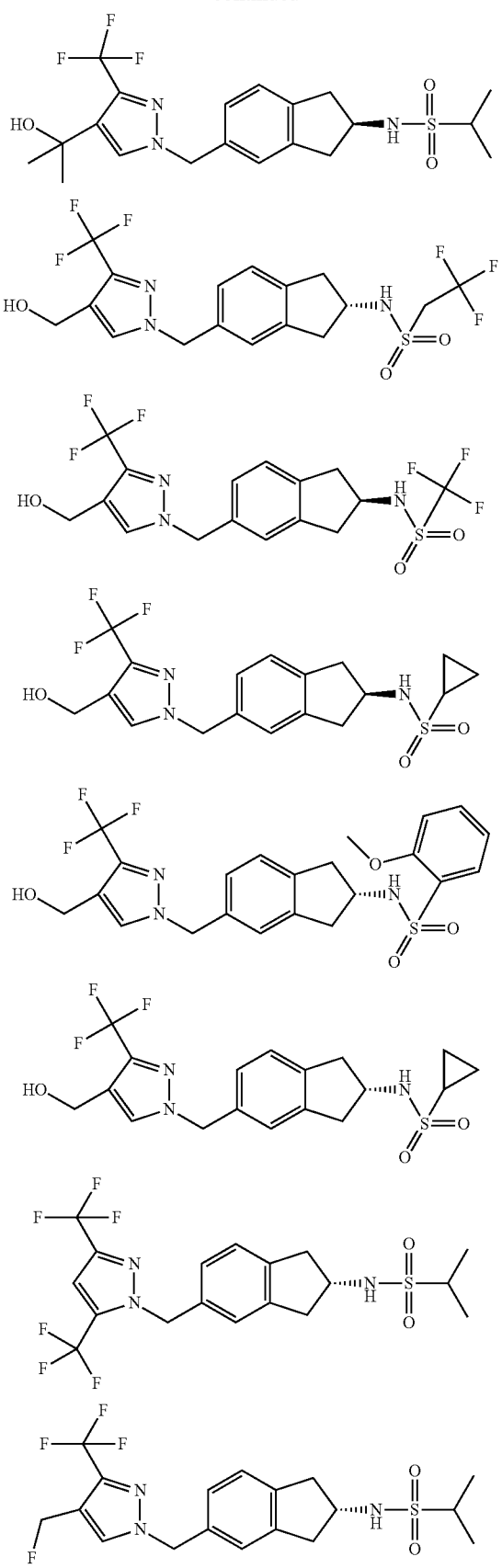

-continued

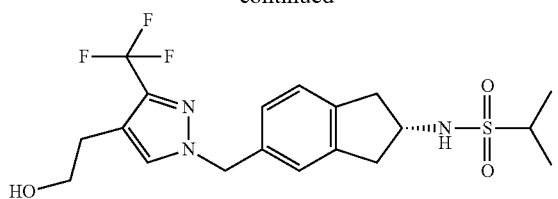

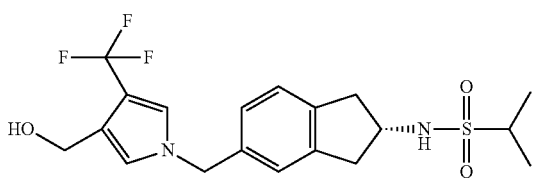

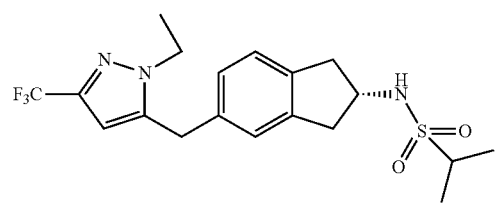

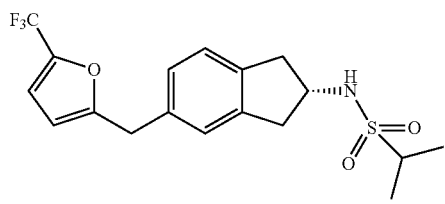

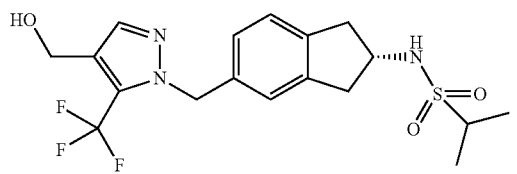

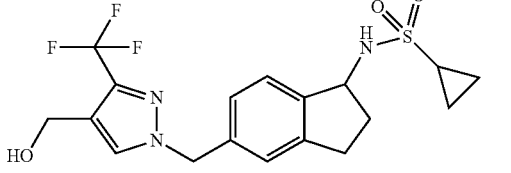

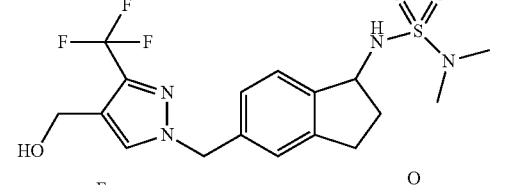

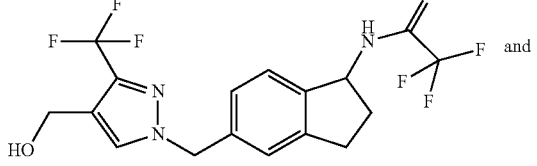

and

-continued

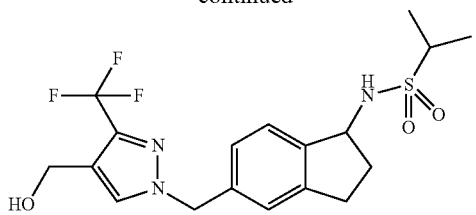

or a pharmaceutically acceptable salt or solvate thereof.

The heterocyclic derivatives of the present invention are prepared by methods well known in the art of organic chemistry. See, for example, J. March, 'Advanced Organic Chemistry' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' $2^{nd}$ Edition, John Wiley and Sons, 1991. The protective groups are optionally removed at a convenient subsequent stage using methods well known in the art.

The synthesis of heterocyclic derivatives of formula (1) may be accomplished as outlined in Scheme 1. Thus, arylcycloalkylamines (2) may be halogenated with, for example, bromine in water, to give bromoarylcycloalkylamines (3). These in turn can be sulfonylated in the presence of a suitable organic base, such as 1,1,1-diazabicycloundecane (DBU), to give the sulphonamide (4). Subsequently functionalisation, for example, by treatment of (4) with an appropriate carbon monoxide source, such as molybdenum hexacarbonyl in, for example, methanol/acetonitrile and with the appropriate catalyst/ligand combination (using, for example, Herrmann's catalyst i.e., tri-tert-butylphosphine tetrafluoroborate as catalyst) gives the product (5), wherein $L^1$-LG is a methoxycarbonyl group. Subsequent reaction with a suitably functionalised heterocycle (6) in the presence of a suitable base, for example potassium hydroxide, in turn provides the desired adduct (1) by displacement of an appropriate leaving group LG.

For example, the compound (I), wherein $L^1$ is methylene can be prepared starting from the precursor (5), wherein $L^1$-LG is a methoxycarbonyl group by reduction of (5) with, for example, lithium aluminium hydride in tetrahydrofuran to give the intermediate alcohol (wherein $L^1$-LG is hydroxymethyl). This can then be readily chlorinated with a suitable chlorinating reagent such as thionyl chloride to provide the intermediate alkylchloride (wherein $L^1$-LG is chloromethyl), which in turn can be reacted with a suitably functionalised heterocycle (6) in the presence of a suitable base, for example potassium carbonate to provide the desired adduct (1). Other variants of $L^1$-LG and heterocycles (6) will be apparent to the skilled person. For example, $L^1$-LG could be an acid chloride moiety (i.e., $L^1$ as CO and LG as Cl) and the heterocycle (6) could be a 2-lithiopyrrole, prepared, for example, by reaction of 2-bromopyrrole with n-butyllithium.

Scheme 1

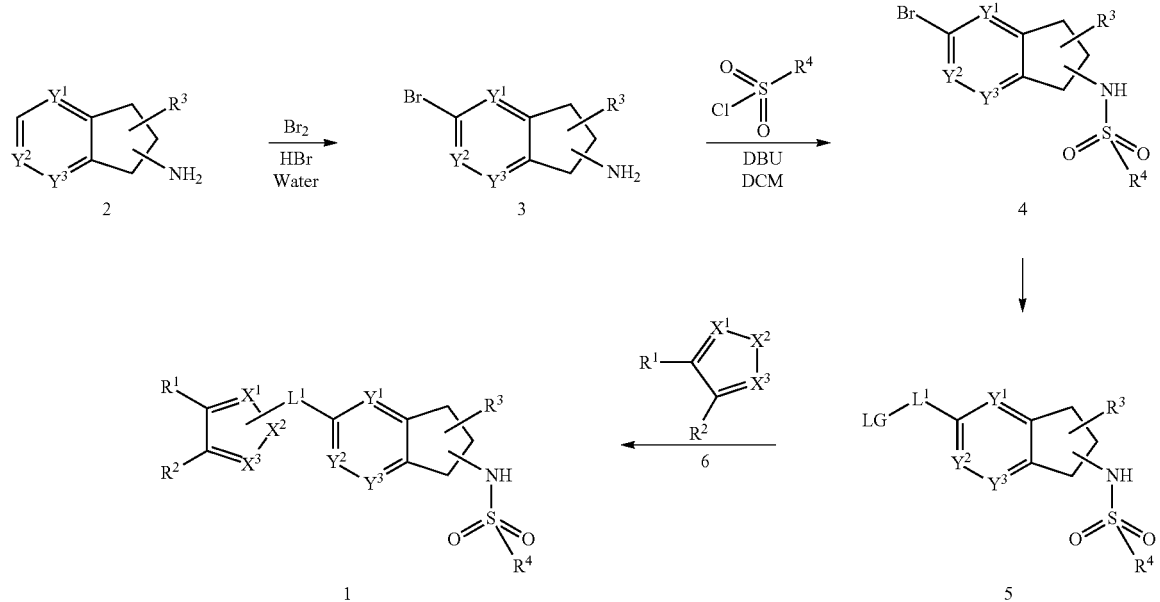

The various reagents and starting materials are either commercially available or are readily prepared using methods well known to the skilled person.

The skilled person will appreciate that the heterocyclic derivatives of formula I can alternatively be prepared using an analogous process to that of Scheme 1 but with the steps carried out in a different order. Hence, it is possible to prepare compounds of the type (11) as adumbrated in Scheme 2.

Scheme 2

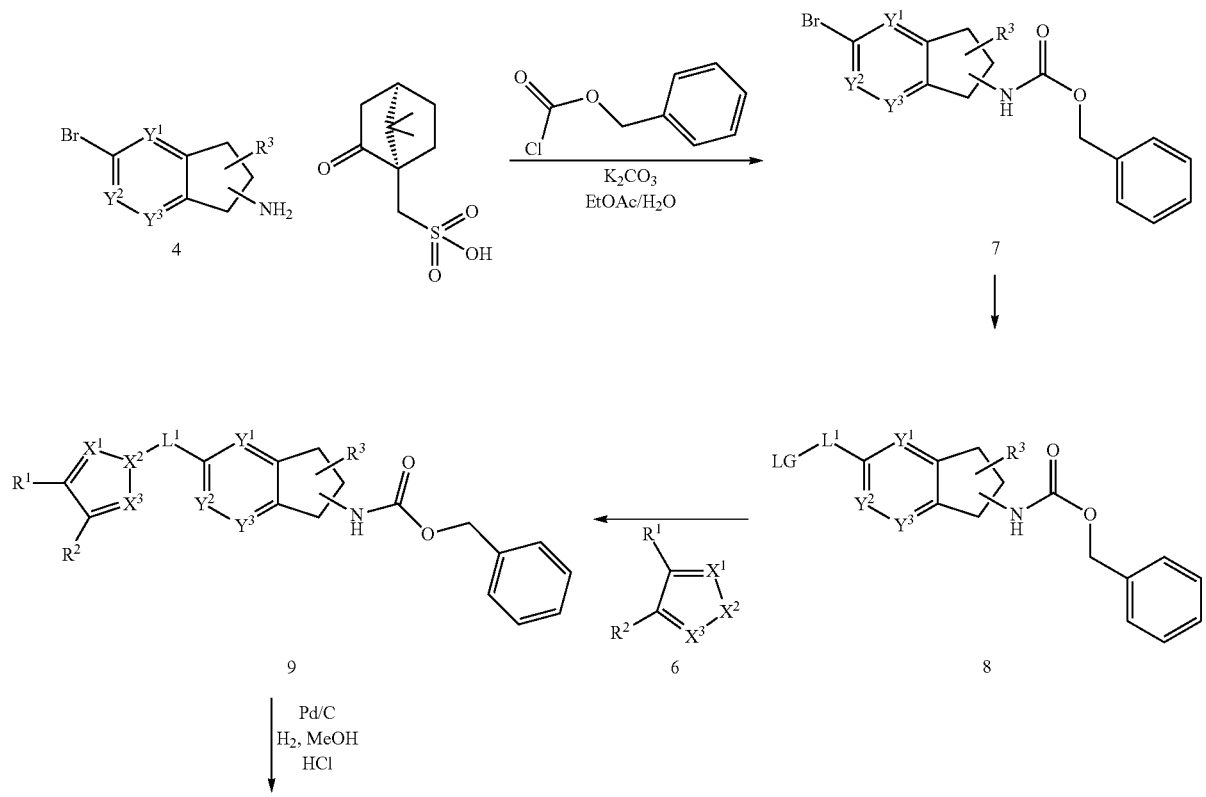

-continued

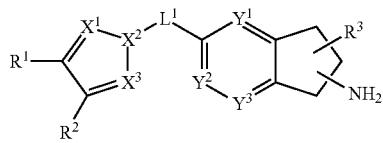

10

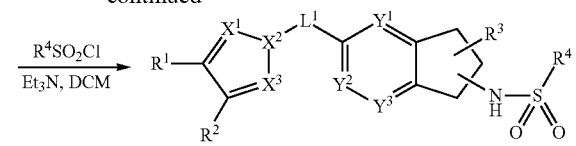

11

Addition of a suitable protecting group to arylcycloalkylamine derivatives such as (4) provides the carbamate (7). This can then be subsequently functionalised to provide the desired $L^1$-LG group by analogous methods to those described above in Scheme 1. Reaction with a suitably functionalised heterocycle (6), again in the manner described above in Scheme 1, provides the adduct (9). Removal of the protecting group by, for example hydrogenation, yields the free amine (10), which can subsequently be sulfonylated in the presence of base, such as triethylamine, to afford the desired product (11).

The present invention also includes within its scope all stereoisomeric forms of heterocyclic derivatives according to the present invention resulting, for example, because of configurational or geometrical isomerism. Such stereoisomeric forms are enantiomers, diastereoisomers, cis and trans isomers etc. For example, in the case where $R^2$ is 1-hydroxyethyl the compound exists as a pair of enantiomers. In the case where $R^3$ is methyl both cis and trans geometric isomers are possible. In the case of the individual stereoisomers of heterocyclic derivatives of formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The heterocyclic derivatives of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The heterocyclic derivatives of the present invention also exist as amorphous forms. Multiple crystalline forms are also possible. All these physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically-labelled compounds of the compounds described and claimed herein which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I can generally be prepared by following procedures analogous to those disclosed in the Schemes and/or in the Examples hereinbelow, by substituting an appropriate isotopically labelled reagent for a non-isotopically labelled reagent.

Prodrugs of the compounds of the invention are also contemplated within the scope of the invention. A prodrug is a compound which acts as a drug precursor which, upon administration to a subject, undergoes conversion by metabolic or other chemical processes to yield a heterocyclic derivative of formula I or a solvate or salt thereof. For example, where $R^2$ is hydroxymethyl the hydroxyl group may be capped as, for example, an ester or a carbamate, which upon administration to a subject will undergo conversion back to the free hydroxyl group. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In a further aspect, the heterocyclic derivatives of the present invention and their pharmaceutically acceptable salts and solvates are useful in therapy. As such the heterocyclic derivatives of the present invention are useful for the manufacture of a medicament for the treatment or prevention of psychiatric diseases where an enhancement of synaptic responses mediated by AMPA receptors is required. In particular the heterocyclic derivatives are useful for the manufacture of a medicament for the treatment of neurodegenerative disorders, cognitive or memory dysfunction, memory and learning disorders, attention disorder, trauma, stroke, epilepsy, Alzheimer's disease, depression, schizophrenia, psychotic disorders, anxiety, autism, a disorder or disease resulting from neurotic agents, substance abuse, alcohol psychiatric disorders, Parkinson's Disease, sleep disorders or narcolepsy or other conditions resulting from sleep deprivation. The present invention further includes a heterocyclic derivative for use in the treatment of any of the aforementioned diseases or disorders.

In a further embodiment of the present invention is a heterocyclic derivative for use in the treatment of neurodegenerative disorders, cognitive or memory dysfunction and memory and learning disorders. In a further embodiment of the present invention is a heterocyclic derivative for use in the treatment of Alzheimer's disease.

The present invention further includes a method for the treatment of a mammal, including a human, suffering from or liable to suffer from any of the aforementioned diseases or disorders, which comprises administering an effective amount of a heterocyclic derivative according to the present invention or a pharmaceutically acceptable salt or solvate thereof. By effective amount or therapeutically effective amount is meant an amount of compound or a composition of the present invention effective in inhibiting the above-noted diseases and thus producing the desired therapeutic, ameliorative, inhibitory or preventative effect.

The amount of a heterocyclic derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising a heterocyclic derivative according to the present invention in admixture with one or more pharmaceutically acceptable excipients, such as the ones described in Gennaro et. al., Remington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a heterocyclic derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition for the use as hereinbefore described.

The invention is further illustrated by the following examples which are not intended to limit the scope thereof. Unless otherwise indicated, percent is percent by weight given the component and the total weight of the composition, temperature is in ° C. or is at ambient temperature and pressure is at or near atmospheric. Commercial reagents were used without further purification.

EXAMPLE 1

(R)—N-(5-((4-(hydroxymethyl)-3-(trifluoromethyl)-1H-pyrazol-1-yl)methyl)-2,3-dihydro-1H-inden-2-yl)propane-2-sulfonamide a) 5-bromo-2,3-dihydro-1H-inden-2-amine hydrobromide

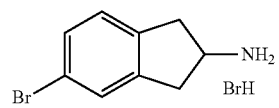 [SMILES: NC1Cc2ccc(Br)cc2C1 ; Br]

A suspension of aminoindane hydrochloride (150 mmol, 25.43 g) and water (127 mL) under N$_2$ was heated to an internal temp of 58-60° C. in an oil bath and to the resulting solution was added bromine (154 mmol, 7.93 mL, 24.67 g) dropwise over approx 40 min maintaining internal temperature around 58-60° C. The reaction mixture was stirred at 60° C. for a further 1 h then 48% HBr (22.91 mL) was added over 2 minutes and mixture stirred for 10 min. The reaction was then cooled to room temperature over 1 h and stood at room temperature overnight. The resulting solids were isolated by filtration and washed with 2-propanol (2×20 mL) to give a beige solid. This was collected by filtration and re-crystallised from hot water to give 5-bromo-2,3-dihydro-1H-inden-2-amine hydrobromide as a beige solid (20 g) A second crop was (4.5 g) was obtained in a similar way. (24.5 g, 55.8%). $^1$H NMR (400 MHz, DMSO$_{d6}$) δ 3.03 (m, 2H) 3.43 (m, 2H) 4.13 (m, 1H) 7.22 (d, 1H) 7.37 (d, 1H) 7.46 (s, 1H)

b) (R)-5-bromo-2,3-dihydro-1H-inden-2-amine((1S,4R)-7,7-dimethyl-2-oxobicyclo[2.2.1]heptan-1-yl)methanesulfonate

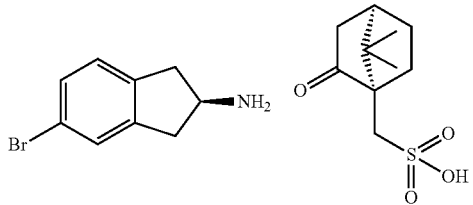

A suspension of 5-bromo-2,3-dihydro-1H-inden-2-amine hydrobromide (107 mmol, 31.38 g) and N-Methylmorpholine (112 mmol, 12.36 mL, 11.37 g) in methanol (66.9 mL) was heated to 58-62° C. and a solution of D-(+)-10-Camphorsulfonic acid (139 mmol, 32.3 g) in Methanol (53.6 mL) was added over 3 min maintaining internal temp at 60-65° C. The addition funnel was rinsed with methanol (13.26 mL) and rinsings added to reaction. The mixture was stirred at for 10 min until a clear solution was obtained. The reaction was then allowed to cool to room temperature and stirred for a total of 4 h. The solids were collected by filtration and washed with a pre-cooled mixture of isopropyl acetate/methanol 2:1 (2×15 mL) followed by water (2×15 mL). The crude product was dried in a vacuum oven at 50° C. overnight to yield (23.1 g) of a fluffy white solid. This was suspended in methanol (160 mL) and heated to reflux for 4 h then allowed to cool to room temperature with stirring over 2 h and stirring continued at room temperature for a further 1 h. Solids were then isolated by filtration and washed with a pre-cooled solution of isopropylacetate/methanol (2:1, 2×18 mL). The colourless solid (15.51 g) was dried in the vacuum oven for 60 h. Refluxing in methanol followed by washing the solid with isopropyl acetate/methanol was repeated until the desired enantiomeric ratio was obtained. (R)-5-bromo-2,3-dihydro-1H-inden-2-amine((1S,4R)-7,7-dimethyl-2-oxobicyclo[2.2.1]heptan-1-yl)methanesulfonate was obtained as a colourless solid (13.83 g, e.e. 100:0, 29.1%). $^1$H NMR (400 MHz, DMSO$_{d6}$) δ 0.72 (s, 3H) 1.04 (s, 3H) 1.28 (m, 2H) 1.80 (m, 2H) 1.94 (m, 1H) 2.25 (m, 1H) 2.38 (m, 1H) 2.69 (m, 1H) 2.83-2.95 (m, 3H) 3.25 (m, integration masked water peak) 4.02 (m, 1H) 7.25 (d, 1H) 7.39 (d, 1H) 7.50 (s, 1H) 8.00 (bs, 3H)

c) (R)—N-(5-bromo-2,3-dihydro-1H-inden-2-yl)propane-2-sulfonamide

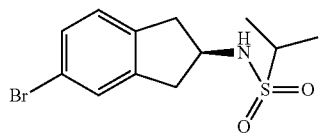 [SMILES: CC(C)S(=O)(=O)N[C@@H]1Cc2ccc(Br)cc2C1]

(R)-5-bromo-2,3-dihydro-1H-inden-2-amine((1S,4R)-7,7-dimethyl-2-oxobicyclo[2.2.1]heptan-1-yl)methanesulfonate (7.88 mmol, 3.5 g) was suspended in DCM (40 mL) and DBU (23.63 mmol, 3.53 mL, 3.60 g) was added. The mixture was purged with nitrogen and cooled in an ice bath before dropwise addition of propane-2-sulfonyl chloride (15.75 mmol, 1.760 mL, 2.246 g). Stirring was continued at 0° C. for 1 h before allowing to come to room temperature. The mixture was diluted with DCM (100 mL) and 1N HCl (100 mL) and the phases mixed and separated. The aqueous phase was further extracted with DCM (2×100 mL) before combined organics were washed with brine. Concentration gave a light yellow oil which was purified on silica eluting with 75% DCM/heptane then neat DCM. Desired fractions were collected and concentrated to give (R)—N-(5-bromo-2,3-dihydro-1H-inden-2-yl)propane-2-sulfonamide as a colourless oil (2.18 g, 87%). $^1$H NMR (400 MHz, CDCl$_3$) δ 1.39 (d, 6H) 2.88 (m, 2H) 3.17 (sept, 1H) 3.28 (m, 2H) 4.27 (m, 2H) 7.08 (d, 1H) 7.30 (d, 1H) 7.35 (s, 1H)

d) (R)-methyl 2-(1-methylethylsulfonamido)-2,3-dihydro-1H-indene-5-carboxylate

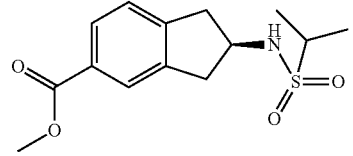 [SMILES: COC(=O)c1ccc2c(c1)C[C@H](NS(=O)(=O)C(C)C)C2]

(R)—N-(5-bromo-2,3-dihydro-1H-inden-2-yl)propane-2-sulfonamide, (3.77 mmol, 1.2 g) DBU (5.66 mmol, 0.861 g, 0.846 mL), acetoxy(2-(dio-tolylphosphino)benzyl)palladium (0.377 mmol, 0.354 g), tri-tert-butylphosphine tetrafluoroborate (0.754 mmol, 0.219 g) and molybdenum hexacarbonyl (3.77 mmol, 0.995 g) were added to a Smith Creator microwave vial and heated at 150° C. for 30 min. The mixture was concentrated before dissolving in dichloromethane and filtration through a celite plug. Purification was achieved on silica eluting with DCM to give (R)-methyl 2-(1-methylethylsulfonamido)-2,3-dihydro-1H-indene-5-carboxylate as a brown oil (1.15 g, 103%). $^1$H NMR (400 MHz, CDCl$_3$) δ 1.40 (d, 6H) 2.95 (d, 2H) 3.18 (sept, 1H) 3.36 (m, 2H) 3.90 (s, 3H) 4.3 (m, 2H) 7.27 (d, 1H) 7.89 (m, 2H)

e) (R)—N-(5-(hydroxymethyl)-2,3-dihydro-1H-inden-2-yl)propane-2-sulfonamide

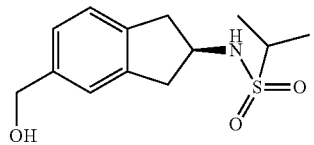 [SMILES: CC(C)S(=O)(=O)N[C@@H]1Cc2ccc(CO)cc2C1]

(R)-methyl-2-(1-methylethylsulfonamido)-2,3-dihydro-1H-indene-5-carboxylate (7.13 mmol, 2.12 g) was dissolved in dry THF (100 mL) and the vessel purged with nitrogen. Lithium aluminium hydride (1M, 14.3 mmol, 14.3 mL) was added dropwise and stirring continued for 20 min. The mixture was quenched by addition of methanol followed by water and 1N HCl before concentration to remove organics. The residue was partitioned between EtOAc/1N HCl. and the phases mixed and separated. The aqueous layer was further extracted with EtOAc (×2) Combined organics washed with brine and concentrated before purification on silica eluting with 1% MeOH/DCM to give (R)—N-(5-(hydroxymethyl)-2,3-dihydro-1H-inden-2-yl)propane-2-sulfonamide as a light coloured solid (1.76 g, 92%). $^1$H NMR (400 MHz, CDCl$_3$) δ 1.40 (d, 6H) 1.60 (bs, 1H) 2.90 (m, 2H) 3.18 (sept, 1H) 3.32 (m, 2H) 4.19-4.33 (m, 2H) 4.66 (s, 2H) 7.20 (m, 2H) 7.26 (m, 1H)

f) (R)-ethyl-1-((2-(1-methylethylsulfonamido)-2,3-dihydro-1H-inden-5-yl)methyl)-3-(trifluoromethyl)-1H-pyrazole-4-carboxylate

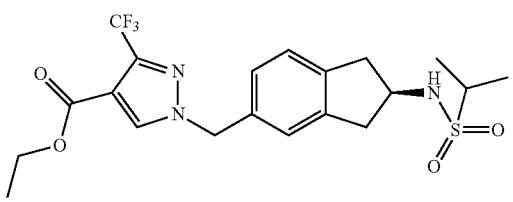 [SMILES: CCOC(=O)c1cn(Cc2ccc3c(c2)C[C@H](NS(=O)(=O)C(C)C)C3)nc1C(F)(F)F]

(R)—N-(5-(hydroxymethyl)-2,3-dihydro-1H-inden-2-yl)propane-2-sulfonamide (2.82 mmol, 760 mg) was dissolved in DCM (20 mL) and Thionyl Chloride (5.64 mmol, 0.409 mL, 671 mg) added and the solution stirred at room temperature. After 45 min the mixture was concentrated then azeotroped with DCM (4×10 mL) to give a yellow oil. To this oil was added DMF (10 mL) and potassium carbonate (8.46 mmol, 1170 mg) followed by ethyl 3-(trifluoromethyl)-1H-pyrazole-4-carboxylate (2.82 mmol, 587 mg). The mixture was heated to 60° C. with stirring for 1 h. The reaction was concentrated to remove DMF before partitioning between EtOAc/Water. The phases were mixed and separated and the aqueous phase further washed with EtOAc (×2). Combined organics were dried and concentrated to give a light yellow oil which was purified on silica eluting with 25% EtOAc/heptane. Desired fractions were collected and concentrated to give (R)-ethyl 1-((2-(1-methylethylsulfonamido)-2,3-dihydro-1H-inden-5-yl)methyl)-3-(trifluoromethyl)-1H-pyrazole-4-carboxylate as a colourless solid (1.11 g, 86%).

$^1$H NMR (400 MHz, CDCl$_3$) δ 1.31 (t, 3H) 1.39 (d, 6H) 2.9 (m, 2H) 3.17 (sept, 1H) 3.30 (m, 2H) 4.30 (m, 4H) 5.28 (s, 2H) 7.13 (m, 2H) 7.25 (d, 1H) 7.89 (s, 1H)

g) (R)—N-(5-((4-(hydroxymethyl)-3-(trifluoromethyl)-1H-pyrazol-1-yl)methyl)-2,3-dihydro-1H-inden-2-yl)propane-2-sulfonamide

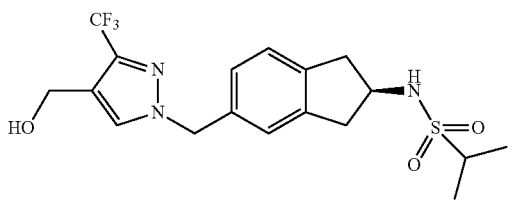 [SMILES: CC(C)S(=O)(=O)N[C@@H]1Cc2ccc(Cn3cc(CO)c(C(F)(F)F)n3)cc2C1]

(R)-ethyl-1-((2-(1-methylethylsulfonamido)-2,3-dihydro-1H-inden-5-yl)methyl)-3-(trifluoromethyl)-1H-pyrazole-4-carboxylate (2.416 mmol, 1.11 g) was dissolved in THF (20 mL) and the vessel purged with nitrogen. Lithium aluminium hydride (1M, 4.83 mmol, 4.83 mL) was added dropwise and the mixture stirred at room temperature for 1 h. The reaction was quenched by addition of MeOH followed by water before concentration. The residue was partitioned between 1N HCl and EtOAc and the organic phase collected. The aqueous phase was further extracted with EtOAc (×2). Combined organics were dried and concentrated before purification on silica eluting with 30% EtOAc/iso-hexane followed by 50% EtOAc/iso-hexane. Desired fractions were collected and concentrated to give (R)—N-(5-((4-(hydroxymethyl)-3-(trifluoromethyl)-1H-pyrazol-1-yl)methyl)-2,3-dihydro-1H-inden-2-yl)propane-2-sulfonamide as a colourless glass (0.690 g, 68.5%). MS (ESI): m/z [M+Na]$^+$ 440.5

EXAMPLE 2

(S)—N-(5-((4-(hydroxymethyl)-3-(trifluoromethyl)-1H-pyrazol-1-yl)methyl)-2,3-dihydro-1H-inden-2-yl)propane-2-sulfonamide

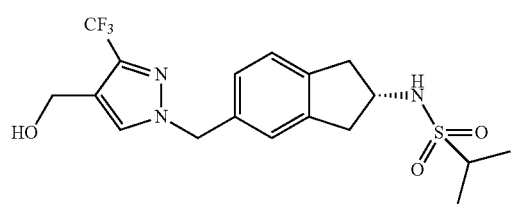 [SMILES: CC(C)S(=O)(=O)N[C@H]1Cc2ccc(Cn3cc(CO)c(C(F)(F)F)n3)cc2C1]

a) (S)-5-bromo-2,3-dihydro-1H-inden-2-amine((1R,4S)-7,7-dimethyl-2-oxobicyclo[2.2.1]heptan-1-yl)methanesulfonate

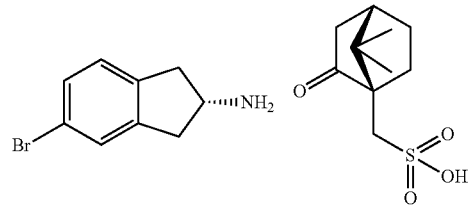

To a suspension of 5-bromo-2,3-dihydro-1H-inden-2-amine hydrobromide (107 mmol, 31.27 g) and N-methylmorpholine (112 mmol, 12.32 mL, 11.33 g) in methanol (66.6 mL) was heated to 58-62° C. and a solution of ((1R,4S)-7,7-dimethyl-2-oxobicyclo[2.2.1]heptan-1-yl)methanesulfonic acid (107 mmol, 24.79 g) in methanol (53.4 mL) was added over 3 min maintaining internal temp at 60-65° C. The addition funnel was rinsed with MeOH (13.3 mL) and rinsings added to reaction. The mixture was stirred at 60-65° C. for 10 min until a clear solution was obtained. The reaction was then allowed to cool to room temperature and stirred for a total of 4 h. The solids were collected by filtration and washed with a pre-cooled mixture of isopropyl acetate/methanol 2:1 (2×15 mL) followed by water (2×15 mL). The crude product was dried in a vacuum oven at 50° C. overnight to yield (18.03 g) of a fluffy white solid. This was suspended in methanol (130 mL) and heated to reflux for 4 h then allowed to cool to room temperature with stirring over 2 h and stirring continued at room temperature for a further 1 h. Solids were then isolated by filtration and washed with a pre-cooled solution of isopropylacetate/methanol (2:1, 2×18 mL). The colourless solid (13.82 g) was dried in the vacuum oven for 60 h. Refluxing in methanol followed by washing the solid with isopropyl acetate/methanol was repeated until the desired enantiomeric ratio was obtained. (S)-5-bromo-2,3-dihydro-1H-inden-2- amine((1S,4R)-7,7-dimethyl-2-oxobicyclo[2.2.1]heptan-1-yl)methanesulfonate was obtained as a colourless solid (12.28 g, e.e. 100:0, 25.9%).

¹H NMR (400 MHz, DMSO$_{d6}$) δ 0.74 (s, 3H) 1.05 (s, 3H) 1.28 (m, 2H) 1.80 (m, 2H) 1.94 (m, 1H) 2.25 (m, 1H) 2.38 (m, 1H) 2.69 (m, 1H) 2.83-2.95 (m, 3H) 3.25 (m, integration masked water peak) 4.02 (m, 1H) 7.25 (d, 1H) 7.39 (d, 1H) 7.50 (s, 1H) 8.00 (bs, 3H)

b) (S)—N-(5-bromo-2,3-dihydro-1H-inden-2-yl)propane-2-sulfonamide

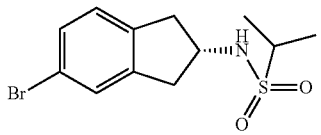 [SMILES: CC(C)S(=O)(=O)N[C@H]1Cc2ccc(Br)cc2C1]

(S)-5-bromo-2,3-dihydro-1H-inden-2-amine((1R,4S)-7,7-dimethyl-2-oxobicyclo[2.2.1]heptan-1-yl)methanesulfonate (3.38 mmol, 1.5 g) was suspended in dichloromethane (20 mL) and DBU (10.13 mmol, 1.513 mL, 1.542 g) added. The mixture was purged with nitrogen and cooled in an ice bath before drop-wise addition of propane-2-sulfonyl chloride (6.75 mmol, 0.754 mL, 0.963 g). Stirring was continued at 0° C. for 1 h before allowing to come to room temperature. The mixture was diluted with DCM (100 mL) and 1N HCl (100 mL) and the phases mixed and separated. The aqueous phase was further extracted with DCM (2×100 mL) before combined organics were washed with brine. Concentration gave ~1.5 g of a light yellow oil which was purified on 20 g Si eluting with 75% Dichloromethane/Heptane then neat DCM. Desired fractions were collected and concentrated to give (S)—N-(5-bromo-2,3-dihydro-1H-inden-2-yl)propane-2-sulfonamide as a colourless oil (1.0 g, 93%). ¹H NMR (400 MHz, CDCl₃) δ 1.39 (d, 6H) 2.88 (m, 2H) 3.18 (sept, 1H) 3.28 (m, 2H) 4.27 (m, 1H) 4.40 (m, 1H) 7.08 (d, 1H) 7.30 (d, 1H) 7.35 (s, 1H)

c) (S)-methyl 2-(1-methylethylsulfonamido)-2,3-dihydro-1H-indene-5-carboxylate

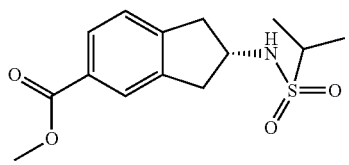 [SMILES: COC(=O)c1ccc2c(c1)C[C@@H](NS(=O)(=O)C(C)C)C2]

(S)—N-(5-bromo-2,3-dihydro-1H-inden-2-yl)propane-2-sulfonamide, (1.25 mmol, 0.4 g), DBU (1.88 mmol, 0.281 mL, 0.286 g), acetoxy(2-(dio-tolylphosphino)benzyl)palladium (0.125 mmol, 0.118 g), tri-tert-butylphosphine tetrafluoroborate (0.251 mmol, 0.072 g) and molybdenum hexacarbonyl (1.25 mmol, 0.331 g) were added to a Smith Creator microwave vial and heated at 150° C. for 30 min. The mixture was concentrated before dissolving in dichloromethane and filtration through a dicalite plug. Purification was achieved on silica eluting with DCM to give (S)-methyl 2-(1-methylethylsulfonamido)-2,3-dihydro-1H-indene-5-carboxylate as a brown oil (0.327 g, 88%). ¹H NMR (400 MHz, CDCl₃) δ 1.38 (d, 6H) 2.95 (d, 2H) 3.18 (sept, 1H) 3.36 (m, 2H) 3.90 (s, 3H) 4.3 (m, 2H) 7.26 (d, 1H) 7.87 (m, 2H)

d) (S)—N-(5-(hydroxymethyl)-2,3-dihydro-1H-inden-2-yl)propane-2-sulfonamide

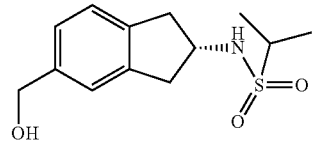 [SMILES: CC(C)S(=O)(=O)N[C@H]1Cc2ccc(CO)cc2C1]

(S)-methyl-2-(1-methylethylsulfonamido)-2,3-dihydro-1H-indene-5-carboxylate (2.502 mmol, 744 mg) was dissolved in dry THF (20 mL) and was purged with nitrogen and cooled in an ice bath. Lithium aluminium hydride (7.51 mmol, 7.51 mL) was added dropwise and stirring continued at 0° C. for 10 min. The mixture was quenched by addition of methanol followed by 1:1 THF/water and 1N HCl before concentration to remove organics. The residue was partitioned between dichlormethane/1N HCl. and the phases mixed and separated. The aqueous layer was further extracted with DCM (×2) Combined organics washed with brine and concentrated before purification on silica eluting with 2% MeOH/DCM to give (S)—N-(5-(hydroxymethyl)-2,3-dihydro-1H-inden-2-yl)propane-2-sulfonamide (0.692 g, 103%). ¹H NMR (400 MHz, CDCl₃) δ 1.39 (d, 6H) 1.71 (bt, 1H) 2.89 (m, 2H) 3.18 (sept, 1H) 3.30 (m, 2H) 4.28 (m, 1H) 4.41 (m, 1H) 4.66 (d, 2H) 7.18 (m, 2H) 7.24 (m, 1H)

e) (S)-ethyl 1-((2-(1-methylethylsulfonamido)-2,3-dihydro-1H-inden-5-yl)methyl)-3-(trifluoromethyl)-1H-pyrazole-4-carboxylate

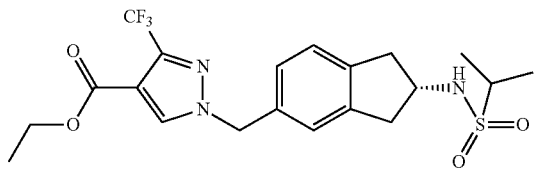 [SMILES: CCOC(=O)c1cn(Cc2ccc3c(c2)C[C@@H](NS(=O)(=O)C(C)C)C3)nc1C(F)(F)F]

(S)—N-(5-(hydroxymethyl)-2,3-dihydro-1H-inden-2-yl)propane-2-sulfonamide (2.57 mmol, 692 mg) was dissolved in DCM (10 mL), thionyl chloride (5.14 mmol, 0.373 mL, 611 mg) added and the solution stirred at room temperature. After 45 min the mixture was concentrated then azeotroped with dichloromethane (4×10 mL) to give a yellow oil. To this oil was added dimethylformamide (10 mL) and potassium carbonate (7.71 mmol, 1.07 g) followed by ethyl 3-(trifluoromethyl)-1H-pyrazole-4-carboxylate (2.57 mmol, 0.54 g). The mixture was heated to 70° C. with stirring for 1 h. The reaction was concentrated to remove DMF before partitioning between EtOAc/water. The phases were mixed and separated and the aqueous phase further washed with EtOAc (×2). Combined organics were dried and concentrated to give a light yellow oil which was purified on silica eluting with 30% EtOAc/heptane. Desired fractions were collected and concentrated to give (S)-ethyl-1-((2-(1-methylethylsulfonamido)-2,3-dihydro-1H-inden-5-yl)methyl)-3-(trifluoromethyl)-1H-pyrazole-4-carboxylate as a colourless solid (0.65 g, 55.1%). ¹H NMR (400 MHz, CDCl₃) δ 1.33 (t, 3H) 1.39 (d, 6H) 2.9 (m, 2H) 3.17 (sept, 1H) 3.30 (m, 2H) 4.30 (m, 4H) 5.29 (s, 2H) 7.12 (m, 2H) 7.24 (d, 1H) 7.89 (s, 1H)

f) (S)—N-(5-((4-(hydroxymethyl)-3-(trifluoromethyl)-1H-pyrazol-1-yl)methyl)-2,3-dihydro-1H-inden-2-yl)propane-2-sulfonamide

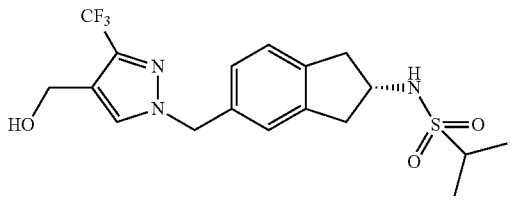 [SMILES: CC(C)S(=O)(=O)N[C@H]1Cc2ccc(Cn3cc(CO)c(C(F)(F)F)n3)cc2C1]

(S)-ethyl-1-((2-(1-methylethylsulfonamido)-2,3-dihydro-1H-inden-5-yl)methyl)-3-(trifluoromethyl)-1H-pyrazole-4-carboxylate (1.371 mmol, 630 mg) was dissolved in tetrahydrofuran (10 mL) and the vessel purged with nitrogen. Lithium aluminium hydride (1M, 1.371 mmol, 1.371 mL) was added dropwise and the mixture stirred at room temperature for 20 min. An additional quantity of lithium aluminium hydride (1M, 1.371 mmol, 1.371 mL) was added to complete the reaction. The reaction was quenched by addition of methanol followed by water before concentration. The residue was partitioned between 1N HCl and Ethylacetate and the organic phase collected. The aqueous phase was further extracted with EtOAc (×2). Combined organics were dried and concentrated before purification on silica eluting with 2% MeOH/DCM. Desired fractions were collected and concentrated to give (S)—N-(5-((4-(hydroxymethyl)-3-(trifluoromethyl)-1H-pyrazol-1-yl)methyl)-2,3-dihydro-1H-inden-2-yl)propane-2-sulfonamide as a colourless glass. (0.505 g, 88%) MS (ESI): m/z [M+H]$^+$ 418.5

EXAMPLE 3

(R)-1,1,1-trifluoro-N-(5-((4-(hydroxymethyl)-3-(trifluoromethyl)-1H-pyrazol-1-yl)methyl)-2,3-dihydro-1H-inden-2-yl)methanesulfonamide a) (R)-benzyl 5-bromo-2,3-dihydro-1H-inden-2-ylcarbamate

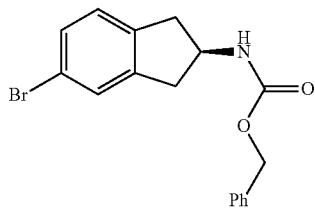 [SMILES: O=C(N[C@@H]1Cc2ccc(Br)cc2C1)OCc1ccccc1]

(R)-5-bromo-2,3-dihydro-1H-inden-2-amine((1S,4R)-7,7-dimethyl-2-oxobicyclo[2.2.1]heptan-1-yl)methanesulfonate (12.56 mmol, 5.58 g) was dissolved in EtOAc (30 mL)/water (30 mL) and potassium carbonate (37.7 mmol, 5.21 g) added. The mixture was cooled in an ice bath and benzyl chloroformate (13.81 mmol, 1.964 mL, 2.356 g) added dropwise. Stirring was continued overnight during which time the reaction came to room temperature. The crude reaction mixture was diluted with water and ethylacetate and the phases mixed and separated. The aqueous layer was further extracted with EtOAc (×2). Combined organics were dried and concentrated before crystallisation of the product from ethylacetate/heptane mixture to give (R)-benzyl 5-bromo-2,3-dihydro-1H-inden-2-ylcarbamate as colourless needles (3.89 g, 89%). $^1$H NMR (400 MHz, CDCl$_3$) δ 2.79 (m, 2H) 3.26 (m, 2H) 4.53 (bm, 1H) 4.93 (bm, 1H) 5.10 (bs, 2H) 7.07 (m, 1H) 7.26-7.37 (m, 7H)

b) (R)-methyl 2-(benzyloxycarbonylamino)-2,3-dihydro-1H-indene-5-carboxylate

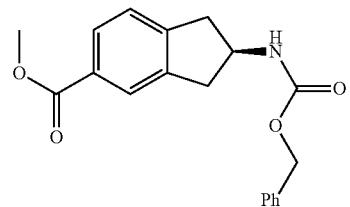 [SMILES: COC(=O)c1ccc2c(c1)C[C@H](NC(=O)OCc1ccccc1)C2]

(R)-benzyl-5-bromo-2,3-dihydro-1H-inden-2-ylcarbamate (11.24 mmol, 3.89 g), DBU (16.85 mmol, 2.52 mL, 2.57 g), acetoxy(2-(dio-tolylphosphino)benzyl)palladium (1.12 mmol, 1.05 g), tri-tert-butylphosphine tetrafluoroborate (2.25 mmol, 0.652 g) and molybdenum hexacarbonyl (11.24 mmol, 2.97 g) were added to a Smith Creator microwave vial and heated at 150° C. for 30 min. The crude reaction was filtered through a cotton wool pad and the residue washed with MeOH. Concentration gave a dark oil which was purified on 340 g Si eluting with 0-1% Methanol/dichloromethane to give (R)-methyl 2-(benzyloxycarbonylamino)-2,3-dihydro-1H-indene-5-carboxylate (3.24 g, 89%) as a brown oil. $^1$H NMR (400 MHz, CDCl$_3$) δ 2.85 (m, 2H) 3.32 (m, 2H) 3.89 (s, 3H) 4.54 (bs, 1H) 4.95 (bs, 1H) 5.10 (bs, 2H) 7.25-7.41 (bm, 6H)

c) (R)-benzyl 5-(hydroxymethyl)-2,3-dihydro-1H-inden-2-ylcarbamate

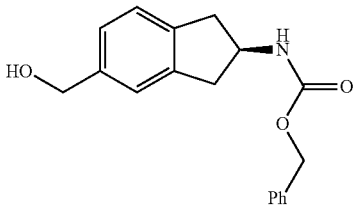 [SMILES: O=C(N[C@@H]1Cc2ccc(CO)cc2C1)OCc1ccccc1]

(R)-methyl-2-(benzyloxycarbonylamino)-2,3-dihydro-1H-indene-5-carboxylate (9.96 mmol, 3.24 g) was dissolved in tetrahydrofuran (50 mL) and the vessel purged with nitrogen. Lithium borohydride (1.2M, 19.92 mmol, 9.96 mL) was added dropwise followed by methanol (19.92 mmol, 0.807 mL, 0.638 g). The solution was stirred at room temperature overnight before additional lithium borohydride (1.2M, 19.92 mmol, 9.96 mL) was added. Stirring was continued for 5 h. The reaction was quenched with methanol then water and concentrated to a light brown residue. This was partitioned between EtOAc (150 mL) and 1N HCl (150 mL) and the phases mixed and separated. The aqueous layer was twice extracted with ethylacetate and combined organics dried, filtered and concentrated to give ~3 g of a light brown oil which was purified on silica eluting with 0-0.5% MeOH/DCM to give (R)-benzyl 5-(hydroxymethyl)-2,3-dihydro-1H-inden-2-ylcarbamate as an off white solid (1.51 g, 51%). $^1$H NMR (400 MHz, CDCl$_3$) δ 1.66 (t, 1H) 2.81 (m, 2H) 3.28 (m, 2H) 4.52 (bs, 1H) 4.65 (d, 2H) 4.95 (bs, 1H) 5.09 (bs, 2H) 7.15-7.37 (bm, 8H)

d) (R)-benzyl-5-((4-(hydroxymethyl)-3-(trifluoromethyl)-1H-pyrazol-1-yl)methyl)-2,3-dihydro-1H-inden-2-ylcarbamate

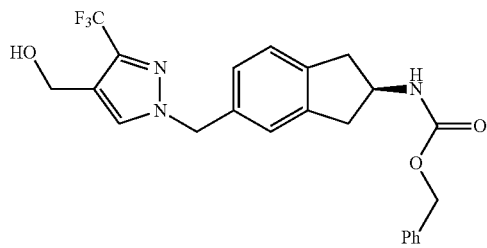 [SMILES: O=C(N[C@@H]1Cc2ccc(Cn3cc(CO)c(C(F)(F)F)n3)cc2C1)OCc1ccccc1]

(R)-benzyl-5-(hydroxymethyl)-2,3-dihydro-1H-inden-2-ylcarbamate (5.08 mmol, 1.51 g) was dissolved in DCM (20 mL), thionyl chloride (10.16 mmol, 0.741 mL, 1.208 g) added and the resultant solution stirred at room temperature for 45 min. The sample was concentrated and azeotroped with DCM (×4). Potassium carbonate (15.23 mmol, 2.105 g) was added followed by DMF (20 mL) and (3-(trifluoromethyl)-1H-pyrazol-4-yl)methanol (5.08 mmol, 0.843 g) and the mixture heated to 60° C. for 1 h. The mixture was concentrated and partitioned between EtOAc/water. The aqueous layer was twice extracted with EtOAc and combined organics dried, filtered and concentrated to give a yellow oil which was purified on silica eluting with 0.5% MeOH/DCM to give (R)-benzyl 5-((4-(hydroxymethyl)-3-(trifluoromethyl)-1H-pyrazol-1-yl)methyl)-2,3-dihydro-1H-inden-2-ylcarbamate as a light coloured oil (1.74 g, 77%). $^1$H NMR (400 MHz, CDCl$_3$) δ 1.83 (t, 1H) 2.79 (m, 2H) 3.27 (m, 2H) 4.52 (bs, 1H) 4.64 (d, 2H) 4.99 (bs, 1H) 5.09 (bs, 2H) 5.25 (s, 2H) 7.05-7.11 (m, 2H) 7.19 (m, 1H) 7.26-7.40 (m, 6H).

e) (R)-(1-((2-amino-2,3-dihydro-1H-inden-5-yl)methyl)-3-(trifluoromethyl)-1H-pyrazol-4-yl)methanol

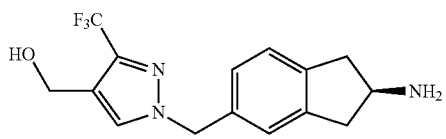 [SMILES: N[C@@H]1Cc2ccc(Cn3cc(CO)c(C(F)(F)F)n3)cc2C1]

Palladium hydroxide (20% on carbon) (3.86 mmol, 0.542 g) was wetted in a hydrogenation vessel before addition of (R)-benzyl-5-((4-(hydroxymethyl)-3-(trifluoromethyl)-1H-pyrazol-1-yl)methyl)-2,3-dihydro-1H-inden-2-ylcarbamate (3.86 mmol, 1.72 g) and ethanol (50 mL) followed by aqueous 5N HCl solution (5.00 mL). The mixture was stirred under 2 bar of hydrogen for 35 min before diluting with DCM (100 mL) and filtration through a dicalite pad which was then washed with 10% MeOH/DCM (150 mL). Combined organics were concentrated and partitioned between ethylacetate and saturated sodium carbonate solution. The organic layer was concentrated to give (R)-(1-((2-amino-2,3-dihydro-1H-inden-5-yl)methyl)-3-(trifluoromethyl)-1H-pyrazol-4-yl)methanol (0.85 g, 70.7%). $^1$H NMR (400 MHz, CDCl$_3$) δ 2.65 (m, 2H) 3.15 (m, 2H) 3.83 (m, 1H) 4.61 (s, 2H) 5.24 (s, 2H) 7.06 (d, 1H) 7.11 (s, 1H) 7.19 (d, 1H) 7.38 (s, 1H).

f) (R)-1,1,1-trifluoro-N-(5-((4-(hydroxymethyl)-3-(trifluoromethyl)-1H-pyrazol-1-yl)methyl)-2,3-dihydro-1H-inden-2-yl)methanesulfonamide

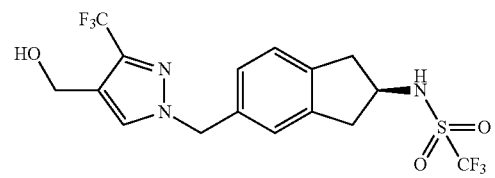 [SMILES: O=S(=O)(N[C@@H]1Cc2ccc(Cn3cc(CO)c(C(F)(F)F)n3)cc2C1)C(F)(F)F]

(R)-(1-((2-amino-2,3-dihydro-1H-inden-5-yl)methyl)-3-(trifluoromethyl)-1H-pyrazol-4-yl)methanol (0.150 mmol, 46.6 mg) was suspended in dichlormethane (2 mL) before addition of triethylamine (0.299 mmol, 0.042 mL, 30.3 mg) then trifluoromethanesulfonic anhydride (0.150 mmol, 0.025 mL, 42.2 mg) as a solution in dichloromethane (500 μL). The reaction was stirred for 60 h before the mixture was diluted with 0.5N HCl (3 mL) and DCM (3 mL). The phases mixed and separated using a hydrophobic frit and the organic layer concentrated to give a brown residue which was dissolved in DMSO (1 mL) and purified on acidic preparative HPLC to give (R)-1,1,1-trifluoro-N-(5-((4-(hydroxymethyl)-3-(trifluoromethyl)-1H-pyrazol-1-yl)methyl)-2,3-dihydro-1H-inden-2-yl)methanesulfonamide (19.3 mg, 0.044 mmol, 21.9%). $^1$H NMR (400 MHz, CDCl$_3$) δ 2.92 (m, 2H) 3.32 (m, 2H) 4.48 (m, 1H) 4.65 (s, 2H) 5.26 (m, 3H) 7.12 (m, 2H) 7.24 (d, 1H) 7.42 (s, 1H).

EXAMPLE 4

(R)—N-(5-((4-(hydroxymethyl)-3-(trifluoromethyl)-1H-pyrazol-1-yl)methyl)-2,3-dihydro-1H-inden-2-yl)methanesulfonamide

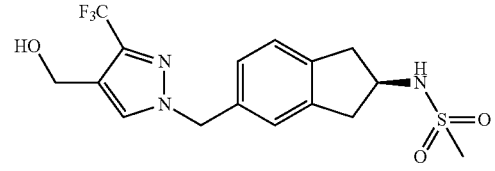 [SMILES: CS(=O)(=O)N[C@@H]1Cc2ccc(Cn3cc(CO)c(C(F)(F)F)n3)cc2C1]

(R)-(1-((2-amino-2,3-dihydro-1H-inden-5-yl)methyl)-3-(trifluoromethyl)-1H-pyrazol-4-yl)methanol (0.16 mmol, 50 mg), prepared as in Example 3 (step e) above was dissolved in tetrahydrofuran (2 mL) and triethylamine (0.299 mmol, 42 μL, 30 mg) followed by methanesulfonyl chloride (0.16 mmol, 18.4 mg) and the solution stirred at room temperature overnight. The reaction was concentrated before partitioning between dichlormethane (3 mL) and 1N HCl. (3 mL). The organic layer was collected and dried using a hydrophobic frit and concentrated under a stream of nitrogen to give a brown residue which was dissolved in DMSO (1 mL) and purified on preparative basic HPLC to give (R)—N-(5-((4-(hydroxymethyl)-3-(trifluoromethyl)-1H-pyrazol-1-yl)methyl)-2,3-dihydro-1H-inden-2-yl)methanesulfonamide (18.3 mg, 0.047 mmol, 29.2%) MS (ESI): m/z [M+H]+ 390.0

EXAMPLE 5

(R)—N-(5-((4-(hydroxymethyl)-3-(trifluoromethyl)-1H-pyrazol-1-yl)methyl)-2,3-dihydro-1H-inden-2-yl) ethanesulfonamide

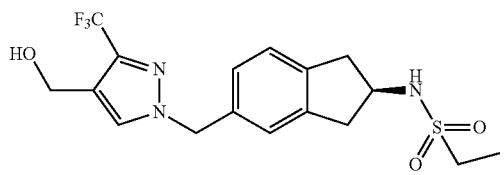 [SMILES: CCS(=O)(=O)N[C@@H]1Cc2ccc(Cn3cc(CO)c(C(F)(F)F)n3)cc2C1]

In a similar manner to Example 4, ethanesulfonylchloride was used instead of methanesulfonylchloride to yield the title compound (8.9 mg, 0.022 mmol, 13.7%). MS (ESI): m/z [M−H]− 402.0

EXAMPLE 6

(R)—N-(5-((4-(hydroxymethyl)-3-(trifluoromethyl)-1H-pyrazol-1-yl)methyl)-2,3-dihydro-1H-inden-2-yl) cyclopropanesulfonamide

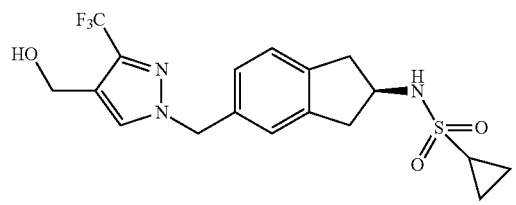 [SMILES: O=S(=O)(N[C@@H]1Cc2ccc(Cn3cc(CO)c(C(F)(F)F)n3)cc2C1)C1CC1]

In a similar manner to Example 4, cyclopropanesulfonylchloride was used instead of methanesulfonylchloride to yield the title compound (23.9 mg, 0.058 mmol, 35.7%). MS (ESI): m/z [M+Na]+ 439.0

EXAMPLE 7

(R)—N-(5-((4-(hydroxymethyl)-3-(trifluoromethyl)-1H-pyrazol-1-yl)methyl)-2,3-dihydro-1H-inden-2-yl) dimethylsulfonylurea

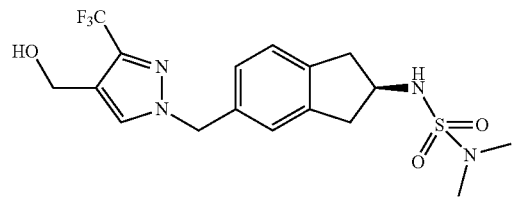 [SMILES: CN(C)S(=O)(=O)N[C@@H]1Cc2ccc(Cn3cc(CO)c(C(F)(F)F)n3)cc2C1]

In a similar manner to example 4, dimethylsulfamoylchloride was used instead of methanesulfonylchloride to yield the title compound (23.6 mg, 0.056 mmol, 35.0%). MS (ESI): m/z [M+H]+ 419.0

EXAMPLE 8

(R)—N-(5-((4-(hydroxymethyl)-3-(trifluoromethyl)-1H-pyrazol-1-yl)methyl)-2,3-dihydro-1H-inden-2-yl) furan-2-sulfonamide

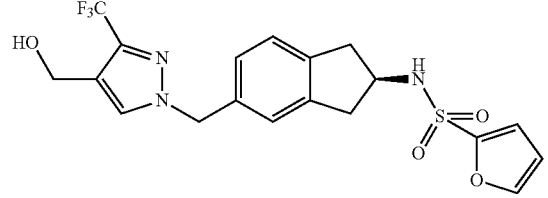 [SMILES: O=S(=O)(N[C@@H]1Cc2ccc(Cn3cc(CO)c(C(F)(F)F)n3)cc2C1)c1ccco1]

(R)-(1-((2-amino-2,3-dihydro-1H-inden-5-yl)methyl)-3-(trifluoromethyl)-1H-pyrazol-4-yl)methanol (0.08 mmol, 25 mg) was dissolved in tetrahydrofuran (1 mL) and triethylamine (0.25 mmol, 35 μL, 25 mg) followed by furan-2-sulfonyl chloride (0.084 mmol, 14.05 mg) and the solution stirred at room temperature overnight. The reaction was concentrated before partitioning between dichlormethane (3 mL) and 1N HCl. (3 mL). The organic layer was collected and dried using a hydrophobic frit and concentrated under a stream of nitrogen to give a brown residue which was dissolved in DMSO (1 mL) and purified on preparative basic HPLC to give (R)—N-(5-((4-(hydroxymethyl)-3-(trifluoromethyl)-1H-pyrazol-1-yl)methyl)-2,3-dihydro-1H-inden-2-yl)furan-2-sulfonamide (13.1 mg, 0.03 mmol, 37.1%) MS (ESI): m/z [M+H]+ 442.2

EXAMPLE 9

(R)—N-(5-((4-(hydroxymethyl)-3-(trifluoromethyl)-1H-pyrazol-1-yl)methyl)-2,3-dihydro-1H-inden-2-yl) thiophene-2-sulfonamide

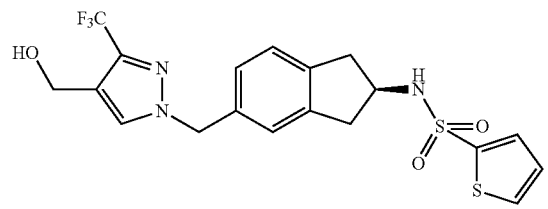 [SMILES: O=S(=O)(N[C@@H]1Cc2ccc(Cn3cc(CO)c(C(F)(F)F)n3)cc2C1)c1cccs1]

In a similar manner to example 8, thiophene-2-sulfonyl chloride was used instead of furan-2-sulfonyl chloride to yield the title compound (18.6 mg, 0.041 mmol, 50.8%). MS (ESI): m/z [M+H]+ 458.2

EXAMPLE 10

(R)—N-(5-((4-(hydroxymethyl)-3-(trifluoromethyl)-1H-pyrazol-1-yl)methyl)-2,3-dihydro-1H-inden-2-yl) thiophene-3-sulfonamide

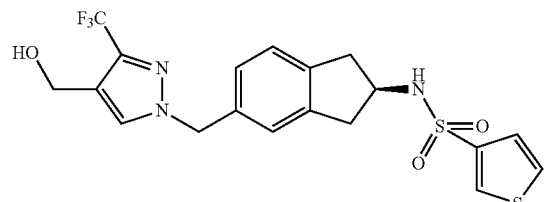

In a similar manner to example 8, thiophene-3-sulfonyl chloride was used instead of furan-2-sulfonyl chloride to yield the title compound (16.4 mg, 0.036 mmol, 44.8%). MS (ESI): m/z [M+H]+ 458.0

EXAMPLE 11

(S)-1,1,1-trifluoro-N-(5-((4-(hydroxymethyl)-3-(trifluoromethyl)-1H-pyrazol-1-yl)methyl)-2,3-dihydro-1H-inden-2-yl)methanesulfonamide a) (S)-benzyl 5-bromo-2,3-dihydro-1H-inden-2-ylcarbamate

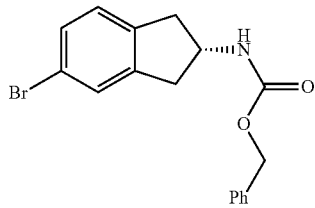 [SMILES: O=C(N[C@H]1Cc2ccc(Br)cc2C1)OCc1ccccc1]

(S)-5-bromo-2,3-dihydro-1H-inden-2-amine((1R,4S)-7,7-dimethyl-2-oxobicyclo[2.2.1]heptan-1-yl)methanesulfonate (18.47 mmol, 8.21 g) was dissolved in EtOAc (30 mL)/water (30 mL) and potassium carbonate (55.4 mmol, 7.66 g) added. The mixture was cooled in an ice bath and benzyl chloroformate (20.32 mmol, 2.89 mL, 3.47 g) added dropwise. Stirring was continued overnight during which time the reaction came to room temperature. The crude reaction mixture was diluted with water and ethylacetate and the phases mixed and separated. The aqueous layer was further extracted with EtOAc (×2). Combined organics were dried and concentrated to give (S)-benzyl 5-bromo-2,3-dihydro-1H-inden-2-ylcarbamate as a colourless solid (6.89 g, 108%). $^1$H NMR (400 MHz, CDCl$_3$) δ 2.79 (m, 2H) 3.26 (m, 2H) 4.53 (bm, 1H) 4.93 (bm, 1H) 5.10 (bs, 2H) 7.07 (m, 1H) 7.26-7.37 (m, 7H)

b) (S)-methyl 2-(benzyloxycarbonylamino)-2,3-dihydro-1H-indene-5-carboxylate

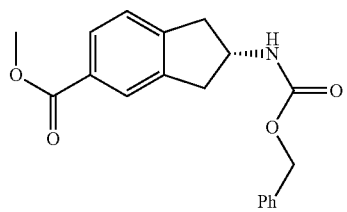 [SMILES: COC(=O)c1ccc2c(c1)C[C@@H](NC(=O)OCc1ccccc1)C2]

(S)-benzyl 5-bromo-2,3-dihydro-1H-inden-2-ylcarbamate (11.21 mmol, 3.88 g), DBU (11.21 mmol, 1.68 mL, 1.71 g), acetoxy(2-(dio-tolylphosphino)benzyl)palladium (1.12 mmol, 1.05 g), tri-tert-butylphosphine tetrafluoroborate (2.24 mmol, 0.650 g) and molybdenum hexacarbonyl (11.24 mmol, 2.96 g) were added to a Smith Creator microwave vial and heated at 150° C. for 30 min. The crude reaction was filtered through a dicalite pad and the residue washed with MeOH. Concentration gave a dark oil which was purified on silica eluting with 30% EtOAc/heptane to give (S)-methyl 2-(benzyloxycarbonylamino)-2,3-dihydro-1H-indene-5-carboxylate as a brown oil (3.4 g, 93%). $^1$H NMR (400 MHz, CDCl$_3$) δ 2.85 (m, 2H) 3.32 (m, 2H) 3.89 (s, 3H) 4.54 (bs, 1H) 4.95 (bs, 1H) 5.10 (bs, 2H) 7.25-7.41 (bm, 6H)

c) (S)-benzyl 5-(hydroxymethyl)-2,3-dihydro-1H-inden-2-ylcarbamate

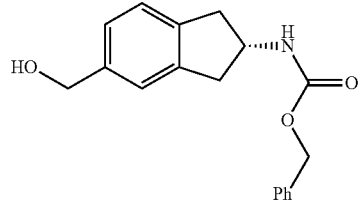 [SMILES: O=C(N[C@H]1Cc2ccc(CO)cc2C1)OCc1ccccc1]

(S)-methyl-2-(benzyloxycarbonylamino)-2,3-dihydro-1H-indene-5-carboxylate (15.37 mmol, 5.00 g) was dissolved in THF (50 mL) and the vessel purged with nitrogen. Lithium Borohydride (2M, 30.7 mmol, 15.37 mL) was added dropwise followed by methanol (30.7 mmol, 0.985 g). The solution was stirred at room temperature for 6 h before additional lithium borohydride (2M, 15.35 mmol, 7.69 mL) was added. Stirring was continued overnight. A further amount of lithium borohydride was added (2M, 15.35 mmol, 7.69 mL) and stirring continued for 1 h. The reaction was quenched with MeOH then water and concentrated to a light brown residue. This was partitioned between EtOAc (150 mL) and 1N HCl (150 mL) and the phases mixed and separated. The aqueous layer was twice extracted with ethylacetate and combined organics dried, filtered and concentrated to give a brown gum which was dissolved in MeOH (100 mL) and stirred with activated carbon. Filtration through a dicalite pad followed by concentration and purification on silica eluting with 0-2% MeOH/DCM gave (S)-benzyl 5-(hydroxymethyl)-2,3-dihydro-1H-inden-2-ylcarbamate as a beige solid (2.2, 48%). $^1$H NMR (400 MHz, CDCl$_3$) δ 1.66 (t, 1H) 2.81 (m, 2H) 3.28 (m, 2H) 4.52 (bs, 1H) 4.65 (d, 2H) 4.95 (bs, 1H) 5.09 (bs, 2H) 7.15-7.37 (bm, 8H).

d) (S)-benzyl-5-((4-(hydroxymethyl)-3-(trifluoromethyl)-1H-pyrazol-1-yl)methyl)-2,3-dihydro-1H-inden-2-ylcarbamate

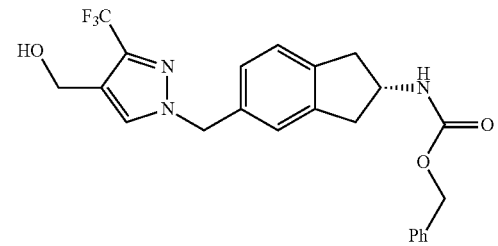 [SMILES: O=C(N[C@H]1Cc2ccc(Cn3cc(CO)c(C(F)(F)F)n3)cc2C1)OCc1ccccc1]

(S)-benzyl-5-(hydroxymethyl)-2,3-dihydro-1H-inden-2-ylcarbamate (7.13 mmol, 2.12 g) was dissolved in DCM (20 mL), thionyl chloride (14.26 mmol, 1.040 mL, 1.696 g) added and the resultant solution stirred at room temperature for 45 min. The sample was concentrated and azeotroped with dichloromethane (×4). Potassium carbonate (21.39 mmol, 2.96 g) was added followed by DMF (20 mL) and (3-(trifluoromethyl)-1H-pyrazol-4-yl)methanol (7.13 mmol, 1.184 g) and the mixture heated to 60° C. for 1 h. The mixture was concentrated and partitioned between ethylacetate/water. The aqueous layer was twice extracted with ethylacetate and combined organics dried, filtered and concentrated to give a yellow oil which was purified on silica eluting with 0-1% MeOH/DCM to give (S)-benzyl-5-((4-(hydroxymethyl)-3-(trifluoromethyl)-1H-pyrazol-1-yl)methyl)-2,3-dihydro-1H-inden-2-ylcarbamate as a light coloured oil (2.67 g, 84%). $^1$H NMR (400 MHz, CDCl$_3$) δ 1.83 (t, 1H) 2.79 (m, 2H) 3.27 (m, 2H) 4.51 (bs, 1H) 4.63 (d, 2H) 4.98 (bs, 1H) 5.08 (bs, 2H) 5.24 (s, 2H) 7.05-7.11 (m, 2H) 7.18 (m, 1H) 7.26-7.39 (m, 6H).

e) (S)-(1-((2-amino-2,3-dihydro-1H-inden-5-yl)methyl)-3-(trifluoromethyl)-1H-pyrazol-4-yl)methanol

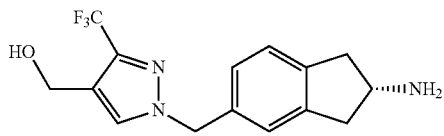 [SMILES: N[C@H]1Cc2ccc(Cn3cc(CO)c(C(F)(F)F)n3)cc2C1]

Palladium hydroxide (20% on carbon, 6.38 mmol, 0.895 g) was wetted in a hydrogenation vessel before addition of (S)-benzyl 5-((4-(hydroxymethyl)-3-(trifluoromethyl)-1H-pyrazol-1-yl)methyl)-2,3-dihydro-1H-inden-2-ylcarbamate (6.38 mmol, 2.84 g) and ethanol (50 mL) followed by aqueous 5N HCl solution (5.00 mL). The mixture was stirred under 2 bar of hydrogen for 1 hour before diluting with DCM (100 mL) and filtration through a dicalite pad which was then washed with 10% MeOH/DCM (200 mL). Combined organics were concentrated and partitioned between ethylacetate and saturated sodium carbonate solution. The organic layer was concentrated to give a light yellow oil which was purified on silica eluting with 5.5% 2M NH$_3$-MeOH/DCM to give (S)-(1-((2-amino-2,3-dihydro-1H-inden-5-yl)methyl)-3-(trifluoromethyl)-1H-pyrazol-4-yl)methanol (1.40 g, 70.7%). $^1$H NMR (400 MHz, CDCl$_3$) δ 2.65 (m, 2H) 3.16 (m, 2H) 3.82 (m, 1H) 4.59 (s, 2H) 5.23 (s, 2H) 7.06 (d, 1H) 7.10 (s, 1H) 7.18 (d, 1H) 7.38 (s, 1H)

f) (S)-1,1,1-trifluoro-N-(5-((4-(hydroxymethyl)-3-(trifluoromethyl)-1H-pyrazol-1-yl)methyl)-2,3-dihydro-1H-inden-2-yl)methanesulfonamide

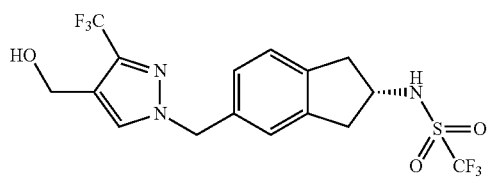 [SMILES: O=S(=O)(N[C@H]1Cc2ccc(Cn3cc(CO)c(C(F)(F)F)n3)cc2C1)C(F)(F)F]

(S)-(1-((2-amino-2,3-dihydro-1H-inden-5-yl)methyl)-3-(trifluoromethyl)-1H-pyrazol-4-yl)methanol (0.161 mmol, 50 mg) was suspended in DCM (2 mL) and triethylamine (0.321 mmol, 0.045 mL, 32.5 mg) added followed by trifluoromethanesulfonic anhydride (0.161 mmol, 0.027 mL, 45.3 mg) in DCM (500 µL) the reaction was stirred for 60 hours before the mixture was diluted with 0.5N HCl (3 mL) and DCM (3 mL). The phases mixed and separated using a hydrophobic frit and the organic layer concentrated to give a brown residue which was dissolved in DMSO (1 mL) and purified on basic preparative HPLC to give (S)-1,1,1-trifluoro-N-(5-((4-(hydroxymethyl)-3-(trifluoromethyl)-1H-pyrazol-1-yl)methyl)-2,3-dihydro-1H-inden-2-yl)methanesulfonamide (28.4 mg, 0.064 mmol, 39.9%) MS (ESI): m/z [M+H]$^+$ 444.0

EXAMPLE 12

(S)—N-(5-((4-(hydroxymethyl)-3-(trifluoromethyl)-1H-pyrazol-1-yl)methyl)-2,3-dihydro-1H-inden-2-yl)methanesulfonamide

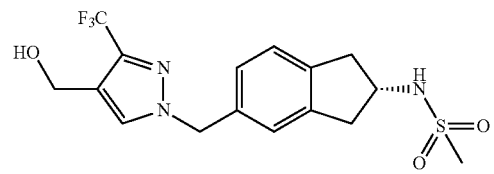 [SMILES: CS(=O)(=O)N[C@H]1Cc2ccc(Cn3cc(CO)c(C(F)(F)F)n3)cc2C1]

(S)-(1-((2-amino-2,3-dihydro-1H-inden-5-yl)methyl)-3-(trifluoromethyl)-1H-pyrazol-4-yl)methanol (0.16 mmol, 50 mg) was dissolved in THF (2 mL) and triethylamine (0.299 mmol, 42 µL, 30 mg) followed by methanesulfonyl chloride (0.16 mmol, 18.4 mg) and the solution stirred at room temperature overnight. The reaction was concentrated before partitioning between dichlormethane (3 mL) and 1N HCl (3 mL). The organic layer was collected and dried using a hydrophobic frit and concentrated under a stream of nitrogen to give a brown residue which was dissolved in DMSO (1 mL) and purified on preparative basic HPLC to give (S)—N-(5-((4-(hydroxymethyl)-3-(trifluoromethyl)-1H-pyrazol-1-yl)methyl)-2,3-dihydro-1H-inden-2-yl)methanesulfonamide (32.1 mg, 0.082 mmol, 51.2%) MS (ESI): m/z [M+H]$^+$ 390.0

EXAMPLE 13

(S)—N-(5-((4-(hydroxymethyl)-3-(trifluoromethyl)-1H-pyrazol-1-yl)methyl)-2,3-dihydro-1H-inden-2-yl)ethanesulfonamide

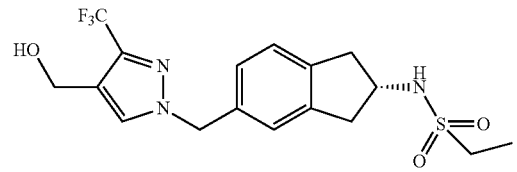 [SMILES: CCS(=O)(=O)N[C@H]1Cc2ccc(Cn3cc(CO)c(C(F)(F)F)n3)cc2C1]

In a similar manner to example 12, ethanesulfonylchloride was used instead of methanesulfonylchloride to yield the title compound (1.6 mg, 3.97 µmol, 2.5%). MS (ESI): m/z [M+H]$^+$ 404.2

EXAMPLE 14

(S)-2,2,2-trifluoro-N-(5-((4-(hydroxymethyl)-3-(trifluoromethyl)-1H-pyrazol-1-yl)methyl)-2,3-dihydro-1H-inden-2-yl)ethanesulfonamide

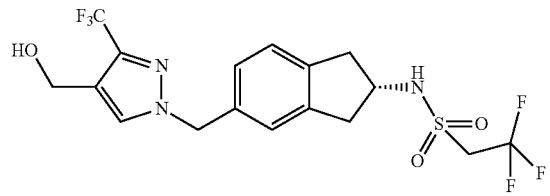 [SMILES: O=S(=O)(CC(F)(F)F)N[C@H]1Cc2ccc(Cn3cc(CO)c(C(F)(F)F)n3)cc2C1]

In a similar manner to example 12, 2,2,2-trifluoroethanesulfonyl chloride was used instead of methanesulfonylchloride to yield the title compound (12.6 mg, 0.028 mmol, 17.1%). MS (ESI): m/z [M−H]⁻ 456.0

EXAMPLE 15

(S)—N-(5-((4-(hydroxymethyl)-3-(trifluoromethyl)-1H-pyrazol-1-yl)methyl)-2,3-dihydro-1H-inden-2-yl) cyclopropanesulfonamide

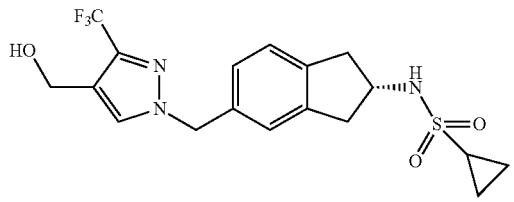 [SMILES: O=S(=O)(N[C@H]1Cc2ccc(Cn3cc(CO)c(C(F)(F)F)n3)cc2C1)C1CC1]

In a similar manner to example 12, cyclopropanesulfonylchloride was used instead of methanesulfonylchloride to yield the title compound (46.2 mg, 0.11 mmol, 69.1%). MS (ESI): m/z [M+H]⁺ 416.2

EXAMPLE 16

(S)—N-(5-((4-(hydroxymethyl)-3-(trifluoromethyl)-1H-pyrazol-1-yl)methyl)-2,3-dihydro-1H-inden-2-yl) dimethylsulfonylurea

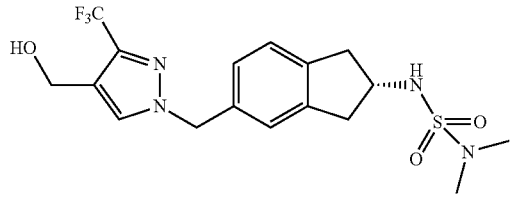 [SMILES: CN(C)S(=O)(=O)N[C@H]1Cc2ccc(Cn3cc(CO)c(C(F)(F)F)n3)cc2C1]

In a similar manner to example 12, dimethylsulfamoylchloride was used instead of methanesulfonylchloride to yield the title compound (35.5 mg, 0.085 mmol, 52.7%). MS (ESI): m/z [M−H]⁻ 417.3

EXAMPLE 17

(S)—N-(5-((4-(hydroxymethyl)-3-(trifluoromethyl)-1H-pyrazol-1-yl)methyl)-2,3-dihydro-1H-inden-2-yl)-2-methoxybenzenesulfonamide

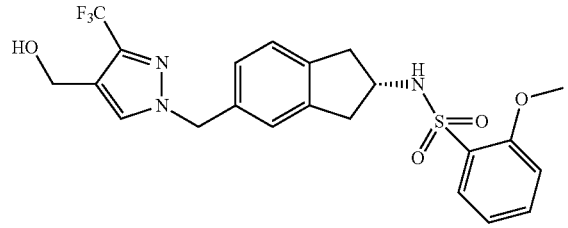 [SMILES: COc1ccccc1S(=O)(=O)N[C@H]1Cc2ccc(Cn3cc(CO)c(C(F)(F)F)n3)cc2C1]

In a similar manner to example 12, 2-methoxybenzene-1-sulfonyl chloride was used instead of methanesulfonylchloride to yield the title compound (30.5 mg, 0.063 mmol, 39.2%). MS (ESI): m/z [M−H]⁻ 480.1

EXAMPLE 18

(S)—N-(5-((4-(hydroxymethyl)-3-(trifluoromethyl)-1H-pyrazol-1-yl)methyl)-2,3-dihydro-1H-inden-2-yl) furan-2-sulfonamide

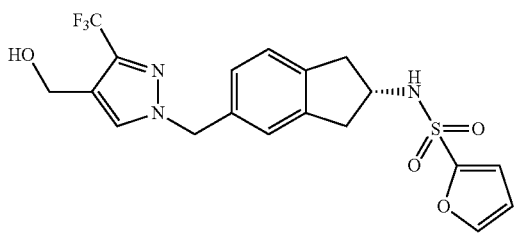

(S)-(1-((2-amino-2,3-dihydro-1H-inden-5-yl)methyl)-3-(trifluoromethyl)-1H-pyrazol-4-yl)methanol (0.08 mmol, 25 mg) was dissolved in THF (1 mL) and triethylamine (0.25 mmol, 35 µL, 25 mg) followed by furan-2-sulfonyl chloride (0.084 mmol, 14.05 mg) and the solution stirred at room temperature overnight. The reaction was concentrated before partitioning between dichlormethane (3 mL) and 1N HCl (3 mL). The organic layer was collected and dried using a hydrophobic frit and concentrated under a stream of nitrogen to give a brown residue which was dissolved in DMSO (1 mL) and purified on preparative basic HPLC to give (S)—N-(5-((4-(hydroxymethyl)-3-(trifluoromethyl)-1H-pyrazol-1-yl)methyl)-2,3-dihydro-1H-inden-2-yl)furan-2-sulfonamide (14.3 mg, 0.032 mmol, 40.5%) MS (ESI): m/z [M+H]⁺ 442.2

EXAMPLE 19

(S)—N-(5-((4-(hydroxymethyl)-3-(trifluoromethyl)-1H-pyrazol-1-yl)methyl)-2,3-dihydro-1H-inden-2-yl) thiophene-2-sulfonamide

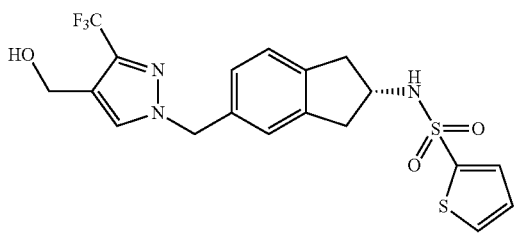 [SMILES: O=S(=O)(N[C@H]1Cc2ccc(Cn3cc(CO)c(C(F)(F)F)n3)cc2C1)c1ccco1]

In a similar manner to example 18, thiophene-2-sulfonyl chloride was used instead of furan-2-sulfonyl chloride to yield the title compound (19.0 mg, 0.042 mmol, 51.9%). MS (ESI): m/z [M+H]⁺ 458.0

EXAMPLE 20

(S)—N-(5-((4-(hydroxymethyl)-3-(trifluoromethyl)-1H-pyrazol-1-yl)methyl)-2,3-dihydro-1H-inden-2-yl)thiophene-3-sulfonamide

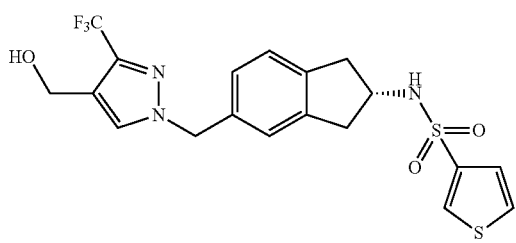 [SMILES: O=S(=O)(N[C@H]1Cc2ccc(Cn3cc(CO)c(C(F)(F)F)n3)cc2C1)c1ccsc1]

In a similar manner to example 18, thiophene-3-sulfonyl chloride was used instead of furan-2-sulfonyl chloride to yield the title compound (19.0 mg, 0.042 mmol, 51.9%). MS (ESI): m/z [M+H]$^+$ 458.0

EXAMPLE 21

(S)—N-(5-((4-(hydroxymethyl)-3-(trifluoromethyl)-1H-pyrazol-1-yl)methyl)-2,3-dihydro-1H-inden-2-yl)-1-methyl-3-(trifluoromethyl)-1H-pyrazole-4-sulfonamide

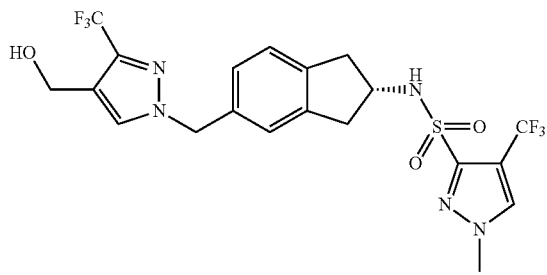 [SMILES: Cn1cc(C(F)(F)F)c(S(=O)(=O)N[C@H]2Cc3ccc(Cn4cc(CO)c(C(F)(F)F)n4)cc3C2)n1]

In a similar manner to example 18, 1-methyl-3-(trifluoromethyl)-1H-pyrazole-4-sulfonyl chloride was used instead of furan-2-sulfonyl chloride to yield the title compound (17.0 mg, 0.032 mmol, 40.6%) MS (ESI): m/z [M+Na]$^+$ 547.0

EXAMPLE 22

(R)—N-(5-((4-(2-hydroxypropan-2-yl)-3-(trifluoromethyl)-1H-pyrazol-1-yl)methyl)-2,3-dihydro-1H-inden-2-yl)propane-2-sulfonamide a) 2-(3-(Trifluoromethyl)-1H-pyrazol-4-yl)propan-2-ol

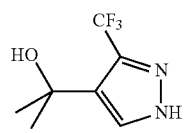

To a stirred solution of ethyl 3-(trifluoromethyl)-1H-pyrazole-4-carboxylate (649 mg, 3.12 mmol) in THF (6.50 mL) was added methylmagnesium bromide (2.57 g, 21.5 mmol) dropwise over 15 min such that the temperature remained at or below 0° C. The reaction mixture was stirred overnight and allowed to come to RT. Analysis at this stage showed the presence of unreacted starting material. The reaction mixture was cooled once more to <10° C. and more methylmagnesium bromide (2.57 g, 21.5 mmol) was added dropwise over 15 min and the resultant white suspension was stirred for a further 24 h. The reaction mixture was cooled to −5° C. and quenched with saturated NH$_4$Cl solution. The mixture was concentrated in vacuo and the residue partitioned between diethyl ether and water. The organic layer was separated, washed with saturated brine (×2), dried over MgSO$_4$, filtered and concentrated in vacuo to give the crude product as a yellow oil which partially solidified on standing. Purification by flash column chromatography-silica gel and elution with 40% EtOAc:isohexane gave the title product as a white solid (417 mg, 2.149 mmol, 69%). MS (ESI): 193 m/z [M−H]$^-$.

b) (R)—N-(5-((4-(2-hydroxypropan-2-yl)-3-(trifluoromethyl)-1H-pyrazol-1-yl)methyl)-2,3-dihydro-1H-inden-2-yl)propane-2-sulfonamide

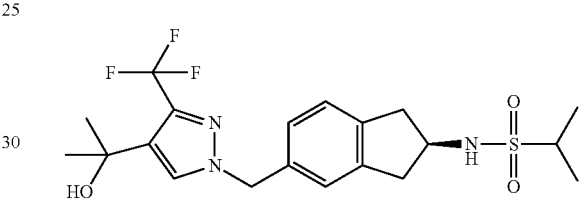

(R)—N-(5-(hydroxymethyl)-2,3-dihydro-1H-inden-2-yl)propane-2-sulfonamide (30 mg, 0.11 mmol) was dissolved in DCM (5 mL) and thionyl chloride (66 mg, 0.57 mmol) was added. The reaction mixture was stirred at room temperature for 1 h before being concentrated to dryness. The whole was dissolved in DMF (2 mL) and 2-(3-(trifluoromethyl)-1H-pyrazol-4-yl)propan-2-ol (21.6 mg, 0.11 mmol) was added followed by potassium carbonate (30.8 mg, 0.22 mmol). The reaction mixture was stirred at room temperature overnight before being quenched with water (2 mL) and the organics extracted with EtOAc (3×5 mL). The combined organics were washed with brine, dried (MgSO$_4$) and concentrated under reduced pressure. Purification by preparative basic HPLC gave (R)—N-(5-((4-(2-hydroxypropan-2-yl)-3-(trifluoromethyl)-1H-pyrazol-1-yl)methyl)-2,3-dihydro-1H-inden-2-yl)propane-2-sulfonamide (9.6 mg, 0.022 mmol, 19.4%). MS (ESI): m/z [M+H]$^+$ 446.5

EXAMPLE 23

(R)—N-(5-((4-(2-hydroxyethyl)-3-(trifluoromethyl)-1H-pyrazol-1-yl)methyl)-2,3-dihydro-1H-inden-2-yl)propane-2-sulfonamide

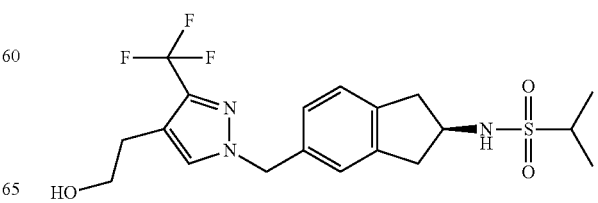

(R)—N-(5-(hydroxymethyl)-2,3-dihydro-1H-inden-2-yl)propane-2-sulfonamide (45 mg, 0.17 mmol) was dissolved in DCM (5 mL) and thionyl chloride (99 mg, 0.83 mmol) was added. The reaction mixture was stirred at room temperature for 1 h before being concentrated to dryness. The whole was dissolved in DMF (2 mL) and added to a solution of 2-(3-(trifluoromethyl)-1H-pyrazol-4-yl)ethanol (30 mg, 0.17 mmol) in DMF (2 mL) which had been treated with sodium hydride (8 mg, 0.33 mmol) for 15 min. The reaction mixture was heated to 65° C. for 3 h before being quenched with water (2 mL) and the organics extracted with EtOAc (3×5 mL). The combined organics were washed with brine, dried (MgSO₄) and concentrated under reduced pressure. Purification by preparative basic HPLC gave (R)—N-(5-((4-(2-hydroxyethyl)-3-(trifluoromethyl)-1H-pyrazol-1-yl)methyl)-2,3-dihydro-1H-inden-2-yl)propane-2-sulfonamide (13.6 mg, 0.032 mmol, 18.9%). MS (ESI): m/z [M+H]⁺ 432.5

EXAMPLE 24

(R)—N-(5-((3-(trifluoromethyl)-4,5,6,7-tetrahydro-1H-pyrazolo[4,3-d]pyridin-1-yl)methyl)-2,3-dihydro-1H-inden-2-yl)propane-2-sulfonamide

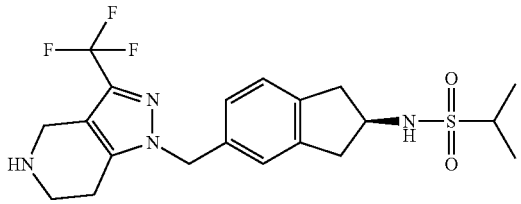 [SMILES: CC(C)S(=O)(=O)N[C@@H]1Cc2ccc(Cn3nc(C(F)(F)F)c4c3CCNC4)cc2C1]

(R)—N-(5-(hydroxymethyl)-2,3-dihydro-1H-inden-2-yl)propane-2-sulfonamide (23 mg, 0.086 mmol) was dissolved in DCM (5 mL) and thionyl chloride (51 mg, 0.43 mmol) was added. The reaction mixture was stirred at room temperature for 1 h before being concentrated to dryness. The whole was dissolved in DMF (2 mL) to this was added tert-butyl 3-(trifluoromethyl)-6,7-dihydro-1H-pyrazolo[4,3-c]pyridine-5(4H)-carboxylate (25 mg, 0.086 mmol) followed by potassium carbonate (24 mg, 0.172 mmol). The reaction mixture was heated to 65° C. for 3 h before being quenched with water (2 mL) and the organics extracted with EtOAc (3×5 mL). The combined organics were washed with brine, dried (MgSO₄) and concentrated under reduced pressure. The residue was treated with 1:1 TFA/DCM (2 mL) for 2 h before being concentrated to dryness. Purification by preparative basic HPLC gave (R)—N-(5-((3-(trifluoromethyl)-4,5,6,7-tetrahydro-1H-pyrazolo[4,3-c]pyridin-1-yl)methyl)-2,3-dihydro-1H-inden-2-yl)propane-2-sulfonamide (2.3 mg, 5.2 µmol, 6.1%). MS (ESI): m/z [M+H]⁺ 443.2

EXAMPLE 25

(R)—N-(5-((3,5-bis(trifluoromethyl)-1H-pyrazol-1-yl)methyl)-2,3-dihydro-1H-inden-2-yl)propane-2-sulfonamide

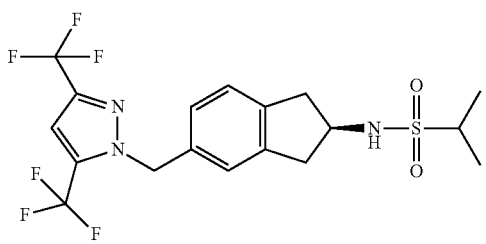 [SMILES: CC(C)S(=O)(=O)N[C@@H]1Cc2ccc(Cn3nc(C(F)(F)F)cc3C(F)(F)F)cc2C1]

(R)—N-(5-(hydroxymethyl)-2,3-dihydro-1H-inden-2-yl)propane-2-sulfonamide (50 mg, 0.19 mmol) was dissolved in DCM (5 mL) and cooled to 0° C. before thionyl chloride (110 mg, 0.93 mmol) was added. The reaction mixture was stirred at room temperature for 1 h before being concentrated to dryness. The whole was dissolved in DMF (3 mL) to this was added 3,5-bis(trifluoromethyl)-1H-pyrazole (38 mg 0.19 mmol) followed by potassium carbonate (51 mg, 0.37 mmol). The reaction mixture was heated to 60° C. for 2 h before being quenched with water (2 mL) and the organics extracted with EtOAc (3×5 mL). The combined organics were washed with brine, dried (MgSO₄) and concentrated under reduced pressure. Purification by preparative acidic HPLC gave (R)—N-(5-((3,5-bis(trifluoromethyl)-1H-pyrazol-1-yl)methyl)-2,3-dihydro-1H-inden-2-yl)propane-2-sulfonamide (1.7 mg, 3.7 µmol, 2.0%). MS (ESI): m/z [M+H]⁺ 456.1

EXAMPLE 26

(R)—N-(5-((3,5-bis(trifluoromethyl)-1H-pyrazol-1-yl)methyl)-2,3-dihydro-1H-inden-2-yl)propane-2-sulfonamide

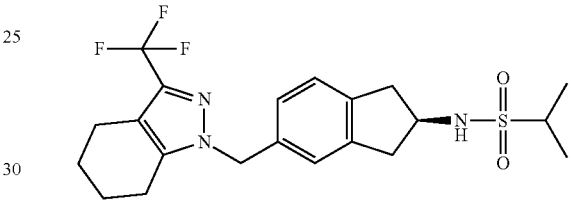

In a similar manner to example 25, 3-(trifluoromethyl)-4,5,6,7-tetrahydro-1H-indazole was used in place of 3,5-bis(trifluoromethyl)-1H-pyrazole to yield the title compound (5.6 mg, 0.13 mmol, 6.8%). MS (ESI): m/z [M+H]⁺ 442.0

EXAMPLE 27

(S)—N-(5-((3-(trifluoromethyl)-4,5,6,7-tetrahydro-1H-indazol-1-yl)methyl)-2,3-dihydro-1H-inden-2-yl)propane-2-sulfonamide

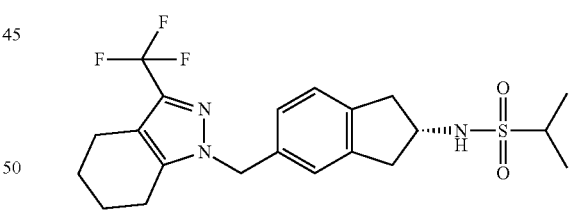

(S)—N-(5-(hydroxymethyl)-2,3-dihydro-1H-inden-2-yl)propane-2-sulfonamide (23 mg, 0.086 mmol) was dissolved in DCM (5 mL) and thionyl chloride (51 mg, 0.43 mmol) was added. The reaction mixture was stirred at room temperature for 1 h before being concentrated to dryness. The whole was dissolved in DMF (2 mL) to this was added 3-(trifluoromethyl)-4,5,6,7-tetrahydro-1H-indazole (25 mg, 0.086 mmol) followed by potassium carbonate (24 mg, 0.172 mmol). The reaction mixture was heated to 65° C. for 3 h before being quenched with water (2 mL) and the organics extracted with EtOAc (3×5 mL). The combined organics were washed with brine, dried (MgSO₄) and concentrated under reduced pressure. Purification by preparative basic HPLC gave the title compound (1.2 mg, 2.7 µmol, 2.9%). MS (ESI): m/z [M+H]⁺ 442.2

EXAMPLE 28

(S)—N-(5-((3,5-bis(trifluoromethyl)-1H-pyrazol-1-yl)methyl)-2,3-dihydro-1H-inden-2-yl)propane-2-sulfonamide

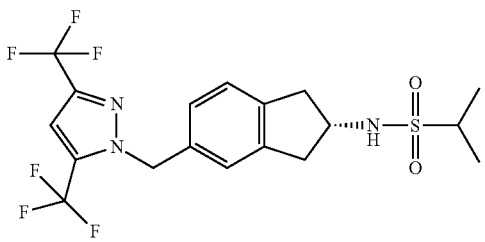 [SMILES: CC(C)S(=O)(=O)N[C@H]1Cc2ccc(Cn3nc(C(F)(F)F)cc3C(F)(F)F)cc2C1]

In a similar manner to example 27, 3,5-bis(trifluoromethyl)-1H-pyrazole was used in place of 3-(trifluoromethyl)-4,5,6,7-tetrahydro-1H-indazole to yield the title compound (7.4 mg, 0.016 mmol, 6.8%). MS (ESI): m/z [M−H]⁻ 454.0.

EXAMPLE 29

(S)—N-(5-((4-(fluoromethyl)-3-(trifluoromethyl)-1H-pyrazol-1-yl)methyl)-2,3-dihydro-1H-inden-2-yl)propane-2-sulfonamide

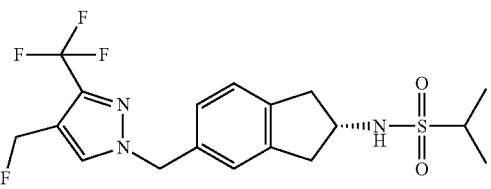 [SMILES: CC(C)S(=O)(=O)N[C@H]1Cc2ccc(Cn3cc(CF)c(C(F)(F)F)n3)cc2C1]

To a solution of (S)—N-(5-((4-(hydroxymethyl)-3-(trifluoromethyl)-1H-pyrazol-1-yl)methyl)-2,3-dihydro-1H-inden-2-yl)propane-2-sulfonamide (6.0 mg, 14 μmol) in DCM (3 mL) was added DAST (0.3 mL, 14 μmol). The whole was stirred at room temperature overnight before the reaction mixture was quenched by the addition of water (2 mL). The organics were filtered through a hydrophobic frit before being concentrated to dryness and the residue purified by basic preparative HPLC to give the title compound (1.0 mg, 2.4 μmol, 17%). MS (ESI): m/z [M−H]⁻ 418.0

EXAMPLE 30

(S)—N-(5-((4-(2-hydroxyethyl)-3-(trifluoromethyl)-1H-pyrazol-1-yl)methyl)-2,3-dihydro-1H-inden-2-yl)propane-2-sulfonamide

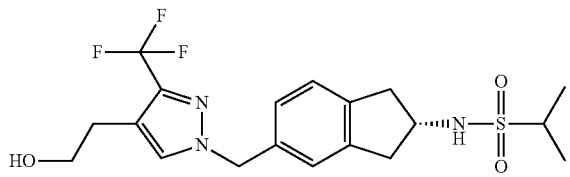 [SMILES: CC(C)S(=O)(=O)N[C@H]1Cc2ccc(Cn3cc(CCO)c(C(F)(F)F)n3)cc2C1]

In a similar manner to example 27, 2-(3-(trifluoromethyl)-1H-pyrazol-4-yl)ethanol was used in place of 3-(trifluoromethyl)-4,5,6,7-tetrahydro-1H-indazole to yield the title compound (14.7 mg, 0.034 mmol, 36.7%). MS (ESI): m/z [M+H]⁺ 432.2.

EXAMPLE 31

(S)—N-(5-((3-(trifluoromethyl)-1H-pyrazol-1-yl)methyl)-2,3-dihydro-1H-inden-2-yl)propane-2-sulfonamide

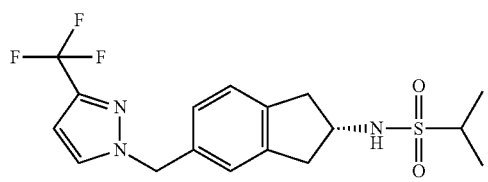 [SMILES: CC(C)S(=O)(=O)N[C@H]1Cc2ccc(Cn3ccc(C(F)(F)F)n3)cc2C1]

In a similar manner to example 27, 3-(trifluoromethyl)-1H-pyrazole was used in place of 3-(trifluoromethyl)-4,5,6,7-tetrahydro-1H-indazole to yield the title compound (15.0 mg, 0.039 mmol, 41.7%). MS (ESI): m/z [M+H]⁺ 388.4.

EXAMPLE 32

(S)—N-(5-((3-(trifluoromethyl)-4,5,6,7-tetrahydro-1H-pyrazolo[4,3-d]pyridin-1-yl)methyl)-2,3-dihydro-1H-inden-2-yl)propane-2-sulfonamide

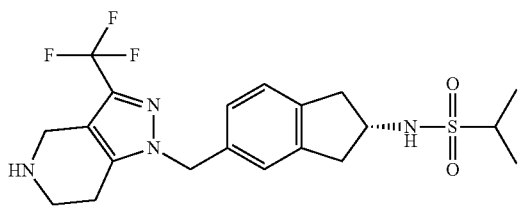 [SMILES: CC(C)S(=O)(=O)N[C@H]1Cc2ccc(Cn3nc(C(F)(F)F)c4c3CCNC4)cc2C1]

(S)—N-(5-(hydroxymethyl)-2,3-dihydro-1H-inden-2-yl)propane-2-sulfonamide (20 mg, 0.074 mmol) was dissolved in DCM (5 mL) and thionyl chloride (88 mg, 0.74 mmol) was added. The reaction mixture was stirred at room temperature for 1 h before being concentrated to dryness. The whole was dissolved in DMF (2 mL) to this was added tert-butyl 3-(trifluoromethyl)-6,7-dihydro-1H-pyrazolo[4,3-c]pyridine-5(4H)-carboxylate (22 mg, 0.074 mmol) followed by potassium carbonate (21 mg, 0.148 mmol). The reaction mixture was heated to 65° C. for 3 h before being quenched with water (2 mL) and the organics extracted with EtOAc (3×5 mL). The combined organics were washed with brine, dried (MgSO₄) and concentrated under reduced pressure. The residue was treated with 1:1 TFA/DCM (2 mL) for 2 h before being concentrated to dryness. Purification by preparative basic HPLC gave the title compound (12.6 mg, 0.028 mmol, 38.3%). MS (ESI): m/z [M+H]+ 443.5

EXAMPLE 33

(S)—N-(5-((3-(hydroxymethyl)-4-(trifluoromethyl)-1H-pyrrol-1-yl)methyl)-2,3-dihydro-1H-inden-2-yl)propane-2-sulfonamide a) Methyl 4-(trifluoromethyl)-1H-pyrrole-3-carboxylate

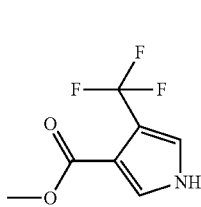

In a round-bottomed flask was added sodium hydride (3.24 mmol, 78 mg) in Et$_2$O (5 mL). A mixture of p-toluenesulfonylmethyl isocyanide (3.24 mmol, 634 mg) and (E)-methyl 4,4,4-trifluorobut-2-enoate (3.24 mmol, 500 mg) were added in a 2:1 mixture of Et$_2$O/DMSO (22.5 mL). The reaction mixture was stirred for a further 30 min then quenched with H$_2$O (10 mL) and extracted with Et$_2$O (×3). The Et$_2$O layers were combined and washed with brine, dried over MgSO$_4$, filtered and the solvent removed to give a yellow/orange solid. Purification by flash chromatography (1:4 EtOAc:Hept) the desired product (154 mg, 0.80 mmol, 24.6%). $^1$H NMR (400 MHz, CD$_3$OD) δ 3.79 (s, 3H) 7.20 (s, 1H) 7.50 (s, 1H).

b) (S)—N-(5-((3-(hydroxymethyl)-4-(trifluoromethyl)-1H-pyrrol-1-yl)methyl)-2,3-dihydro-1H-inden-2-yl)propane-2-sulfonamide

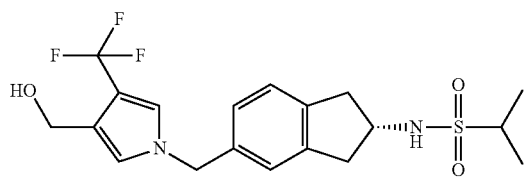 [SMILES: CC(C)S(=O)(=O)N[C@H]1Cc2ccc(Cn3cc(CO)c(C(F)(F)F)c3)cc2C1]

In a vial was added methyl 4-(trifluoromethyl)-1H-pyrrole-3-carboxylate (0.174 mmol, 33.6 mg) and sodium hydride (0.347 mmol, 8.34 mg) in DMF (3 mL) and the reactants stirred at room temp for 30 min. (S)—N-(5-(chloromethyl)-2,3-dihydro-1H-inden-2-yl)propane-2-sulfonamide (0.174 mmol, 50 mg) was added and the reactants heated at 65° C. for 3 h then allowed to cool to room temp and left to stand overnight. H$_2$O was added and the reaction mixture extracted with EtOAc (×3). The combined EtOAc layers were washed with H$_2$O (×3), brine, dried over MgSO$_4$, filtered and the solvent removed to give crude product.

This was dissolved in THF (5 mL) and LiAlH$_4$ added (6.6 mg). The reaction mixture was stirred at room temp for 3 hr before MeOH was added carefully and then the reaction mixture was stirred at room temp for 15 min and the solvent removed to give crude product. DCM was added and H$_2$O and then filtered through a hydrophobic frit, before the DCM layer concentrated to dryness. Purification by basic HPLC gave the title compound (4.3 mg, 10.3 μmol, 5.9%). MS (ESI): m/z [M+H]+ 415.5

EXAMPLE 34

(R)—N-(5-((4-(hydroxymethyl)-3-(trifluoromethyl)-1H-pyrazol-1-yl)methyl)-2,3-dihydro-1H-inden-2-yl)-2-chlorobenzenesulfonamide

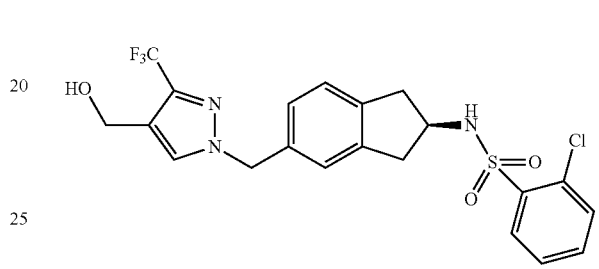

(R)-(1-((2-amino-2,3-dihydro-1H-inden-5-yl)methyl)-3-(trifluoromethyl)-1H-pyrazol-4-yl)methanol (0.064 mmol, 20 mg) was dissolved in tetrahydrofuran (1 mL) and triethylamine (0.128 mmol, 17.8 μL) followed by 2-chlorobenzenesulfonyl chloride (0.064 mmol, 13.6 mg) and the solution stirred at room temperature overnight. The reaction was concentrated to dryness to give a brown residue which was dissolved in DMSO (1 mL) and purified on preparative basic HPLC to give the title compound (9.8 mg, 0.02 mmol, 31.5%) MS (ESI): m/z [M−H]− 484.4.

EXAMPLE 35

(R)—N-(5-((4-(hydroxymethyl)-3-(trifluoromethyl)-1H-pyrazol-1-yl)methyl)-2,3-dihydro-1H-inden-2-yl)-2-chlorobenzenesulfonamide

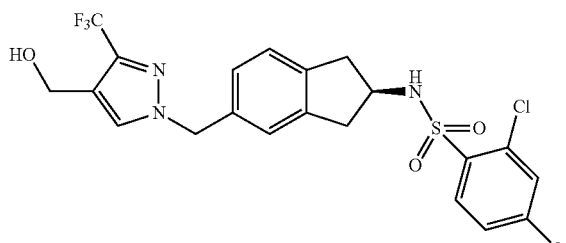

In a similar manner to example 34, 2,4-dichlorobenzenesulfonyl chloride was used in place of 2-chlorobenzenesulfonyl chloride to yield the title compound (7.7 mg, 0.015 mmol, 23.1%). MS (ESI): m/z [M−H]⁻ 518.3.

EXAMPLE 36

(R)—N-(5-((4-(hydroxymethyl)-3-(trifluoromethyl)-1H-pyrazol-1-yl)methyl)-2,3-dihydro-1H-inden-2-yl)-2-chlorobenzenesulfonamide

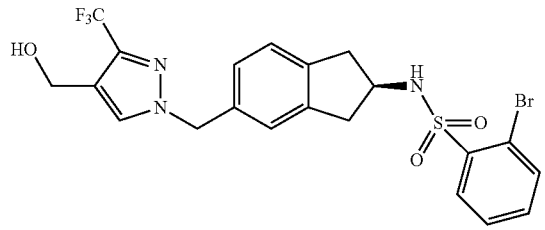 [SMILES: O=S(=O)(N[C@@H]1Cc2ccc(Cn3cc(CO)c(C(F)(F)F)n3)cc2C1)c1ccccc1Cl]

In a similar manner to example 34, 2-bromobenzenesulfonyl chloride was used in place of 2-chlorobenzenesulfonyl chloride to yield the title compound (11.6 mg, 0.022 mmol, 34.2%). MS (ESI): m/z [M+H]⁺ 531.0.

EXAMPLE 37

(R)—N-(5-((4-(hydroxymethyl)-3-(trifluoromethyl)-1H-pyrazol-1-yl)methyl)-2,3-dihydro-1H-inden-2-yl)-5-methyl-2-(trifluoromethyl)furan-3-sulfonamide

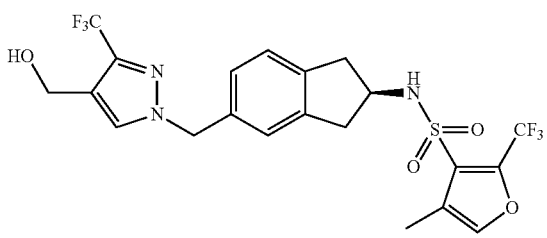 [SMILES: Cc1coc(C(F)(F)F)c1S(=O)(=O)N[C@@H]1Cc2ccc(Cn3cc(CO)c(C(F)(F)F)n3)cc2C1]

In a similar manner to example 34, 5-methyl-2-(trifluoromethyl)furan-3-sulfonyl chloride was used in place of 2-chlorobenzenesulfonyl chloride to yield the title compound (17.4 mg, 0.033 mmol, 51.7%). MS (ESI): m/z [M−H]⁻ 454.0.

EXAMPLE 38

(R)—N-(5-((4-(hydroxymethyl)-3-(trifluoromethyl)-1H-pyrazol-1-yl)methyl)-2,3-dihydro-1H-inden-2-yl)-1-methyl-1H-pyrazole-5-sulfonamide

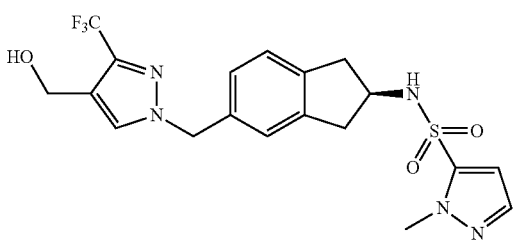 [SMILES: Cn1nccc1S(=O)(=O)N[C@@H]1Cc2ccc(Cn3cc(CO)c(C(F)(F)F)n3)cc2C1]

In a similar manner to example 34, 1-methyl-1H-pyrazole-5-sulfonyl chloride was used in place of 2-chlorobenzenesulfonyl chloride to yield the title compound (12.9 mg, 0.028 mmol, 44.1%). MS (ESI): m/z [M−H]⁻ 522.3.

EXAMPLE 39

(S)—N-(5-((4-(hydroxymethyl)-3-(trifluoromethyl)-1H-pyrazol-1-yl)methyl)-2,3-dihydro-1H-inden-2-yl)-2-chlorobenzenesulfonamide

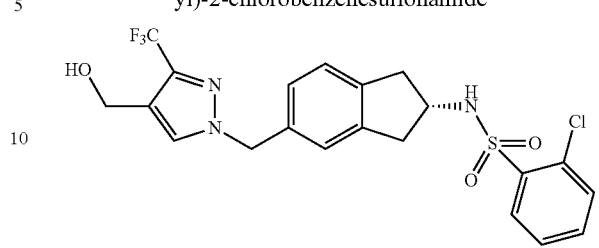

(S)-(1-((2-amino-2,3-dihydro-1H-inden-5-yl)methyl)-3-(trifluoromethyl)-1H-pyrazol-4-yl)methanol (0.064 mmol, 20 mg) was dissolved in tetrahydrofuran (1 mL) and triethylamine (0.128 mmol, 17.8 μL) followed by 2-chlorobenzenesulfonyl chloride (0.064 mmol, 13.6 mg) and the solution stirred at room temperature overnight. The reaction was concentrated to dryness to give a brown residue which was dissolved in DMSO (1 mL) and purified on preparative basic HPLC to give the title compound (17.4 mg, 0.036 mmol, 56.0%) MS (ESI): m/z [M−H]⁻ 484.5.

EXAMPLE 40

(S)—N-(5-((4-(hydroxymethyl)-3-(trifluoromethyl)-1H-pyrazol-1-yl)methyl)-2,3-dihydro-1H-inden-2-yl)-2-chloro-6-methylbenzenesulfonamide

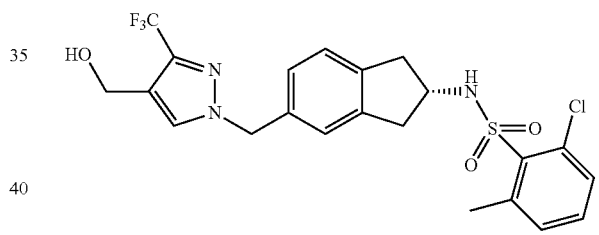

In a similar manner to example 39, 1-methyl-1H-pyrazole-5-sulfonyl chloride was used in place of 2-chlorobenzenesulfonyl chloride to yield the title compound (18.4 mg, 0.037 mmol, 57.5%). MS (ESI): m/z [M−H]⁻ 498.5.

EXAMPLE 41

(S)—N-(5-((4-(hydroxymethyl)-3-(trifluoromethyl)-1H-pyrazol-1-yl)methyl)-2,3-dihydro-1H-inden-2-yl)-5-methyl-2-(trifluoromethyl)furan-3-sulfonamide

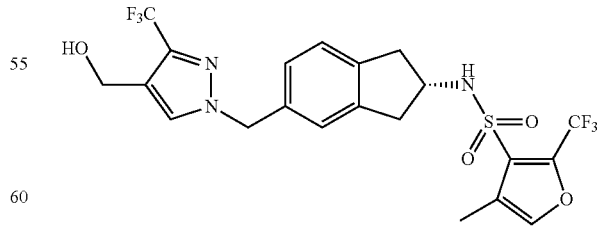

In a similar manner to example 39, 5-methyl-2-(trifluoromethyl)furan-3-sulfonyl chloride was used in place of 2-chlorobenzenesulfonyl chloride to yield the title compound (23.5 mg, 0.045 mmol, 69.9%). MS (ESI): m/z [M−H]⁻ 522.3.

EXAMPLE 42

(S)—N-(5-((4-(hydroxymethyl)-3-(trifluoromethyl)-1H-pyrazol-1-yl)methyl)-2,3-dihydro-1H-inden-2-yl)-1-methyl-1H-pyrazole-5-sulfonamide

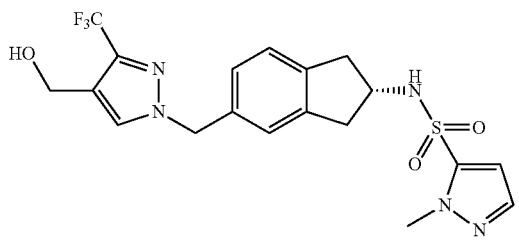 [SMILES: Cn1nccc1S(=O)(=O)N[C@H]1Cc2ccc(Cn3cc(CO)c(C(F)(F)F)n3)cc2C1]

In a similar manner to example 39, 1-methyl-1H-pyrazole-5-sulfonyl chloride was used in place of 2-chlorobenzenesulfonyl chloride to yield the title compound (18.9 mg, 0.041 mmol, 64.6%). MS (ESI): m/z [M−H]⁻ 454.1.

EXAMPLE 43

(S)—N-(5-((4-(hydroxymethyl)-3-(trifluoromethyl)-1H-pyrazol-1-yl)methyl)-2,3-dihydro-1H-inden-2-yl)-2-chlorobenzenesulfonamide

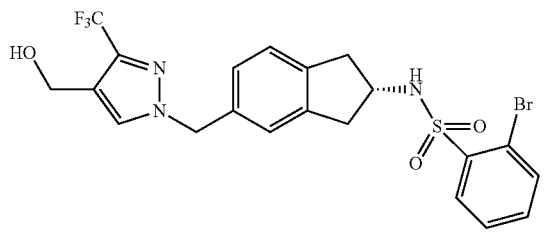 [SMILES: O=S(=O)(N[C@H]1Cc2ccc(Cn3cc(CO)c(C(F)(F)F)n3)cc2C1)c1ccccc1Br]

In a similar manner to example 34, 2-bromobenzenesulfonyl chloride was used in place of 2-chlorobenzenesulfonyl chloride to yield the title compound (11.6 mg, 0.022 mmol, 34.2%). MS (ESI): m/z [M−H]⁻ 528.3.

EXAMPLE 44

(S)—N-(5-((1-ethyl-3-(trifluoromethyl)-1H-pyrazol-5-yl)methyl)-2,3-dihydro-1H-inden-2-yl)propane-2-sulfonamide a) (S)—N-(5-(4,4,5,5-tetramethyl-1,3,2-dioxaborolan-2-yl)-2,3-dihydro-1H-inden-2-yl)propane-2-sulfonamide

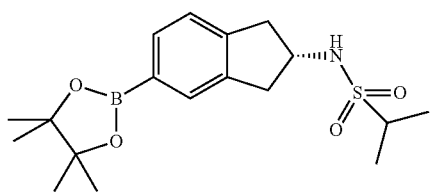 [SMILES: CC(C)S(=O)(=O)N[C@H]1Cc2ccc(B3OC(C)(C)C(C)(C)O3)cc2C1]

(S)—N-(5-bromo-2,3-dihydro-1H-inden-2-yl)propane-2-sulfonamide (1.885 mmol, 600 mg) was dissolved in dry DMF (10 mL) and the mixture degassed by bubbling nitrogen through the solution for 15 min. 4,4,4',4',5,5,5',5'-octamethyl-2,2'-bi(1,3,2-dioxaborolane) (2.074 mmol, 527 mg), 1,1'-bis(diphenylphosphino)ferrocenedichlorpalladium(II) (0.057 mmol, 40.9 mg) and potassium acetate (6.22 mmol, 611 mg) were then added and the mixture heated to 60° C. for 29 h. After this time the reaction temperature was increased to 80° C. and stirring continued for a further 24 h. The reaction mixture was then concentrated and diluted with EtOAc and water. The biphasic mixture was filtered through a dicalite pad before the phases were mixed and separated. The aqueous layer was further extracted with EtOAc (×2) and combined organics washed with brine, dried filtered and concentrated to give a dark brown residue. The mixture was purified on 20 g Si eluting with 20-40% EtOAc/Heptane to give the desired compound (280 mg, 0.766 mmol, 40.7%). ¹H NMR (400 MHz, CDCl₃) δ 1.36 (m, 18H) 2.90 (m, 2H) 3.15 (m, 1H) 3.27 (m, 2H), 4.25 (m, 1H) 4.55 (m, 1H), 7.20 (m 2H), 7.65 (m, 1H).

b) (S)—N-(5-((1-ethyl-3-(trifluoromethyl)-1H-pyrazol-5-yl)methyl)-2,3-dihydro-1H-inden-2-yl)propane-2-sulfonamide

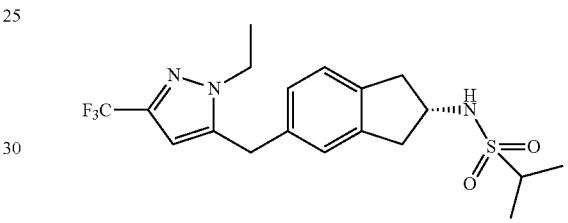

Tris(dibenzylideneacetone)dipalladium (0) chloroform adduct (0.014 mmol, 14.17 mg) was dissolved in THF (1 mL) and triphenylphosphine (0.027 mmol, 7.18 mg) added. The mixture was stirred at room temperature for 30 m before addition of N-bromosuccinimide (0.027 mmol, 4.87 mg). Stirring was continued for a further 30 min before addition of (S)—N-(5-(4,4,5,5-tetramethyl-1,3,2-dioxaborolan-2-yl)-2,3-dihydro-1H-inden-2-yl)propane-2-sulfonamide (0.137 mmol, 50 mg) in 500 μL THF, 5-(chloromethyl)-1-ethyl-3-(trifluoromethyl)-1H-pyrazole (0.137 mmol, 29.1 mg) in 500 μL THF and 2M Na₂CO₃ solution (2 mL). The mixture was heated to 100° C. for 10 min in the microwave before the mixture was filtered through a filter tip and concentrated to dryness. The residue was partitioned between DCM/Water and the organic phase collected and dried using a hydrophobic filter. TLC (1:1 EtOAc/Heptane) shows complex mix (see in process)—difficulty to assign product spot. The residue was purified using silica chromatography (20% EtOAc/Heptane) to give a residue which was further purified on basic HPLC to give the desired compound (3.6 mg, 8.7 μmol, 6.3%). MS (ESI): m/z [M−H]⁻ 414.4.

EXAMPLE 45

(S)—N-(5-((5-(trifluoromethyl)furan-2-yl)methyl)-2,3-dihydro-1H-inden-2-yl)propane-2-sulfonamide

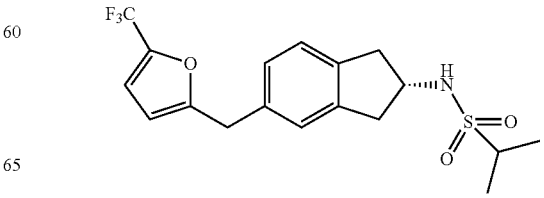

2-(bromomethyl)-5-(trifluoromethyl)furan (0.123 mmol, 28.2 mg), (S)—N-(5-(4,4,5,5-tetramethyl-1,3,2-dioxaborolan-2-yl)-2,3-dihydro-1H-inden-2-yl)propane-2-sulfonamide (0.123 mmol, 45 mg) and Bromo(N-succinimidyl)bis-(triphenylphosphine)palladium(II) (6.16 μmol, 4.98 mg) were suspended in THF (1 mL) and 2M NaCO3 (0.5 mL) added. The mixture was heated to 100° C. for 10 min. After this time the reaction mixture was irradiated for a further 20 min at 100° C. before standing overnight. The mixture was concentrated to remove THF before partitioning between DCM/H₂O. The organic layer was collected and dried using a hydrophobic filter tube. Concentration and purification on basic HPLC gave the title compound (7.5 mg, 0.019 mmol, 15.7%). MS (ESI): m/z [M−H]⁻ 386.3.

EXAMPLE 46

(S)—N-(5-((4-(hydroxymethyl)-5-(trifluoromethyl)-1H-pyrazol-1-yl)methyl)-2,3-dihydro-1H-inden-2-yl)propane-2-sulfonamide a) (S)-Ethyl 1-((2-(benzyloxycarbonylamino)-2,3-dihydro-1H-inden-5-yl)methyl)-5-(trifluoromethyl)-1H-pyrazole-4-carboxylate

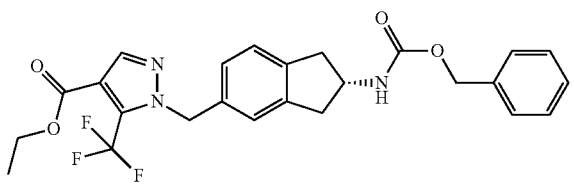 [SMILES: CCOC(=O)c1cnn(Cc2ccc3c(c2)C[C@@H](NC(=O)OCc2ccccc2)C3)c1C(F)(F)F]

(S)-Benzyl 5-(hydroxymethyl)-2,3-dihydro-1H-inden-2-ylcarbamate (2.96 mmol, 880 mg) was dissolved in DCM (10 mL) and thionyl chloride (5.92 mmol, 0.432 ml, 704 mg) added. The mixture was stirred at room temperature for 30 min TLC before the solvent was removed under reduced pressure and residual thionylchloride azeotroped with DCM (×3). To the residue was added potassium carbonate (8.88 mmol, 1227 mg) followed by DMF (8 ml) then ethyl 3-(trifluoromethyl)-1H-pyrazole-4-carboxylate (2.96 mmol, 616 mg) and the mixture heated to 60° C. After 1 h the mixture was concentrated and partitioned between EtOAc/H₂O and the organic layer was washed with water (×3). The organic layer was dried, filtered and concentrated to give a yellow oil which was purified by flash chromatography eluting with 15% EtOAc/Heptane to give the desired isomer as a colourless oil (45 mg, 0.092 mmol, 3.1%). ¹H NMR (400 MHz, CDCl₃) δ 1.34 (t, 3H) 2.75 (m, 2H) 3.25 (m, 2H) 4.33 (q, 2H), 4.50 (m, 1H) 4.95 (m, 1H), 5.08 (s, 2H) 5.48 (s, 2H) 7.00 (m, 2H) 7.15 (d, 1H) 7.34 (m, 5H) 7.99 (s, 1H).

b) (S)-Ethyl 1-((2-amino-2,3-dihydro-1H-inden-5-yl)methyl)-5-(trifluoromethyl)-1H-pyrazole-4-carboxylate hydrochloride

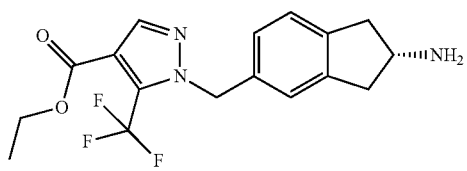 [SMILES: CCOC(=O)c1cnn(Cc2ccc3c(c2)C[C@@H](N)C3)c1C(F)(F)F]

Palladium hydroxide (0.092 mmol, 12.96 mg) was wetted with a small volume of water before addition of (S)-ethyl 1-((2-(benzyloxycarbonylamino)-2,3-dihydro-1H-inden-5-yl)methyl)-5-(trifluoromethyl)-1H-pyrazole-4-carboxylate (0.092 mmol, 45 mg) in Ethanol (5 mL). A small volume DCM was added to aid solubility. Aq. HCl 5N (0.500 ml) was added before the mixture was left to stand at room temp for around 1.5 h before hydrogenating at 2 bar for 45 min. After this time, the mixture was filtered through a filter tip and concentrated to give the desired product as a colourless oil (36 mg, 0.092 mmol, 100%). ¹H NMR (400 MHz, CD₃OD) δ 1.33 (t, 3H) 2.98 (m, 2H) 3.40 (m, 2H) 4.10 (m, 1H) 4.31 (q, 2H) 5.50 (s, 2H) 7.05 (d, 1H), 7.10 (s, 1H), 7.27 (d, 1H) 8.04 (s, 1H).

c) (S)-Ethyl 1-((2-(1-methylethylsulfonamido)-2,3-dihydro-1H-inden-5-yl)methyl)-5-(trifluoromethyl)-1H-pyrazole-4-carboxylate

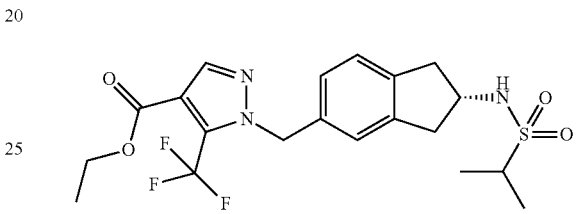

(S)-Ethyl 1-((2-amino-2,3-dihydro-1H-inden-5-yl)methyl)-5-(trifluoromethyl)-1H-pyrazole-4-carboxylate (0.102 mmol, 36 mg) was suspended in DCM (2 mL) and DBU (0.306 mmol, 0.046 mL, 46.5 mg) added which caused all solids to go into solution. Propane-2-sulfonyl chloride (0.204 mmol, 0.023 mL, 29.1 mg) was added dropwise and the reaction stirred at room temperature for 1 h. An additional 1 eq of sulfonyl chloride was added and the mixture stirred for a further 3 h before leaving to stand overnight and after this time an additional 2 eq. sulfonyl chloride and 3 eq. DBU added. The mixture was concentrated and purified on reverse phase HPLC to give the desired compound as a clear film (12 mg, 0.026 mmol, 25.6%). ¹H NMR (400 MHz, CDCl₃) δ 1.36 (m, 9H) 2.85 (m, 2H) 3.15 (m, 1H) 3.30 (m, 2H) 4.20 (m, 1H) 4.31 (m, 3H) 5.49 (s, 1H) 7.02 (m, 2H) 7.20 (d, 1H) 7.99 (s, 1H).

d) (S)—N-(5-((4-(hydroxymethyl)-5-(trifluoromethyl)-1H-pyrazol-1-yl)methyl)-2,3-dihydro-1H-inden-2-yl)propane-2-sulfonamide

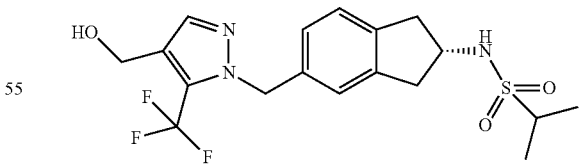

(S)-Ethyl-1-((2-(1-methylethylsulfonamido)-2,3-dihydro-1H-inden-5-yl)methyl)-5-(trifluoromethyl)-1H-pyrazole-4-carboxylate (0.026 mmol, 12 mg) was dissolved in THF (1 mL) and diisobutylaluminium hydride (0.304 mmol, 50 μL, 43.3 mg) added. After 15 min an additional 100 uL of DIBAL added and stirring continued for 30 min before the reaction was quenched with methanol. The mixture was concentrated then partitioned between DCM and Water. The aq. phase was acidified with 5N HCl and the phases mixed and separated using a hydrophobic frit. The organics were concentrated to dryness to give the desired compound as a clear film (10.6 mg, 0.025 mmol, 97%). MS (ESI): m/z [M+H]$^+$ 418.2.

EXAMPLE 47

N-(5-((4-(hydroxymethyl)-3-(trifluoromethyl)-1H-pyrazol-1-yl)methyl)-2,3-dihydro-1H-inden-1-yl)-2-methoxybenzenesulfonamide a) 5-Bromo-2,3-dihydro-1H-inden-1-amine

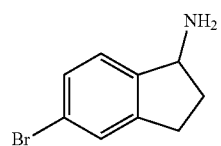 [SMILES: NC1CCc2cc(Br)ccc21]

5-bromo-2,3-dihydro-1H-inden-1-one (45.5 mmol, 9.6 g) and hydroxylamine hydrochloride (50.0 mmol, 3.48 g) were heated in ethanol (60 mL) for 5 hours with stirring. The stirrer bar was then removed and the solution allowed to cool and crystallize overnight. The product was collected by filtration and washed with diethyl ether to give a light yellow solid (7.1 g). This was immediately dissolved in acetic Acid (150 mL) and to the solution was added zinc dust (157 mmol, 10.27 g). The whole was stirred at room temperature for 3 d before the reaction mixture was filtered through dicalite and the pad washed with EtOAc. The filtrate was concentrated under reduced pressure before being partioned between ether and 2N HCl. The acidic layer was separated before being neutralised with NaOH (2N) and the organics extracted with EtOAc (2×100 mL), dried (hydrophobiv frit) and concentrated under reduced pressure to give the desired product as a brown oil. (5.0 g, 23.6 mmol, 68%). $^1$H NMR (400 MHz, CDCl$_3$) δ 1.60 (brs, 2H) 1.70 (m, 1H) 2.50 (m, 1H) 2.78 (m, 1H) 2.91 (m, 1H) 4.31 (t, 1H) 7.19 (d, 1H) 7.32 (m, 2H).

b) Benzyl 5-bromo-2,3-dihydro-1H-inden-1-ylcarbamate

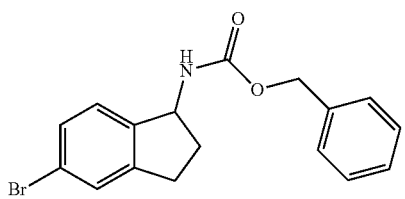 [SMILES: O=C(NC1CCc2cc(Br)ccc21)OCc1ccccc1]

To a solution of 5-bromo-2,3-dihydro-1H-inden-1-amine (23.57 mmol, 5 g) in ethyl acetate (40 mL) was added potassium carbonate (47.1 mmol, 6.52 g) as a solution in water (40.0 mL). The whole was stirred vigorously before benzyl chloroformate (25.9 mmol, 3.65 mL, 4.42 g) was added and stirring continued overnight. The reaction was quenched with more water and was extracted with DCM (2×). The organic layers were separated and dried using a hydrophobic frit, and were concentrated in vacuo to give desired product as a brown solid (5.5 g, 15.9 mmol, 67.4%). $^1$H NMR (400 MHz, CDCl$_3$) δ 1.82 (m, 1H) 2.60 (m, 1H) 2.85 (m, 1H) 2.90 (m, 1H), 4.95 (d, 1H) 5.18 (m, 3H) 7.18 (d, 1H) 7.34 (m, 7H).

c) Methyl 1-(benzyloxycarbonylamino)-2,3-dihydro-1H-indene-5-carboxylate

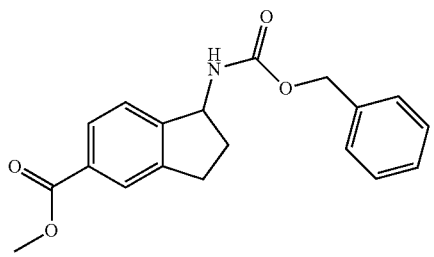 [SMILES: COC(=O)c1ccc2c(c1)CCC2NC(=O)OCc1ccccc1]

To a suspension of benzyl 5-bromo-2,3-dihydro-1H-inden-1-ylcarbamate (7.22 mmol, 2.5 g) in MeOH (30 mL/Acetonitrile (10.00 mL) was added trans-di-µ-acetobis[2-(di-O-tolylphosphino)benzyl]dipalladium(II) (0.725 mmol, 0.68 g), molybdenum hexacarbonyl (7.22 mmol, 1.906 g), tri-tertbutylphosphine tetrafluoroborate (1.482 mmol, 0.43 g) and DBU (10.97 mmol, 1.640 mL, 1.67 g). The whole was heated in a CEM microwave to 150° C. for 30 min before the reaction mixture was concentrated to dryness. The residue was taken up in DCM and washed with 2N HCl (2×100 mL) before being dried (1PS paper) and concentrated under reduced pressure. Purification was achieved by flash chromatography eluting with DCM—5% MeOH DCM to give a brown solid (1.8 g, 5.5 mmol, 77%). $^1$H NMR (400 MHz, CDCl$_3$) δ 1.85 (m, 1H) 2.65 (m, 1H) 2.90 (m, 1H) 3.00 (m, 1H) 3.90 (s, 1H) 5.05 (d, 1H) 5.16 (s, 1H) 5.20 (m, 1H) 7.35 (m, 7H) 7.88 (d, 1H).

d) Benzyl 5-(hydroxymethyl)-2,3-dihydro-1H-inden-1-ylcarbamate

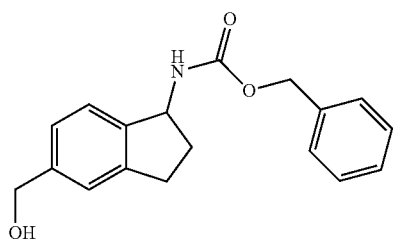 [SMILES: O=C(NC1CCc2cc(CO)ccc21)OCc1ccccc1]

To a solution of methyl 1-(benzyloxycarbonylamino)-2,3-dihydro-1H-indene-5-carboxylate (5.59 mmol, 1.82 g) in THF (30 mL) at 0° C. was added lithium aluminium hydride (5.59 mmol, 5.59 mL) in a dropwise fashion. Stirring at 0° C. was continued for 1.5 h after which time the reaction mixture was quenched with water and sat Rochelle's salt added followed by DCM & the organics separated/dried (1PS paper) before being concentrated to dryness. The residue was purified by flash chromatography (50 g, 1:1 EtOAc/heptane) to give an off-white solid (800 mg, 2.69 mmol, 48.1%). MS (ESI): m/z [M+H]+ 298.2 e) Ethyl 1-((1-(benzyloxycarbonylamino)-2,3-dihydro-1H-inden-5-yl)methyl)-3-(trifluoromethyl)-1H-pyrazole-4-carboxylate

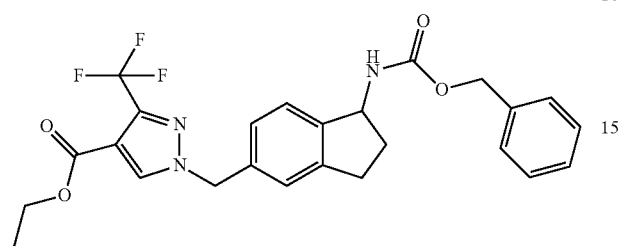

To a solution of benzyl 5-(hydroxymethyl)-2,3-dihydro-1H-inden-1-ylcarbamate (6.73 mmol, 2.0 g) in DCM (15 ml) was added thionyl chloride (13.45 mmol, 0.0.98 mL) and the whole was stirred for 2 h at room temperature after which time LCMS suggested 100% conversion to product. The reaction mixture was concentrated under reduced pressure and the residue re-dissolved in DCM. This was repeated a further 4 times to give a light yellow solid. This was dissolved in DMF (25 mL) and ethyl 3-(trifluoromethyl)-1H-pyrazole-4-carboxylate (1.29 g, 6.17 mmol) was added followed by potassium carbonate (18.52 mmol, 2.56 g). The resulting suspension was heated to 60° C. and this temperature was maintained for 2 h after the reaction mixture was diluted with sat NH4Cl followed by water and the organics extracted with EtOAc (2×100 mL), dried (1PS paper) and concentrated under reduced pressure. The residue was then purified by flash chromatography (40% EtOAc/heptane) to give a white solid (2.54, 5.21 mmol, 84%). $^1$H NMR (400 MHz, CDCl$_3$) δ 1.34 (t, 3H) 1.85 (m, 1H) 2.12 (m, 1H) 2.85 (m, 1H) 2.95 (m, 1H) 4.28 (q, 2H) 4.95 (d, 1H), 5.16 (s, 1H) 5.25 (m, 1H) 5.29 (s, 2H) 7.13 (brs, 2H) 7.35 (m, 6H), 7.87 (s, 1H).

f) Benzyl 5-((4-(hydroxymethyl)-3-(trifluoromethyl)-1H-pyrazol-1-yl)methyl)-2,3-dihydro-1H-inden-1-ylcarbamate

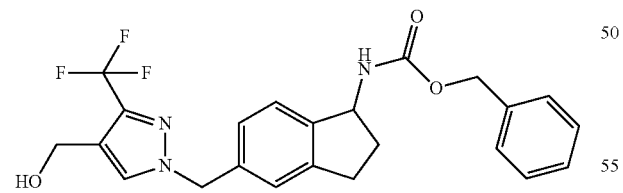

To a solution of ethyl 1-((1-(benzyloxycarbonylamino)-2,3-dihydro-1H-inden-5-yl)methyl)-3-(trifluoromethyl)-1H-pyrazole-4-carboxylate (5.21 mmol, 2.54 g) in THF (40 mL) at 0° C. was added lithium aluminium hydride (5.21 mmol, 5.21 mL) in a dropwise fashion. The whole was stirred at room temperature for 2 h before the reaction mixture was quenched by the dropwise addition of methanol followed by sat Rochelle's salt. The organics were extracted with DCM (2×100 mL) and dried (1PS paper) before being concentrated under reduced pressure. The residue was purified by flash chromatography (100 g, 1:1 EtOAc/heptane) to give a white solid (1.72 g, 3.86 mmol, 74.1%). $^1$H NMR (400 MHz, CDCl$_3$) δ 1.85 (m, 2H) 2.60 (m, 1H) 2.85 (m, 1H) 2.95 (m, 1H) 4.63 (brs, 2H) 5.00 (d, 1H) 5.14 (s, 2H) 5.20 (m, 1H) 5.25 (s, 2H) 7.09 (d, 2H) 7.34 (m, 7H).

g) (1-((1-Amino-2,3-dihydro-1H-inden-5-yl)methyl)-3-(trifluoromethyl)-1H-pyrazol-4-yl)methanol

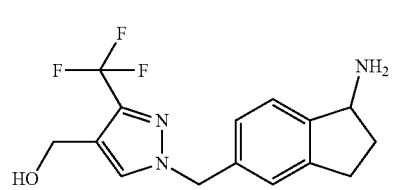 [SMILES: NC1CCc2cc(Cn3cc(CO)c(C(F)(F)F)n3)ccc21]

A suspension of palladium hydroxide (0.498 mmol, 350 mg) and benzyl 5-((4-(hydroxymethyl)-3-(trifluoromethyl)-1H-pyrazol-1-yl)methyl)-2,3-dihydro-1H-inden-1-ylcarbamate (2.69 mmol, 1.2 g) in ethanol (30 mL) was hydrogenated at 2 bar pressure for 30 min before the reaction vessel was vented and the whole filtered through a pad of dicalite. The pad was washed with EtOAc and the filtrate concentrated under reduced pressure. The residue was purified using SCX eluting with 2N NH$_3$/MeOH to give a clear oil which solidified on standing (700 mg, 2.25 mmol, 83%). $^1$H NMR (400 MHz, CDCl$_3$) δ 1.65 (m, 1H) 2.51 (m, 1H) 2.80 (m, 1H) 2.95 (m, 1H) 1.35 (t, 1H) 4.60 (s, 2H) 5.26 (s, 2H) 7.12 (d, 2H) 7.30 (d, 1H) 7.42 (s, 1H).

h) N-(5-((4-(hydroxymethyl)-3-(trifluoromethyl)-1H-pyrazol-1-yl)methyl)-2,3-dihydro-1H-inden-1-yl)-2-methoxybenzenesulfonamide

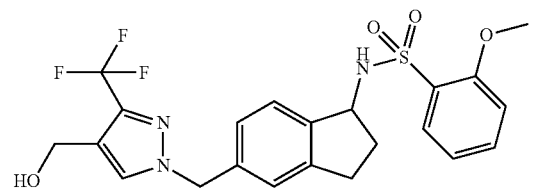 [SMILES: COc1ccccc1S(=O)(=O)NC1CCc2cc(Cn3cc(CO)c(C(F)(F)F)n3)ccc21]

To a solution of (1-((1-amino-2,3-dihydro-1H-inden-5-yl)methyl)-3-(trifluoromethyl)-1H-pyrazol-4-yl)methanol (0.096 mmol, 30 mg) and triethylamine (0.193 mmol, 0.027 mL, 19.50 mg) in DCM (0.9 mL) was added 2-methoxybenzenesulfonyl chloride (0.096 mmol, 19.91 mg) and the whole stirred at room temperature for 3 h. The reaction mixture was concentrated under reduced pressure and the residue purified by RP-HPLC to give a white solid (13.0 mg, 0.027 mmol, 28%). [M+H]+ 482.2.

EXAMPLE 47

N-(5-((4-(hydroxymethyl)-3-(trifluoromethyl)-1H-pyrazol-1-yl)methyl)-2,3-dihydro-1H-inden-1-yl)methanesulfonamide

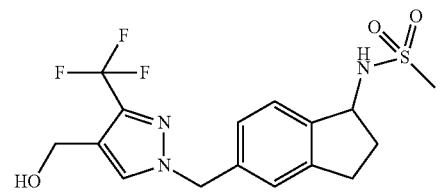 [SMILES: CS(=O)(=O)NC1CCc2cc(Cn3cc(CO)c(C(F)(F)F)n3)ccc21]

To a solution of (1-((1-amino-2,3-dihydro-1H-inden-5-yl)methyl)-3-(trifluoromethyl)-1H-pyrazol-4-yl)methanol (0.096 mmol, 30 mg) and triethylamine (0.193 mmol, 0.027 mL, 19.50 mg) in DCM (0.9 mL) was added methanesulfonyl chloride (0.096 mmol, 7.46 µL, 11.04 mg) and the whole stirred at room temperature for 3 h. The reaction mixture was concentrated under reduced pressure and the residue purified by RP-HPLC to give a clear film (2.2 mg 5.7 µmol, 5.9%). MS (ESI): m/z [M+H]$^+$ 390.0

EXAMPLE 48

N-(5-((4-(hydroxymethyl)-3-(trifluoromethyl)-1H-pyrazol-1-yl)methyl)-2,3-dihydro-1H-inden-1-yl)cyclopropanesulfonamide

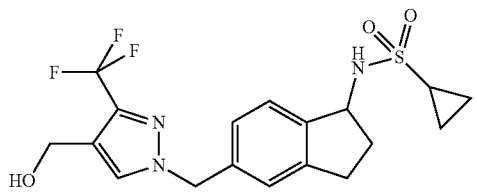 [SMILES: O=S(=O)(NC1CCc2cc(Cn3cc(CO)c(C(F)(F)F)n3)ccc21)C1CC1]

To a solution of (1-((1-amino-2,3-dihydro-1H-inden-5-yl)methyl)-3-(trifluoromethyl)-1H-pyrazol-4-yl)methanol (0.096 mmol, 30 mg) and triethylamine (0.193 mmol, 0.027 mL, 19.50 mg) in DCM (0.9 mL) was added cyclopropanesulfonyl chloride (0.096 mmol, 13.55 mg) and the whole stirred at room temperature overnight. The reaction mixture was concentrated under reduced pressure and the residue purified by RP-HPLC to give the desired product as a clear film (12.0 mg, 0.029 mmol, 30%). MS (ESI): m/z [M+H]$^-$ 417.0.

EXAMPLE 49

N-(5-((4-(hydroxymethyl)-3-(trifluoromethyl)-1H-pyrazol-1-yl)methyl)-2,3-dihydro-1H-inden-1-yl)-1-methyl-3-(trifluoromethyl)-1H-pyrazole-4-sulfonamide

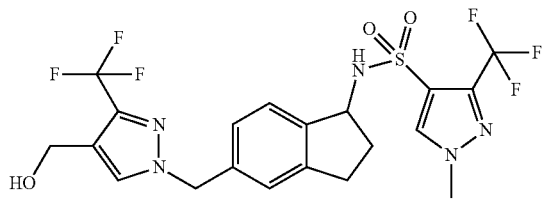 [SMILES: Cn1cc(S(=O)(=O)NC2CCc3cc(Cn4cc(CO)c(C(F)(F)F)n4)ccc32)c(C(F)(F)F)n1]

To a solution of (1-((1-amino-2,3-dihydro-1H-inden-5-yl)methyl)-3-(trifluoromethyl)-1H-pyrazol-4-yl)methanol (0.096 mmol, 30 mg) and triethylamine (0.193 mmol, 0.027 mL, 19.50 mg) in DCM (0.9 mL) was added 1-methyl-3-(trifluoromethyl)-1H-pyrazole-4-sulfonyl chloride (0.096 mmol, 23.96 mg) and the whole stirred at room temperature overnight. The reaction mixture was concentrated under reduced pressure and the residue purified by RP-HPLC to give a clear film (12.0 mg, 0.023 mmol, 23.8%). MS (ESI): m/z [M+H]$^+$ 524.0.

EXAMPLE 50

N-(5-((4-(hydroxymethyl)-3-(trifluoromethyl)-1H-pyrazol-1-yl)methyl)-2,3-dihydro-1H-inden-1-yl)-N,N-dimethylsulfonylurea

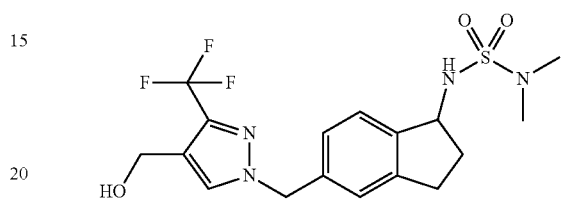

To a solution of (1-((1-amino-2,3-dihydro-1H-inden-5-yl)methyl)-3-(trifluoromethyl)-1H-pyrazol-4-yl)methanol (0.096 mmol, 30 mg) and triethylamine (0.193 mmol, 0.027 mL, 19.50 mg) in DCM (0.9 mL) was added dimethylsulfamoyl chloride (0.096 mmol, 13.84 mg) and the whole stirred at room temperature for 3 h. The reaction mixture was concentrated under reduced pressure and the residue purified by RP-HPLC to give a clear film (16.0 mg, 0.038 mmol, 39.7%). MS (ESI): m/z [M+H]$^+$ 419.0.

EXAMPLE 51

N-(5-((4-(hydroxymethyl)-3-(trifluoromethyl)-1H-pyrazol-1-yl)methyl)-2,3-dihydro-1H-inden-1-yl)-1,3-propanesultam

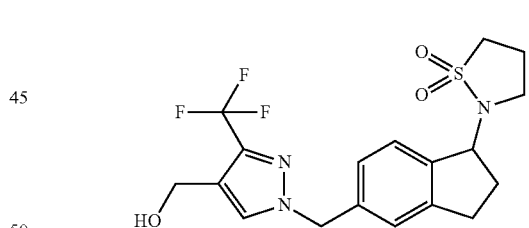

To a solution of (1-((1-amino-2,3-dihydro-1H-inden-5-yl)methyl)-3-(trifluoromethyl)-1H-pyrazol-4-yl)methanol (0.135 mmol, 42 mg) in NMP (1.0 mL) was added 3-chloropropane-1-sulfonyl chloride (0.135 mmol, 23.89 mg) and DIPEA (0.405 mmol, 0.067 ml, 52.3 mg). The whole was stirred for 3 h before sodium hydride (0.202 mmol, 8.09 mg) was added and stirring continued for a further 2 h. After this time the reaction mixture was quenched by the addition of sat NH$_4$Cl and further acidified by the addition of 2N HCl. The organics were separated/dried with DCM (hydrophobic frit) before being concentrated to dryness and the residue purified by prep HPLC to give a clear film (6.0 mg, 0.014 mmol, 10.7%). MS (ESI): m/z [M+H]+ 416.0.

EXAMPLE 52

2,2,2-Trifluoro-N-(5-((4-(hydroxymethyl)-3-(trifluoromethyl)-1H-pyrazol-1-yl)methyl)-2,3-dihydro-1H-inden-1-yl)acetamide

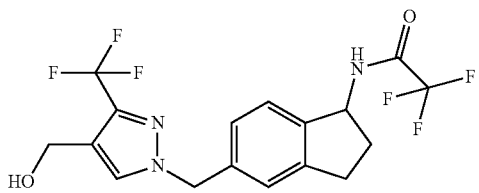 [SMILES: O=C(NC1CCc2cc(Cn3cc(CO)c(C(F)(F)F)n3)ccc21)C(F)(F)F]

To a solution of (1-((1-amino-2,3-dihydro-1H-inden-5-yl)methyl)-3-(trifluoromethyl)-1H-pyrazol-4-yl)methanol (0.199 mmol, 62.1 mg) and triethylamine (0.399 mmol, 0.056 mL, 40.4 mg) in DCM (1.2 mL) was added a solution of ethyl 2,2,2-trifluoroacetate (0.199 mmol, 0.024 mL, 28.3 mg) and the whole stirred at room temperature for 60 h. The reaction mixture was concentrated under reduced pressure and the residue purified by RP-HPLC to give a clear film (30.0 mg, 0.074 mmol, 36.9%). MS (ESI): m/z [M+H]+ 408.0.

EXAMPLE 53

(1-((1-(2,2,2-Trifluoroethylamino)-2,3-dihydro-1H-inden-5-yl)methyl)-3-(trifluoromethyl)-1H-pyrazol-4-yl)methanol

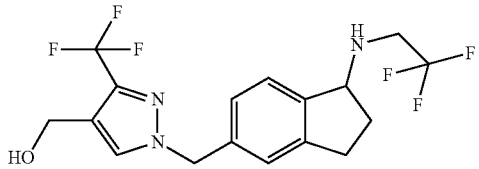 [SMILES: OCc1cn(Cc2ccc3c(c2)CCC3NCC(F)(F)F)nc1C(F)(F)F]

To a solution of 2,2,2-trifluoro-N-(5-((4-(hydroxymethyl)-3-(trifluoromethyl)-1H-pyrazol-1-yl)methyl)-2,3-dihydro-1H-inden-1-yl)acetamide (0.172 mmol, 70 mg) in THF (2 mL) was added diborane (1.719 mmol, 1.719 mL) and the whole heated to reflux for 6 h. The reaction mixture was allowed to cool to room temperature before being treated with 2N HCl (3 mL) and left to stand overnight. After this time the crude mixture was applied to an SCX column & eluted with 2N NH3/MeOH. After evaporation, the residue was further purified by prep LCMS to give a clear film (11 mg, 0.028 mmol, 16.3%). MS (ESI): m/z [M+H]+ 394.1.

EXAMPLE 54

N-(5-((4-(Hydroxymethyl)-3-(trifluoromethyl)-1H-pyrazol-1-yl)methyl)-2,3-dihydro-1H-inden-1-yl)isobutyramide

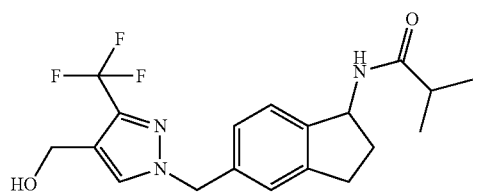 [SMILES: CC(C)C(=O)NC1CCc2cc(Cn3cc(CO)c(C(F)(F)F)n3)ccc21]

To a solution of (1-((1-amino-2,3-dihydro-1H-inden-5-yl)methyl)-3-(trifluoromethyl)-1H-pyrazol-4-yl)methanol (0.096 mmol, 30 mg), isobutyric acid (0.096 mmol, 8.94 μL 8.49 mg), triethylamine (0.193 mmol, 0.027 ml, 19.50 mg) and HOBt (0.096 mmol, 13.02 mg) in DMF (0.8 mL) was added EDCI/WSC (0.096 mmol, 18.47 mg). The whole was stirred at room temperature overnight before the reaction mixture was quenched by the addition of MeOH (100 μL) before being purified by prep HPLC to give a white solid (10.8 mg, 0.028 mmol, 29.4%). MS (ESI): m/z [M+H]+ 382.2

EXAMPLE 55

N-(5-((4-(Hydroxymethyl)-3-(trifluoromethyl)-1H-pyrazol-1-yl)methyl)-2,3-dihydro-1H-inden-1-yl)propane-2-sulfonamide a) N-(5-bromo-2,3-dihydro-1H-inden-1-yl)propane-2-sulfonamide

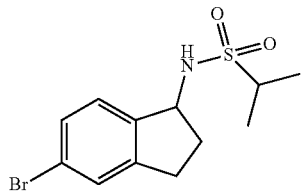 [SMILES: CC(C)S(=O)(=O)NC1CCc2cc(Br)ccc21]

At 0° C. and under protective atmosphere, a solution of 2-propanesulfonyl chloride (11.87 mL, 121 mmol) in DCM (121 mL) was added gradually to a solution of 5-bromo-2,3-dihydro-1H-inden-1-amine (12.8 g, 60.4 mmol) and 1,8-diazabicyclo[5.4.0]undec-7-ene (4.83 mL, 32.1 mmol) in dichloromethane (300 mL). The reaction was stirred at rt overnight. The reaction mixture was washed with 1N KHSO4 (1×) and sat NaHCO3 (2×) before being dried on Na2SO4 and solvent evaporated in vacuo to afford a green oil. Purification by column chromatography (25% EtOAc in hept) afforded the title compound as a white solid (6.0 g, 18.9 mmol, 31%). MS (ESI): m/z [M−H]− 317.0.

b) Methyl 1-(1-methylethylsulfonamido)-2,3-dihydro-1H-indene-5-carboxylate

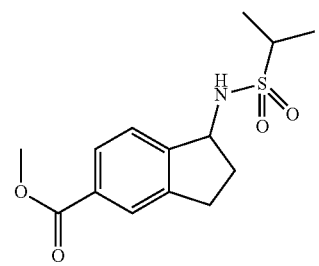 [SMILES: COC(=O)c1ccc2c(c1)CCC2NS(=O)(=O)C(C)C]

A 150 mL steel autoclave was charged with N-(5-bromo-2,3-dihydro-1H-inden-1-yl)propane-2-sulfonamide (4.85 g, 15.24 mmol), 1,1'-bis(diphenylphosphino)ferrocene palladium(II)dichloride (0.622 g, 0.762 mmol), and sodium carbonate (3.23 g, 30.5 mmol) in degassed methanol. The autoclave was placed under carbon monoxide atmosphere (12 bar) and stirred at 100° C. for 24 hr. After this time, catalyst and Na2CO3 were filtered off and replaced with a new batch and the reaction was stirred for 24 hr at 100° C. and 12 bar CO.

The mixture was filtered and partitioned between EtOAc and brine, organic layer separated, washed with brine. To the organic layer was added silica and Na$_2$SO$_4$ added and stirred for 20 min. The whole was filtered and solvent evaporated in vacuo to give a brown oil. Purification by flash chromatography (0-50% EtOAc in heptane) afforded the title compound as a yellow/brown oil (1 g, 22%). $^1$H NMR (400 MHz, CDCl$_3$) δ 1.46 (d, 6H) 1.95 (m, 1H) 2.65 (m, 1H) 2.85 (m, 1H) 3.00 (m, 1H) 3.25 (m, 1H) 3.91 (s, 3H) 4.25 (d, 1H) 5.00 (q, 1H) 7.50 (d, 1H) 7.90 (m, 2H).

c) N-(5-(hydroxymethyl)-2,3-dihydro-1H-inden-1-yl)propane-2-sulfonamide

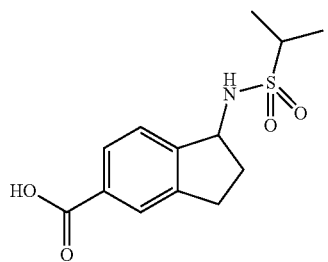 [SMILES: CC(C)S(=O)(=O)NC1CCc2cc(C(=O)O)ccc21]

At 0° C. lithium aluminium hydride (2.102 mL, 5.04 mmol) was added dropwise to a stirred solution of methyl 1-(1-methylethylsulfonamido)-2,3-dihydro-1H-indene-5-carboxylate (1 g, 3.36 mmol) in tetrahydrofuran (dry) (25 mL). Mixture warmed to rt and stirred for 4 hr. After this time the reaction mixture was again cooled to 0° C. and more lithium aluminium hydride (2.102 mL, 5.04 mmol) added and the whole stirred at room temperature for 30 min before being carefully quenched with H$_2$O (10 mL) and 2N NaOH (10 mL). The resulting mixture was filtered and partitioned between EtOAc and brine. The organic layer was separated, dried on Na$_2$SO$_4$ and solvent evaporated in vacuo to give a dark yellow oil. Purification by flash chromatography (0-100% EtOAc in Hept.) afforded the title compound as a colourless oil (670 mg 2.5 mmol, 74%). MS (ESI): m/z [M−H]$^-$ 268.0.

d) N-(5-(chloromethyl)-2,3-dihydro-1H-inden-1-yl)propane-2-sulfonamide

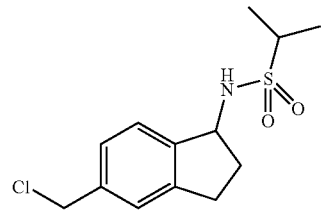 [SMILES: CC(C)S(=O)(=O)NC1CCc2cc(CCl)ccc21]

Thionyl chloride (0.355 mL, 4.90 mmol) was added to a solution of N-(5-(hydroxymethyl)-2,3-dihydro-1H-inden-1-yl)propane-2-sulfonamide (660 mg, 2.450 mmol) in DCM (10 mL). The whole was stirred for 1 h before the reaction mixture was evaporated to dryness and the crude material was purified by silica flash column chromatography (EtOAc/heptane: from 0% to 60% of EtOAc) to afford the title compound as a white solid (360 mg, 51%). MS (ESI): m/z [M−H]$^-$ 286.0 e) Ethyl 1-((1-(1-methylethylsulfonamido)-2,3-dihydro-1H-inden-5-yl)methyl)-3-(trifluoromethyl)-1H-pyrazole-4-carboxylate

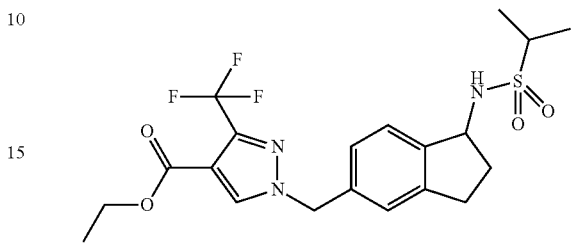

To N-(5-(chloromethyl)-2,3-dihydro-1H-inden-1-yl)propane-2-sulfonamide (0.250 mmol, 72 mg) in DMF (4 mL) was added ethyl 3-(trifluoromethyl)-1H-pyrazole-4-carboxylate (0.250 mmol, 52.1 mg) and Potassium carbonate (0.750 mmol, 104 mg). The resultant solution was heated to 60° C. with stirring. After 1.5 h the reaction mixture was concentrated to remove DMF before partitioning between EtOAc/H$_2$O and the phases mixed and separated. The organic layer was washed with water (×4) and brine before drying and concentration to a yellow oil. Purification on 10 g Si eluting with 1% MeOH/DCM gave the desired compound as an off-white solid (60 mg, 0.131 mmol, 52.2%). $^1$H NMR (400 MHz, CDCl$_3$) δ 1.33 (t, 3H) 1.44 (d, 6H) 1.95 (m, 1H) 2.65 (m, 1H) 2.85 (m, 1H) 3.00 (m, 1H) 3.25 (m, 1H) 4.15 (d, 1H) 4.29 (q, 2H) 4.95 (m, 1H) 5.30 (s, 2H) 7.14 (s, 1H) 7.18 (d, 1H) 7.48 (d, 1H) 7.88 (s, 1H).

f) N-(5-((4-(hydroxymethyl)-3-(trifluoromethyl)-1H-pyrazol-1-yl)methyl)-2,3-dihydro-1H-inden-1-yl)propane-2-sulfonamide

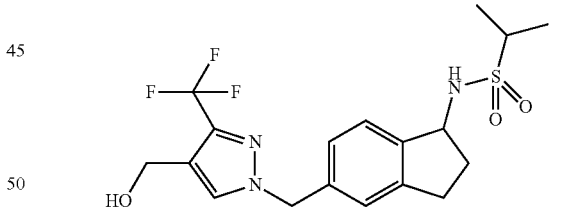

Ethyl-1-((1-(1-methylethylsulfonamido)-2,3-dihydro-1H-inden-5-yl)methyl)-3-(trifluoro methyl)-1H-pyrazole-4-carboxylate (0.196 mmol, 90 mg) was dissolved in THF (5 mL) and cooled in an ice bath under nitrogen. Di-isobutyl aluminium hydride (0.588 mmol, 0.588 mL) was added dropwise and the reaction stirred for 1.5 h. The reaction mixture was warmed to room temperature and stirred for a further 30 min before an additional 0.2 ml of di-isobutyl aluminium hydride was added and stirring continued for 30 min before quenching with MeOH followed by water. The mixture was concentrated before partitioning between EtOAc/water. The aq. layer was acidified with 5N HCl until all solids were in solution. The organic phase was collected, dried and concentrated and the residue purified by HPLC to give a colourless oil which crystallised on standing (63 mg, 0.151 mmol, 77%).

$^1$H NMR (400 MHz, CDCl$_3$) δ 1.43 (d, 6H) 1.95 (m, 1H) 2.65 (m, 1H) 2.80 (m, 1H) 3.00 (m, 1H), 3.24 (m, 1H) 4.20 (d, 1H) 4.65 (s, 2H) 4.95 (q, 1H) 5.28 (s, 2H) 7.13 (m, 2H) 7.44 (m, 2H).

EXAMPLE 56

Biological Assays

A: Ca$^{2+}$ Influx Fluorescence Assays

The compounds in this invention may be tested using a biological assay which measures Ca$^{2+}$ influx mediated through positive modulation of the AMPA (GluR1) receptor using standard techniques in the art such as, but not limited to, a FLEXstation (manufactured by Molecular Devices, Sunnyvale, Calif.). An optical readout using fluorescent probes is employed to measure ion channel dependent changes in intracellular ion concentration or membrane potential. The assay utilises the Ca$^{2+}$ conductance of functional homomeric GluR1(i) AMPA receptors to generate glutamate-dependent Ca$^{2+}$ responses. Influx of Ca$^{2+}$ through the ion channel is measured indirectly through an increase in intracellular Ca$^{2+}$ levels using the calcium sensitive dye such as, but not limited to, Fluo-3 (Molecular Devices, Sunnyvale, Calif.) in FLEXstation. A positive AMPA receptor modulator, in the presence of glutamate, will result in an influx of Ca$^{2+}$ through the ion channel which can be measured indirectly through an increase in intracellular Ca2+ levels using the calcium sensitive dye Fluo-3 in FLEXstation.

HEK.GluR1(i) cells were maintained in DMEM supplemented with 10% fetaclone II, 1% non-essential amino acids and 150 μg/mL hygromycin, at 37° C./5% CO2. Twenty-four h prior to the assay, the cells were harvested with trypsin and seeded onto Costar 96 well clear bottomed black plates at a density of 3.5×10$^4$ per well.

Cells were loaded with 5 μM fluo3-AM in DMEM media in the absence of hygromycin and incubated at 37° C./5% CO$_2$ for one h. After dye loading, the cells were washed once with 200 μl of low calcium solution (10 mM hepes, pH 7.4, 160 mM NaCl, 4.5 mM KCl, 2 mM CaCl$_2$, 1 mM MgCl$_2$, 10 mM glucose) containing 0.625 mM of probenecid (inhibitor for the anion-exchange protein) to remove the dye. Then 200 μl of low calcium solution was added to each well. The Flexstation added 50 μl of glutamate+/−test compound in high calcium solution (10 mM Hepes, pH 7.4, 160 mM NaCl, 4.5 mM KCl, 20 mM CaCl$_2$, 1 mM MgCl$_2$ and 10 mM glucose) to each well and the ensuing response was monitored on FLEXstation.

The compounds of this invention exhibit positive modulation of the AMPA receptor having EC$_{50}$ values in the range 0.3 μM to 30 μM. For instance, Example 18 gave an EC$_{50}$ of 2.5 μM.

B: Patch Clamp Recording.

The whole cell configuration of the patch clamp technique (Hamill et al., Pflugers Arch. 1981, 39, 85-100) was used to measure glutamate-evoked currents from postnatal rat cortical neurons. A glass coverslip containing the culture was transferred to the recording chamber (Warner Instrument Corp., Hamden, Conn.) mounted on the stage of an inverted microscope (Nikon, Kingston, UK). The recording chamber contained 1-2 ml extracellular solution (145 mM NaCl, 5.4 mM KCl, 10 mM HEPES, 0.8 mM MgCl$_2$, 1.8 CaCl$_2$, 10 mM glucose and 30 mM sucrose, adjusted to pH 7.4 with 1M NaOH) and was constantly perused at a rate of 1 ml/min. Recordings were performed at room temperature (20-22° C.) using an Axopatch 200B amplifier (Axon Instruments Ltd., Foster City, Calif.).

Data acquisition and analysis was performed using Signal software (Cambridge Electronic Design Ltd., Cambridge, UK). Pipettes were manufactured from GC120E-10 glass (Harvard Apparatus, Edenbridge UK) using a model P-87 electrode puller (Sutter Instruments Co., Novarto, Calif.). The patch electrodes had typical resistances of between 3-5 MΩ when filled with intracellular solution (140 mM potassium gluconate, 20 mM HEPES, 1.1 mM EGTA, 5 mM phosphocreatine, 3 mM ATP, 0.3 mM GTP, 0.1 mM Caca2, 5 mM MgCl$_2$, adjusted to pH 7.4 with 1M KOH).

Cells were voltage clamped at a holding potential of −60 mV and glutamate (0.5 mM) was applied using a 12 channel semi-rapid drug application device (DAD-12. Digitimer Ltd., Welwyn Garden city, UK). The agonist glutamate was applied for 1 s every 30 s. The response did not "run-down" over time using the whole-cell configuration. Between applications saline flowed to clear any dead volume in the system. For each application steady-state currents were plotted from the difference in baseline and steady state current and averaged over 300 ms.

Two solutions of the compound in extracellular solution were made up, one with glutamate and one without. The protocol was: 10 second application of compound, 1 second application of compound+glutamate and then 10 second wash with saline, then a 10 second delay. When the compound was not soluble, 0.5% DMSO was used as a co-solvent. Results were determined as the percentage increase in steady state current at 10 μM concentration of the compound of the invention in extracellular solution.

The invention claimed is:

1. A heterocyclic derivative according to formula I

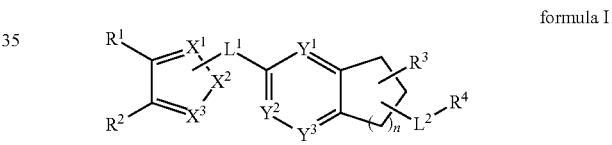

formula I wherein

L$^1$ is (CR$^6$R$^7$)$_m$ or CO;

L$^2$ is NR$^8$SO$_2$ or SO$_2$NR$^9$;

R$^1$ is H, C$_{1-6}$alkyl, C$_{3-8}$cycloalkyl, C$_{1-6}$alkyloxy, halogen, CN, COR$^{10}$, SR$^{11}$, SOR$^{12}$, SO$_2$R$^{13}$, NHCOR$^{14}$, NHSO$_2$R$^{15}$, NHCOR$^{16}$ or CONHR$^{17}$, said C$_{1-6}$alkyl, C$_{3-8}$cycloalkyl and C$_{1-6}$alkyloxy being optionally substituted with one or more halogens;

R$^2$ is C$_{1-6}$alkyl, C$_{3-8}$cycloalkyl, C$_{1-6}$alkyloxy, or CN, said C$_{1-6}$alkyl, C$_{3-8}$cycloalkyl and C$_{1-6}$alkyloxy being substituted with one or more moiety independently selected from halogen, OH, C$_{1-6}$alkyloxy, CN, NR$^{18}$R$^{19}$, COR$^{20}$, SR$^{21}$, SOR$^{22}$, SO$_2$R$^{23}$, NHCOR$^{24}$, NHSO$_2$R$^{25}$, NHCOR$^{26}$ and CONHR$^{27}$;

R$^3$ is H, C$_{1-6}$alkyl, C$_{3-8}$cycloalkyl, C$_{1-6}$alkyloxy, halogen or CN, said C$_{1-6}$alkyl, C$_{3-8}$cycloalkyl and C$_{1-6}$alkyloxy being optionally substituted with one or more halogens;

R$^4$ is H, C$_{1-6}$alkyl, C$_{2-6}$alkenyl, C$_{2-6}$alkynyl, C$_{3-8}$cycloalkyl, C$_{1-2}$alkylC$_{3-8}$cycloalkyl, NR$^{28}$R$^{29}$, C$_{6-10}$aryl or a 5-9 membered heteroaryl ring system comprising 1-2 heteroatoms independently selected from O, S and N, wherein said C$_{1-6}$alkyl, C$_{3-8}$cycloalkyl, C$_{6-10}$aryl and 5-9 membered heteroaryl ring system are optionally substituted with one or more moieties independently selected from halogen, C$_{1-6}$alkyl, hydroxy and C$_{1-6}$alkyloxy, said C$_{1-6}$alkyl, and C$_{1-6}$alkyloxy being optionally substituted with 1-3 halogens;

$R^6$-$R^{10}$ are independently H or $C_{1-6}$alkyl;
$R^{11}$-$R^{16}$ are independently $C_{1-6}$alkyl;
$R^{17}$ is H or $C_{1-6}$alkyl;
$R^{18}$ and $R^{19}$ are independently H or $C_{1-4}$alkyl optionally substituted with a 5-9 membered heteroaryl ring system comprising 1-2 heteroatoms independently selected from O, S and N, or
$R^{18}$ and $R^{19}$ together with the N to which they are bonded form a 4-6 membered saturated or unsaturated heterocyclic ring optionally comprising another heteroatom selected from O, S and $N(R^{30})_p$;
$R^{20}$ is independently H or $C_{1-4}$alkyl;
$R^{21}$-$R^{26}$ are independently $C_{1-4}$alkyl;
$R^{27}$ is H or $C_{1-4}$alkyl;
$R^{28}$ and $R^{29}$ are independently H or $C_{1-4}$alkyl or $R^{28}$ and $R^{29}$ together with the N to which they are bonded form a 4-6 membered saturated or unsaturated heterocyclic ring optionally comprising another heteroatom selected from O, S and N;
$R^{30}$ is H or $C_{1-4}$alkyl;
m is 1-2;
n is 1-3;
p is 0 or 1;
$X^1$ and $X^3$ are independently O, S, N or $CR^{31}$ and $X^2$ is N or $CR^{31}$ with the proviso that at least one of $X^1$-$X^3$ must be N and that no more than one of $X^1$ and $X^3$ can be O or S or
$X^3$ together with $R^2$, wherein $X^3$ is $CR^{31}$, form a 5 to 7 membered unsaturated carbocyclic ring optionally comprising a N;
$Y^1$-$Y^3$ are $CR^{32}$;
$R^{31}$ is H or $C_{1-6}$alkyl; and
$R^{32}$ is H, $C_{1-6}$alkyl, $C_{3-8}$cycloalkyl, $C_{1-6}$alkyloxy, halogen or CN, said $C_{1-6}$alkyl, $C_{3-8}$cycloalkyl and $C_{1-6}$alkyloxy being optionally substituted with one or more halogens;
or a pharmaceutically acceptable salt thereof.

2. The heterocyclic derivative according to claim 1 or a pharmaceutically acceptable salt thereof, wherein $R^1$ is $CF_3$.

3. The heterocyclic derivative according to claim 1 or a pharmaceutically acceptable salt thereof, wherein $R^2$ is methyl optionally substituted with halogen, OH or $NR^{18}R^{19}$, wherein $R^{18}$ and $R^{19}$ have the previously defined meanings.

4. The heterocyclic derivative according to claim 1 or a pharmaceutically acceptable salt thereof, wherein $R^3$ is H.

5. The heterocyclic derivative according to claim 1 or a pharmaceutically acceptable salt thereof, wherein $R^4$ is methyl, ethyl, isopropyl or tertiary-butyl, wherein said methyl, ethyl, isopropyl and tertiary-butyl are optionally substituted with one or more halogens.

6. The heterocyclic derivative according to claim 1 or a pharmaceutically acceptable salt thereof, wherein $X^1$ and $X^2$ are N and $X^3$ is CH.

7. The heterocyclic derivative according to claim 1 or a pharmaceutically acceptable salt thereof, wherein $L^1$ is $CH_2$.

8. The heterocyclic derivative according to claim 1 or a pharmaceutically acceptable salt thereof, wherein $R^{18}$ and $R^{19}$ are independently H or $C_{1-4}$alkyl.

9. The heterocyclic derivative according to claim 1 or a pharmaceutically acceptable salt thereof, wherein $Y^1$-$Y^3$ are CH.

10. The heterocyclic derivative according to claim 1 or a pharmaceutically acceptable salt thereof, wherein $L^2$ is $NHSO_2$.

11. A heterocyclic derivative selected from:

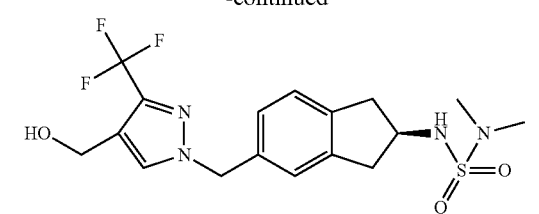
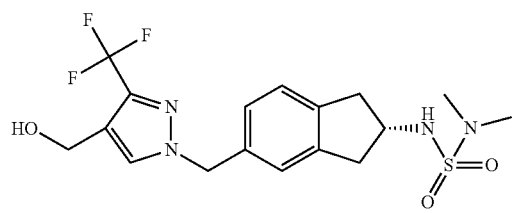
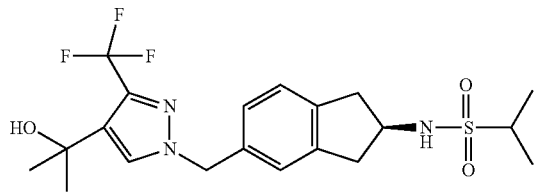
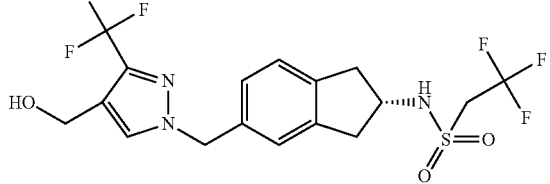
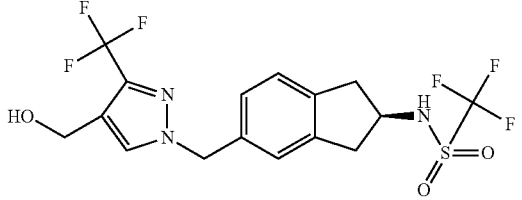
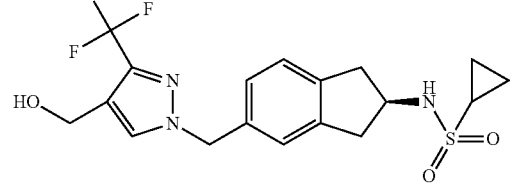
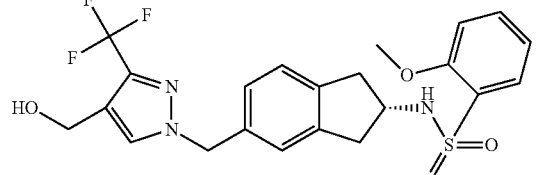
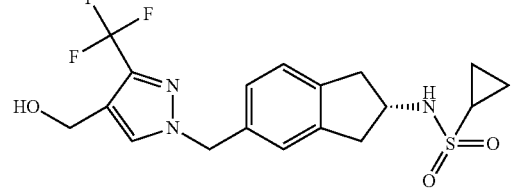
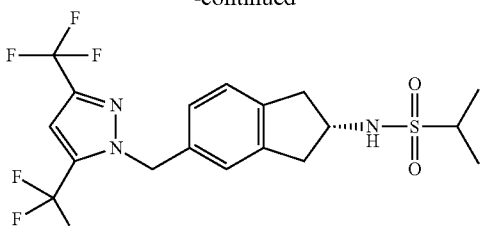
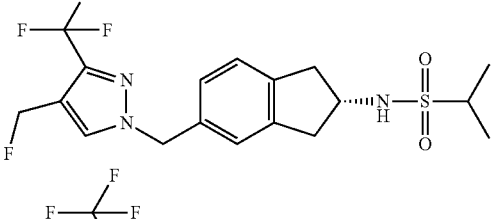
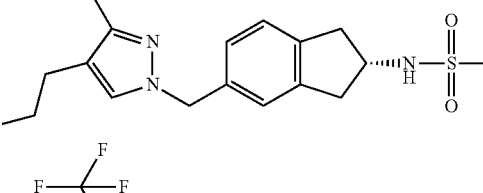
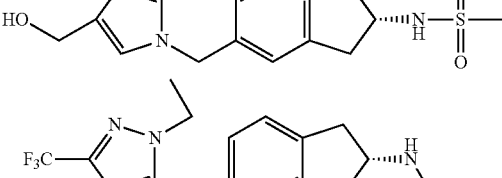
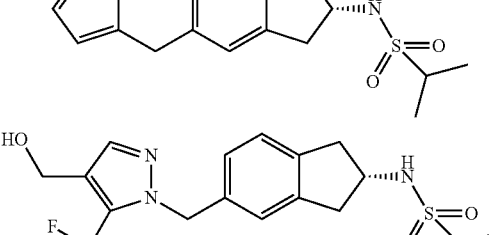
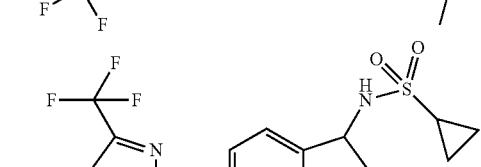
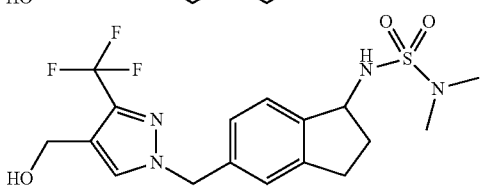

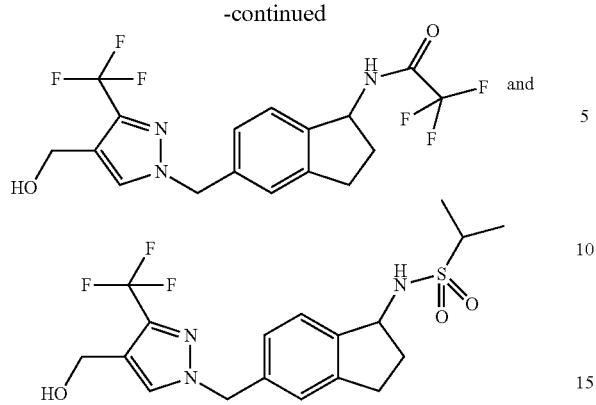

or a pharmaceutically acceptable salt thereof.

12. A pharmaceutical composition comprising a heterocyclic derivative according to claim 1 or a pharmaceutically acceptable salt thereof in admixture with a pharmaceutically acceptable auxiliary.

13. A pharmaceutical composition comprising a heterocyclic derivative according to claim 11 or a pharmaceutically acceptable salt thereof in admixture with a pharmaceutically acceptable auxiliary.

* * * * *